US011524950B2

(12) United States Patent
Schafer et al.

(10) Patent No.: US 11,524,950 B2
(45) Date of Patent: *Dec. 13, 2022

(54) TREATMENT OF IMMUNE-RELATED AND INFLAMMATORY DISEASES

(71) Applicant: Celgene Corporation, Summit, NJ (US)

(72) Inventors: Peter H. Schafer, Belle Mead, NJ (US); Ying Ye, Branchburg, NJ (US); Donna J. Sutherland, Green Brook, NJ (US); Rajesh Chopra, Sutton (GB); Anita Gandhi, Bernardsville, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/010,699

(22) Filed: Sep. 2, 2020

(65) Prior Publication Data

US 2021/0122727 A1    Apr. 29, 2021

Related U.S. Application Data

(63) Continuation of application No. 14/281,594, filed on May 19, 2014, now abandoned, which is a continuation-in-part of application No. 13/962,786, filed on Aug. 8, 2013, now Pat. No. 10,919,883.

(60) Provisional application No. 61/722,718, filed on Nov. 5, 2012, provisional application No. 61/681,491, filed on Aug. 9, 2012.

(51) Int. Cl.
| | | |
|---|---|---|
| *C07D 413/14* | (2006.01) |
| *A61K 31/5377* | (2006.01) |
| *C07D 401/04* | (2006.01) |
| *A61K 45/06* | (2006.01) |

(52) U.S. Cl.
CPC ........ *C07D 401/04* (2013.01); *A61K 31/5377* (2013.01); *A61K 45/06* (2013.01)

(58) Field of Classification Search
CPC ... A61K 31/5377; C07D 413/14; A61P 37/00; A61P 37/06; A61P 29/00; A61P 37/02; G01N 2333/70585; G01N 2800/52; G01N 33/6872
See application file for complete search history.

(56) References Cited

U.S. PATENT DOCUMENTS

| | | |
|---|---|---|
| 5,635,517 A | 6/1997 | Muller et al. |
| 2008/0045485 A1 | 2/2008 | Muir |
| 2011/0196150 A1 | 8/2011 | Man et al. |
| 2014/0045844 A1 | 2/2014 | Schafer et al. |
| 2014/0162282 A1 | 6/2014 | Schafer et al. |
| 2014/0343058 A1 | 11/2014 | Schafer et al. |
| 2015/0038511 A1 | 2/2015 | Schafer et al. |

FOREIGN PATENT DOCUMENTS

| | | | |
|---|---|---|---|
| JP | 2008-263917 A | 6/2008 | |
| WO | WO 99/47512 A1 | 9/1999 | |
| WO | WO 2002/012447 A2 | 2/2002 | |
| WO | WO 2003/018836 A2 | 3/2003 | |
| WO | WO 2004/026844 A1 | 4/2004 | |
| WO | WO 2007/133725 A1 | 11/2007 | |
| WO | WO 2008/076356 A1 | 6/2008 | |
| WO | WO 2008/115516 A2 | 9/2008 | |
| WO | WO 2008/119170 A1 | 10/2008 | |
| WO | WO 2009/124064 A1 | 10/2009 | |
| WO | WO 2009/126310 A2 | 10/2009 | |
| WO | WO 2010/065865 A2 | 6/2010 | |
| WO | WO 2010/121231 A1 | 10/2010 | |
| WO | WO 2011/100380 A1 | 8/2011 | |
| WO | WO-2011100380 A1 * | 8/2011 | ......... A61K 31/4412 |
| WO | WO 2011/109440 A1 | 9/2011 | |
| WO | WO 2011/112933 A1 | 9/2011 | |
| WO | WO 2012/024543 A1 | 2/2012 | |
| WO | WO 2012/115885 A1 | 8/2012 | |
| WO | WO 2013/185055 A1 | 12/2013 | |
| WO | WO 2014/004990 A2 | 1/2014 | |
| WO | WO 2014/020502 A2 | 2/2014 | |
| WO | WO 2014/025958 A2 | 2/2014 | |
| WO | WO 2015/054199 A1 | 4/2015 | |
| WO | WO 2015/179276 A1 | 11/2015 | |

OTHER PUBLICATIONS

Abud-Mendoza et al., "Treating severe systemic lupus erythematosus with rituximab. An open study," Reumatol. Clin., 5(4):147-152 (2009).
Anonymous: "Pomalidomide," Wikipedia, the free encyclopedia, Jul. 5, 2012, retrieved from the internet: URL:http://en.wikipedia.org/w/index.php?title=Pomalidomide&oldid=500784057, retrieved on Oct. 16, 2013 (2 pages).
Judson, "Extrapulmonary Sarcoidosis", Semin. Respir. Crit. Care Med., 28(1):83-101 (2007).
Khanna, "Diagnosis and treatment of systemic and localized scleroderma," Expert Rev. Dermatol., 6(3):287-302 (2011).
Kurzinski and Torok, "Cytokine profiles in localized scleroderma and relationship to clinical features," Cytokine, 55(2):157-164 (2011).
Risselada et al., "Therapy-resistant lupus skin disease successfully treated with rituximab", Rheumatology, 45:915-916 (2006).
Werth, "Current Treatment of Cutaneous Lupus Erythematosus", Dermatology Online Journal, 7(1):1-10 (2001).
Lee et al., "Disturbed Homeostasis and Multiple Signaling Defects in the Peripheral Blood B-Cell Compartment of Patients with Severe Chronic Sarcoidosis", Clin. Vaccine Immunol., 18(8):1306-1316 (2011).
Sweiss et al., "Rituximab in the treatment of refractory pulmonary sarcoidosis", Eur. Respir. J., 43:1525-1528 (2014).

(Continued)

*Primary Examiner* — Jean P Cornet
(74) *Attorney, Agent, or Firm* — Jones Day

(57) ABSTRACT

Provided herein are methods of using compounds and compositions for modulating leukocytic activity, including activity of B cells and/or T cells monocytes, macrophages, and other lymphoid or myeloid-derived cell types, in immune-related diseases or inflammatory diseases. Pharmaceutical compositions and dosing regimens for use in the methods are also provided herein.

20 Claims, 59 Drawing Sheets

Specification includes a Sequence Listing.

(56) References Cited

OTHER PUBLICATIONS

Nies et al., "Impaired Immunoglobulin Synthesis by Peripheral Blood Lymphocytes in Systemic Lupus Erythematosus", Arthritis and Rheumatism, 21(1):51-57 (1978).
Nilsson et al., "Purification and characterization of IgG immunoconglutinins from patients with systemic lupus erythematosus: implications for a regulatory function", Clin. exp. lmmunol., 82:262-267 (1990).
Vyse et al., "Genetic Susceptibility to Systemic Lupus Erythematosus", Annu. Rev. Immunol. 16:261-292 (1998).
Buckley III et al., "A Comparison of Serum Immunoglobulin Concentrations in Sarcoidosis and Tuberculosis", Ann. Intern. Med. 72(1):37-42 (1970) (abstract only).
Wu et al., "Sarcoidosis", American Family Physician, 70(2):312-322 (2004).
Kong et al., Viral Oncology, Shanghai Medical University Press, pp. 245, Nov. 1996 (with English translation).
Lang et al., Clinical Immunodiagnostics, Guangdong Science and Technology Press, pp. 337-339, Jan. 2003 (with English translation).
Lopez-Girona et al., "Cereblon is direct protein target for immunomodulatory and antiproliferative acttivities of lenalidomide and pomalidomide," Leukemia, 26:2326-2335 (2012).
Lessard et al., "Identification of a Systemic Lupus Erythematosus Susceptibility Locus at 11p13 between PDHX and CD44 in a Multiethnic Study", The American Journal of Human Genetics, 88(1):83-91 (2011).
Jin et al., "Systemic lupus erythematosus patients have increased number of circulating plasmacytoid dendritic cells, but decreased myeloid dendritic cells with deficient CD83 expression", PubMed, Jul. 31, 2008, Retrieved from the Internet: URL :https://pubmed.ncbi.nlm.nih.gov/18625638/ [retrieved on Oct. 15, 2020].

\* cited by examiner

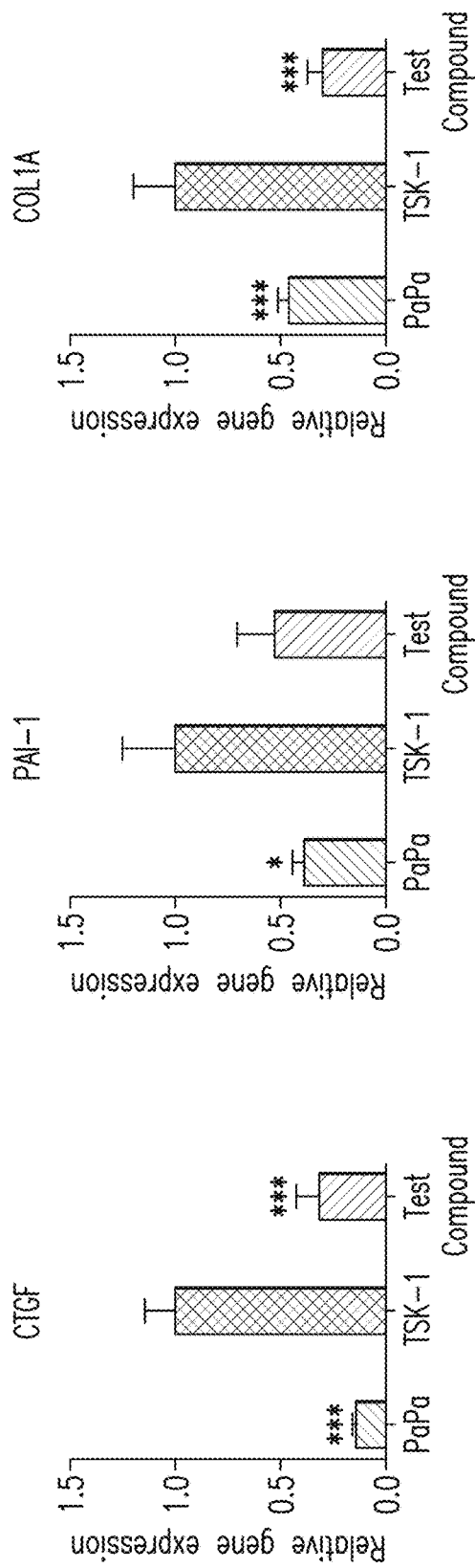
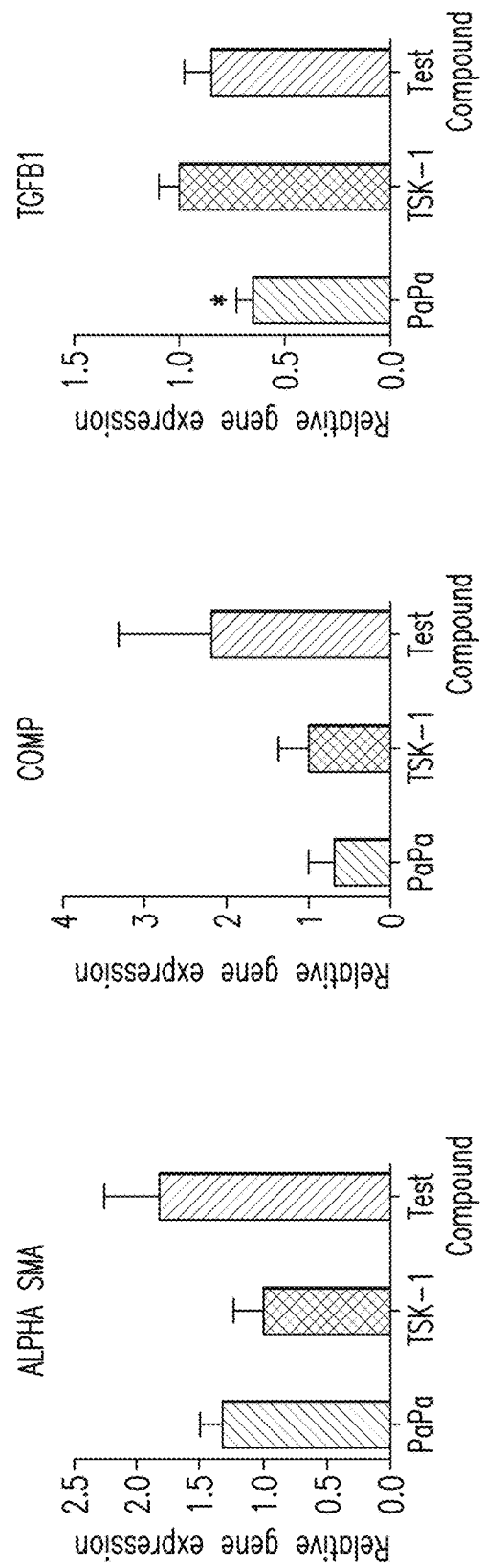
FIG. 49A FIG. 49B FIG. 49C
FIG. 49D FIG. 49E FIG. 49F

SEQUENCE LISTING

```
<160> NUMBER OF SEQ ID NOS: 2

<210> SEQ ID NO 1
<211> LENGTH: 344
<212> TYPE: PRT
<213> ORGANISM: Artificial Sequence
<220> FEATURE:
<223> OTHER INFORMATION: Human ActRIIA fused to a human Fc domain

<400> SEQUENCE: 1

Ile Leu Gly Arg Ser Glu Thr Gln Glu Cys Leu Phe Phe Asn Ala Asn
 1               5                  10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45
```

```
Gly Ser Ile Glu Ile Val Lys Gln Gly Cys Trp Leu Asp Asp Ile Asn
    50                  55                  60
Cys Tyr Asp Arg Thr Asp Cys Val Glu Lys Lys Asp Ser Pro Glu Val
 65                  70                  75                  80
Tyr Phe Cys Cys Cys Glu Gly Asn Met Cys Asn Glu Lys Phe Ser Tyr
                85                  90                  95
Phe Pro Glu Met Glu Val Thr Gln Pro Thr Ser Asn Pro Val Thr Pro
            100                 105                 110
Lys Pro Pro Thr Gly Gly Gly Thr His Thr Cys Pro Pro Cys Pro Ala
        115                 120                 125
Pro Glu Leu Leu Gly Gly Pro Ser Val Phe Leu Phe Pro Pro Lys Pro
130                 135                 140
Lys Asp Thr Leu Met Ile Ser Arg Thr Pro Glu Val Thr Cys Val Val
145                 150                 155                 160
Val Asp Val Ser His Glu Asp Pro Glu Val Lys Phe Asn Trp Tyr Val
                165                 170                 175
Asp Gly Val Glu Val His Asn Ala Lys Thr Lys Pro Arg Glu Glu Gln
            180                 185                 190
Tyr Asn Ser Thr Tyr Arg Val Val Ser Val Leu Thr Val Leu His Gln
        195                 200                 205
Asp Trp Leu Asn Gly Lys Glu Tyr Lys Cys Lys Val Ser Asn Lys Ala
210                 215                 220
Leu Pro Val Pro Ile Glu Lys Thr Ile Ser Lys Ala Lys Gly Gln Pro
225                 230                 235                 240
Arg Glu Pro Gln Val Tyr Thr Leu Pro Pro Ser Arg Glu Glu Met Thr
                245                 250                 255
Lys Asn Gln Val Ser Leu Thr Cys Leu Val Lys Gly Phe Tyr Pro Ser
            260                 265                 270
Asp Ile Ala Val Glu Trp Glu Ser Asn Gly Gln Pro Glu Asn Asn Tyr
        275                 280                 285
Lys Thr Thr Pro Pro Val Leu Asp Ser Asp Gly Ser Phe Phe Leu Tyr
290                 295                 300
Ser Lys Leu Thr Val Asp Lys Ser Arg Trp Gln Gln Gly Asn Val Phe
305                 310                 315                 320
Ser Cys Ser Val Met His Glu Ala Leu His Asn His Tyr Thr Gln Lys
                325                 330                 335
Ser Leu Ser Leu Ser Pro Gly Lys
            340

<210> SEQ ID NO 2
<211> LENGTH: 335
<212> TYPE: PRT
<213> ORGANISM: Artificial Sequence
<220> FEATURE:
<223> OTHER INFORMATION: Fusion protein comprising a soluble
      extracellular domain of ActRIIB fused to an Fc domain

<400> SEQUENCE: 2

Glu Thr Arg Glu Cys Ile Tyr Tyr Asn Ala Asn Trp Glu Leu Glu Arg
 1               5                  10                  15
Thr Asn Gln Ser Gly Leu Glu Arg Cys Glu Gly Glu Gln Asp Lys Arg
            20                  25                  30
Leu His Cys Tyr Ala Ser Trp Arg Asn Ser Ser Gly Thr Ile Glu Leu
        35                  40                  45
Val Lys Lys Gly Cys Trp Asp Asp Asp Phe Asn Cys Tyr Asp Arg Gln
50                  55                  60
```

```
Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Thr Gly Gly Thr His
            100                 105                 110

Thr Cys Pro Pro Cys Pro Ala Pro Glu Leu Leu Gly Gly Pro Ser Val
            115                 120                 125

Phe Leu Phe Pro Pro Lys Pro Lys Asp Thr Leu Met Ile Ser Arg Thr
            130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
                180                 185                 190

Val Leu Thr Val Leu His Gln Asp Trp Leu Asn Gly Lys Glu Tyr Lys
            195                 200                 205

Cys Lys Val Ser Asn Lys Ala Leu Pro Ala Pro Ile Glu Lys Thr Ile
210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
                260                 265                 270

Gly Gln Pro Glu Asn Asn Tyr Lys Thr Thr Pro Pro Val Leu Asp Ser
            275                 280                 285

Asp Gly Ser Phe Phe Leu Tyr Ser Lys Leu Thr Val Asp Lys Ser Arg
            290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335
```

TREATMENT OF IMMUNE-RELATED AND INFLAMMATORY DISEASES

1. RELATED APPLICATIONS

This application is a continuation application of U.S. application Ser. No. 14/281,594, filed on May 19, 2014, which is a continuation-in-part application of U.S. application Ser. No. 13/962,786, filed on Aug. 8, 2013, which claims benefit of U.S. Provisional Patent Application Nos. 61/722,718, filed on Nov. 5, 2012 and 61/681,491, filed on Aug. 9, 2012, all of which are hereby incorporated by reference in their entireties.

2. SEQUENCE LISTING

The present application is being filed with a Sequence Listing submitted as filename 12827-352-999_SeqListing.txt, of size 6,212 bytes, which was created on Oct. 16, 2013. The Sequence Listing is incorporated herein by reference in its entirety.

3. FIELD

Provided herein are methods of treating, preventing, and/or managing diseases associated with leukocytic activity, including activity of B cells and/or T cells, monocytes, macrophages, and other lymphoid or myeloid-derived cell types e.g., immune-related diseases or inflammatory diseases, comprising administering Compound I or a pharmaceutically acceptable salt, solvate, hydrate, stereoisomer, tautomer or racemic mixtures thereof, including (S)-3-[4-(4-morphlin-4-ylmethylbenzyloxy)-1-oxo-1,3-dihydro-isoindo-2-yl]piperidine-2,6-dione. Pharmaceutical compositions and dosing regimens for such treatment, prevention, and/or management are also provided herein.

4. BACKGROUND

Inflammatory and immune-related diseases modulated by lymphocytic activity, including activity of B cells and/or T cells, such as lupus, scleroderma, lupus pernio, sarcoidosis, Sjögren syndrome, ANCA-induced vasculitis, anti-phospholipid syndrome and myasthenia gravis, continue to be important medical problems.

Lupus or lupus erythematosus is a collection of autoimmune disorders that can cause chronic inflammation in various parts of the body, especially the skin, joints, blood, and kidneys. The body's immune system normally makes proteins called antibodies to protect the body against viruses, bacteria, and other foreign materials (i.e., antigens). In an autoimmune disorder such as lupus, the immune system loses its ability to tell the difference between antigens and its own cells and tissues and can make antibodies directed against its own cells and tissues to form immune complexes. These immune complexes can build up in the tissues and cause inflammation, injury to tissues and/or pain. The three most common types of lupus include systemic lupus erythematosus (SLE), cutaneous lupus erythematosus (CLE) and drug-induced lupus. More detailed descriptions of lupus or lupus erythematosus can be found in Wallace, 2000, *The Lupus Book: A Guide for Patients and Their Families*, Oxford University Press, Revised and Expanded Edition, which is incorporated by reference herein in its entirety.

Scleroderma is a rare disease with a stable incidence of approximately 19 cases per 1 million persons. The exact cause of scleroderma is unknown. Abnormalities involve autoimmunity and alteration of endothelial cell and fibroblast function. Systemic scleroderma usually begins with skin thickening, usually of the fingers, accompanied by Raynaud's phenomenon. Raynaud's disease typically precedes further manifestations of systemic scleroderma. Early in the disease the affected skin may be puffy and soft. The usual location of greatest skin thickening and hardening is the face, hands and fingers. Sclerodactyly is frequently present. Tendon friction rubs are often palpable on exam and can be painful. With more advanced disease, digital ulcers and auto-amputation may occur. Gastrointestinal dismotility is a feature, often manifested by heartburn, or by diarrhea with malabsorption or pseudo-obstruction. New onset hypertension or renal insufficiency are manifestations of the associated vascular injury. Heart failure or arrhythmia are also possible due to cardiac fibrosis. (Hachulla E, Launay D, *Diagnosis and classification of systemic sclerosis*, Clin Rev Allergy Immunol 2010; 40(2):78-83).

The major manifestations of scleroderma and in particular of systemic sclerosis are inappropriate excessive collagen synthesis and deposition, endothelial dysfunction, spasm, collapse and obliteration by fibrosis. In terms of diagnosis, an important clinical parameter is skin thickening proximal to the metacarpophalangeal joints. Raynaud's phenomenon is a frequent, almost universal component of scleroderma. It is diagnosed by color changes of the skin upon cold exposure. Ischemia and skin thickening are symptoms of Raynaud's disease.

Sarcoidosis is a disease characterized by granuloma formation, enhanced by lymphocyte and macrophages, usually classified as a T-helper type 1 response. Overproduction of tumor necrosis factor (TNF)-α, IL-8, and IL-18 by alveolar macrophages is thought to be a contributing factor to the underlying lung inflammation. Lupus pernio is a chronic disfiguring skin manifestation of sarcoidosis, primarily affecting the face. Sarcoidosis and associated lupus pernio have limited treatment options such as corticosteroids, which offer only modest benefit (Baughman R P, Judson M A, Teirstein A S, Moller D R, Lower E E. Thalidomide for chronic sarcoidosis. Chest. 2002 July; 122(1):227-32).

There remains a need for prophylactic or therapeutic drugs that can be used to treat or prevent immune-related and inflammatory diseases, including lupus, scleroderma, lupus pernio, sarcoidosis, Sjögren syndrome, ANCA-induced vasculitis, anti-phospholipid syndrome and myasthenia gravis.

5. SUMMARY

Provided herein are methods of treating, managing, ameliorating and/or preventing diseases, disorders and/or conditions associated with immune-related and inflammatory diseases comprising administering a therapeutically effective amount of a compound of formula I Compound I

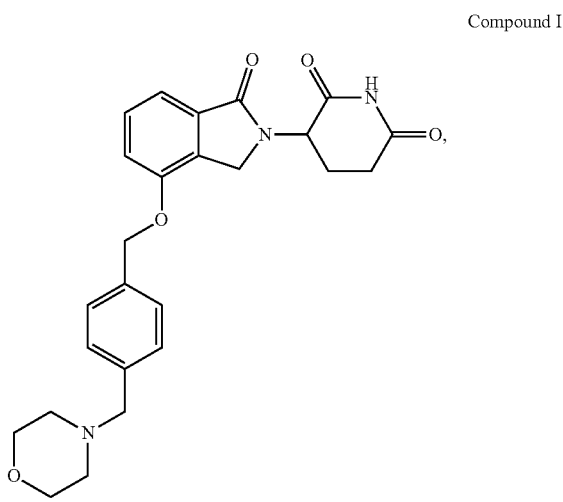 [SMILES: O=C1CCC(N2Cc3c(OCc4ccc(CN5CCOCC5)cc4)cccc3C2=O)C(=O)N1]

or a pharmaceutically acceptable salt, solvate, hydrate, stereoisomer, tautomer or racemic mixtures thereof.

In one embodiment, the compound is 3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of 3-[4-(4-morpholin-4-ylmethyl-benzyloxy)-1-oxo-1,3-dihydro-isoindol-2-yl]-piperidine-2,6-dione.

In one embodiment, the compound is 3-[4-(4-morpholin-4-ylmethyl-benzyloxy)-1-oxo-1,3-dihydro-isoindol-2-yl]-piperidine-2,6-dione hydrochloride.

In one embodiment, the compound is (S)-3-[4-(4-morpholin-4-ylmethyl-benzyloxy)-1-oxo-1,3-dihydro-isoindol-2-yl]-piperidine-2,6-dione, having the following structure:

Compound IA

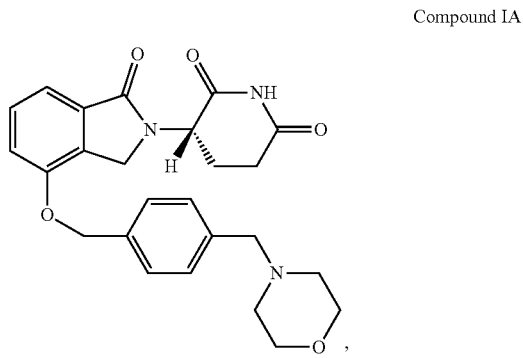 [SMILES: O=C1CC[C@H](N2Cc3c(OCc4ccc(CN5CCOCC5)cc4)cccc3C2=O)C(=O)N1]

or a pharmaceutically acceptable salt, solvate, hydrate, or tautomer thereof.

In one embodiment, the compound is (S)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (S)-3-[4-(4-morpholin-4-ylmethyl-benzyloxy)-1-oxo-1,3-dihydro-isoindol-2-yl]-piperidine-2,6-dione.

In one embodiment, the compound is (S)-3-[4-(4-morpholin-4-ylmethyl-benzyloxy)-1-oxo-1,3-dihydro-isoindol-2-yl]-piperidine-2,6-dione hydrochloride.

In one embodiment, the compound is (R)-3-[4-(4-morpholin-4-ylmethyl-benzyloxy)-1-oxo-1,3-dihydro-isoindol-2-yl]-piperidine-2,6-dione, having the following structure:

Compound IB

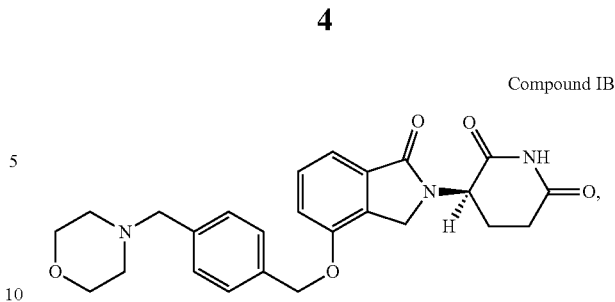

or a pharmaceutically acceptable salt, solvate, hydrate, or tautomer thereof.

In one embodiment, the compound is (R)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (R)-3-[4-(4-morpholin-4-ylmethyl-benzyloxy)-1-oxo-1,3-dihydro-isoindol-2-yl]-piperidine-2,6-dione.

In one embodiment, the compound is (R)-3-[4-(4-morpholin-4-ylmethyl-benzyloxy)-1-oxo-1,3-dihydro-isoindol-2-yl]-piperidine-2,6-dione hydrochloride.

In certain embodiments, the disease is selected from lupus, scleroderma, Sjögren syndrome, ANCA-induced vasculitis, anti-phospholipid syndrome and myasthenia gravis.

In one embodiment, provided herein are methods of modulating, e.g., reducing, leukocytic activity, including activity of B cells and/or T cells, monocytes, macrophages, and other lymphoid or myeloid-derived cell types, comprising contacting B cell and/or T cell with an effective amount of Compound I.

Also provided herein are pharmaceutical compositions, single unit dosage forms, and kits suitable for use in treating, preventing, ameliorating and/or managing diseases, disorders and/or conditions associated immune-related and inflammatory diseases, which comprise Compound I, optionally in combination with one or more other therapeutic agents.

In certain embodiments, Compound I is administered in combination with one or more therapeutic agents, i.e., pharmaceutical agents that are modulators of leukocytic activity, including activity of B cells and/or T cells, monocytes, macrophages, and other lymphoid or myeloid-derived cell types. The combinations encompass simultaneous as well as sequential administration.

6. BRIEF DESCRIPTION OF DRAWINGS

FIG. 49A depicts modulation of CTGF by (S)-3-[4-(4-morphlin-4-ylmethylbenzyloxy)-1-oxo-1,3-dihydro-isoindo-2-yl]piperidine-2,6-dione.

FIG. 49B depicts modulation of PAI-1 by (S)-3-[4-(4-morphlin-4-ylmethylbenzyloxy)-1-oxo-1,3-dihydro-isoindo-2-yl]piperidine-2,6-dione.

FIG. 49C depicts modulation of COL1A by (S)-3-[4-(4-morphlin-4-ylmethylbenzyloxy)-1-oxo-1,3-dihydro-isoindo-2-yl]piperidine-2,6-dione.

FIG. 49D depicts modulation of aSMA by (S)-3-[4-(4-morphlin-4-ylmethylbenzyloxy)-1-oxo-1,3-dihydro-isoindo-2-yl]piperidine-2,6-dione.

FIG. 49E depicts modulation of CCMP by (S)-3-[4-(4-morphlin-4-ylmethylbenzyloxy)-1-oxo-1,3-dihydro-isoindo-2-yl]piperidine-2,6-dione.

FIG. 49F depicts modulation of TGFB1 by (S)-3-[4-(4-morphlin-4-ylmethylbenzyloxy)-1-oxo-1,3-dihydro-isoindo-2-yl]piperidine-2,6-dione.

7. DETAILED DESCRIPTION

Figure 1:
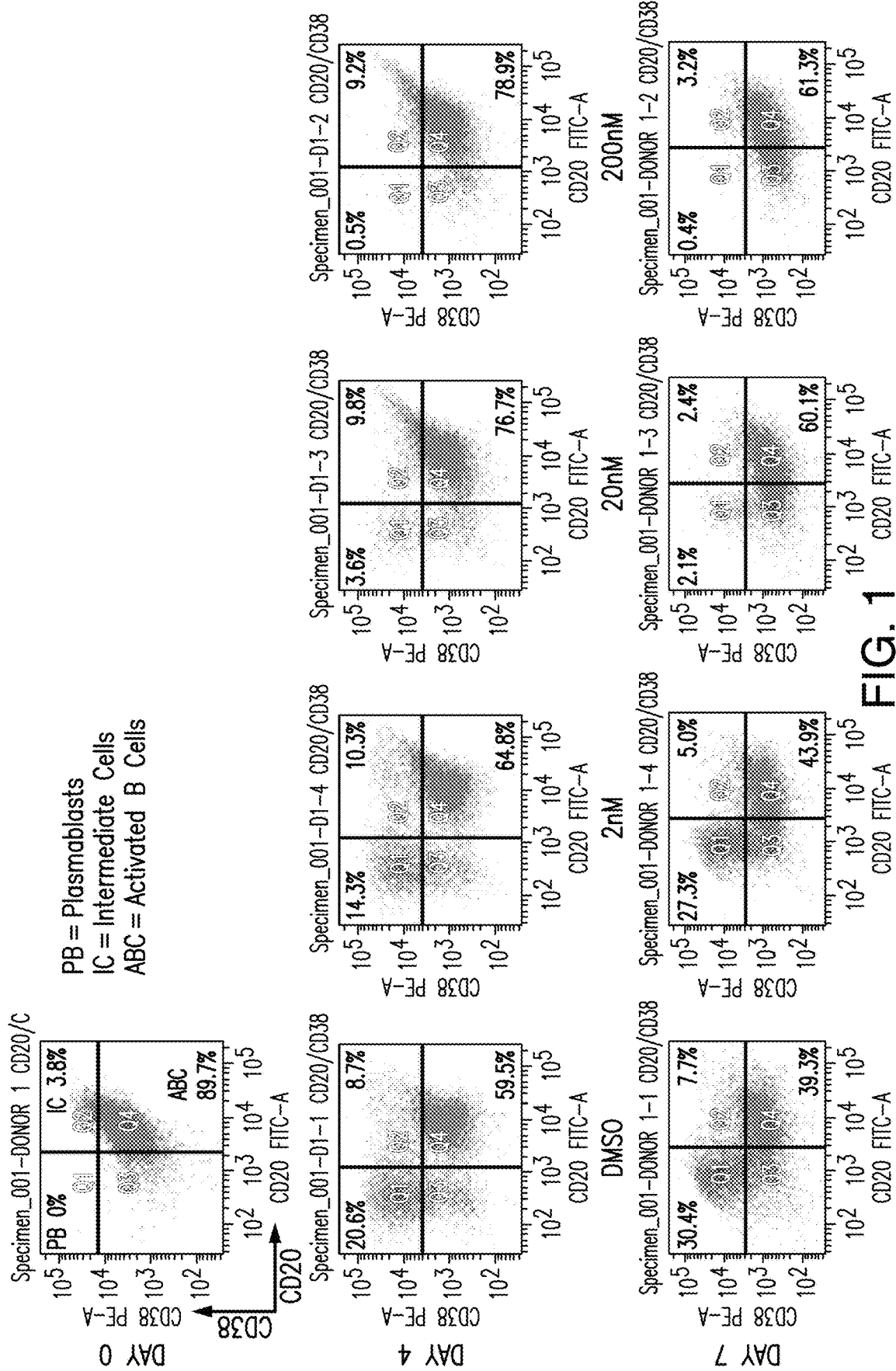
FIG. 1 depicts effect of (S)-3-[4-(4-morphlin-4-ylmethyl-benzyloxy)-1-oxo-1,3-dihydro-isoindo-2-yl]piperidine-2,6-dione on plasmablast and activated B cell differentiation.

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, and unless otherwise indicated, the terms "treat," "treating" and "treatment" refer to alleviating or reducing the severity of a disease or a symptom associated with the disease or condition being treated.

As used herein, "prevent", "prevention" and other forms of the word include the inhibition of onset or progression of a disease or disorder or a symptom of the particular disease or disorder. In some embodiments, subjects with familial history of cancer are candidates for preventive regimens. Generally, in the context of cancer, the term "preventing" refers to administration of the drug prior to the onset of signs or symptoms of a cancer, particularly in subjects at risk of cancer.

As used herein, and unless otherwise indicated, the term "managing" encompasses preventing the recurrence of the particular disease or disorder in a subject who had suffered from it, lengthening the time a subject who had suffered from the disease or disorder remains in remission, reducing mortality rates of the subjects, and/or maintaining a reduction in severity or avoidance of a symptom associated with the disease or condition being managed.

As used herein, "subject" means an animal, typically a mammal, including a human being. As used herein, "patient" means a human subject.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder or enhances the therapeutic efficacy of another therapeutic agent.

As used herein, and unless otherwise specified, the term "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

As used herein and unless otherwise indicated, the term "pharmaceutically acceptable salt" includes, but is not limited to, a salt of an acidic group that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, methanesulfonate (mesylate), methylsulfate, muscate, napsylate, nitrate, pantothenate, phosphate/diphosphate, polygalacturonate, salicylate, stearate, succinate, sulfate, tannate, tartrate, teoclate, triethiodide, and pamoate.

As used herein and unless otherwise indicated, the term "hydrate" means a compound provided herein or a salt thereof, further including a stoichiometric or non-stoichiometric amount of water bound by non-covalent intermolecular forces. The hydrates can be crystalline or non-crystalline.

As used herein and unless otherwise indicated, the term "solvate" means a solvate formed from the association of one or more solvent molecules to compound provided herein. The term "solvate" includes hydrates (e.g., monohydrate, dihydrate, trihydrate, tetrahydrate, and the like). The solvates can be crystalline or non-crystalline.

As used herein, and unless otherwise specified, the term "stereoisomer" encompasses all enantiomerically/stereomerically pure and enantiomerically/stereomerically enriched compounds provided herein.

As used herein, and unless otherwise indicated, the term "stereomerically pure" or "enantiomerically pure" means that a compound comprises one stereoisomer and is substantially free of its counter stereoisomer or enantiomer. For example, a compound is stereomerically or enantiomerically pure when the compound contains 80%, 90%, or 95% or more of one stereoisomer and 20%, 10%, or 5% or less of the counter stereoisomer. In certain cases, a compound provided herein is considered optically active or stereomerically/enantiomerically pure (i.e., substantially the R-form or substantially the S-form) with respect to a chiral center when the compound is about 80% ee (enantiomeric excess) or greater, preferably, equal to or greater than 90% ee with respect to a particular chiral center, and more preferably 95% ee with respect to a particular chiral center.

As used herein, and unless otherwise indicated, the term "stereomerically enriched" or "enantiomerically enriched" encompasses racemic mixtures as well as other mixtures of stereoisomers of compounds provided herein (e.g., R/S=30/70, 35/65, 40/60, 45/55, 55/45, 60/40, 65/35 and 70/30).

The terms "co-administration" and "in combination with" include the administration of two or more therapeutic agents (for example, Compound I or a composition provided herein and another modulator of leukocytic activity, including activity of B cells and/or T cells, monocytes, macrophages, and other lymphoid or myeloid-derived cell types or other active agent) either simultaneously, concurrently or sequentially with no specific time limits. In one embodiment, Compound I and at least one other agent are present in the cell or in the subject's body at the same time or exert their biological or therapeutic effect at the same time. In one embodiment, the therapeutic agent(s) are in the same composition or unit dosage form. In another embodiment, the therapeutic agent(s) are in separate compositions or unit dosage forms.

A "B cell" is a lymphocyte that matures within the bone marrow, and includes a naive B cell, memory B cell, or effector B cell (plasma cells). The B cell herein may be a normal or non-malignant B cell.

A "T cell" is a lymphocyte that matures in thymus, and includes a helper T cell, a memory T cell, and a cytotoxic T cell.

As used herein "overall survival" refers to the time from randomization until death from any cause, and is measured in the intent-to-treat population. Overall survival can be evaluated in randomized controlled studies.

As used herein "objective response rate" refers to the proportion of patients with reduced predefined scleroderma symptoms at the end of a predefined period of time. Response duration is usually measured from the time of initial response until documented scleroderma progression.

As used herein "time to progression" means the time from randomization until objective scleroderma progression. In certain embodiments, time to progression does not include deaths.

As used herein "progression-free survival" means the time from randomization until objective scleroderma progression or death.

As used herein "time-to-treatment failure" means any endpoint(s) measuring time from randomization to discontinuation of treatment for any reason, including disease progression, treatment toxicity, and death.

As used herein "mortality" means a measure of the number of deaths in a given population.

As used herein "respiratory mortality" means patients who die from acute hypoxemia or other specific respiratory deterioration resulting in death such as need for mechanical ventilation leading to death, respiratory arrest, or any other event in a subject deemed to be respiratory in nature.

As used herein "respiratory hospitalization" means those hospitalized for deterioration in pulmonary status as documented by patient hospital admission notes or other medical opinion.

As used herein "modified Rodnan skin score" means a validated numerical scoring system to assess dermal skin thickness.

As used herein "skin thickness" means hard or indurated skin that can be evaluated using a variety of techniques including durometer and mRSS.

As used herein "skin induration" means skin that is hardened, red, inflamed, thickened or tender.

As used herein "dermatology quality of life index" means an evaluation of quality or life related to the skin symptoms for a patient having scleroderma.

As used herein "pulmonary function" means any measurement of forced expiratory flow, forced vital capacity, FEV 25-75%, lung volumes or vital capacity.

As used herein "carbon monoxide diffusing capacity" means an assessment of the uptake of carbon monoxide across the alveolar-capillary membrane. It can be a proxy for the measurement of the lungs ability to transfer oxygen from the lungs to the blood stream.

As used herein "Mahler Dyspnea index" means an instrument that provides clinical measurement of shortness of breath.

As used herein "Saint George's Respiratory Questionnaire score" means an instrument that measures quality of life in patients with pulmonary disease.

As used herein "UCLA scleroderma clinical trial consortium gastrointestinal tract score" means a questionnaire administered to patients having scleroderma to evaluate gastrointestinal symptoms associated with scleroderma (systemic sclerosis).

As used herein "flow-mediated dilatation" means any measurement of vascular endothelial function in a patient having scleroderma.

As used herein "six minute walk distance" means any evaluation of the distance a patient having scleroderma can walk within 6 minutes or any standardized procedure to evaluate ability to walk for a fixed period of time or distance.

As used herein "Baseline and Transition Dyspnea Indices (BDI/TDI)" means an interview-based measurements of breathlessness related to activities of daily living.

As used herein "index lesion" is a single, defined area of cutaneous involvement that exhibits the most severe and active sarcoidosis. The index lesion is located in such as position as to facilitate visual evaluation and measurement. Visual evaluation and measurement include, but are not limited to, observation by gross visual examination, microscopical observation via dermoscopy, and evauation and measurement by histology.

As used herein "Modified Sarcoidosis Activity and Severity Index" means a validated numerical scoring system to assess sarcoidosis activity and severity in a patient. The index includes, but is not limited to, scores for the symptom domains of erythema, induration and desquamation and area scores of the index lesion.

As used herein "Physician's and Subject's Global Assessment of Disease Activity score" means an instrument that provides clinical measurement of sarcoidosis activity.

As used herein "6-Minute Walking Test score" means an instrument that provides clinical measurement of shortness of breath of a patient of sarcoidosis after walking for 6 minutes.

As used herein "Functional Assessment of Chronic Illness Therapy-Fatigue (FACIT-F) score" means an instrument that provides clinical measurement of fatigue of a patient with sarcoidosis.

As used herein "Physician's Overall Skin Response Assessment score" means an instrument that provides clinical assessment of a target lesion in a patient with sarcoidosis.

As used herein "FVC" means the total amount of air that can be forcibly blown out after full inspiration. FVC is measured in liters.

As used herein "$FEV_1$" means the amount of air that can be forcibly blown out in one second. $FEV_1$ is measured in liters.

As used herein "chest radiographic Likert score" means an instrument that provides clinical assessment of the chest condition in a patient with sarcoidosis.

As used herein, pomalidomide refers to the following compound:

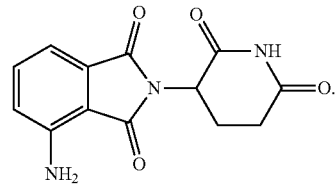 [SMILES: Nc1cccc2c1C(=O)N(C1CCC(=O)NC1=O)C2=O]

7.1 Compound I

In certain embodiments, Compound I for use in the methods provided herein, including the combination therapy, and in compositions provided herein is a compound of formula:

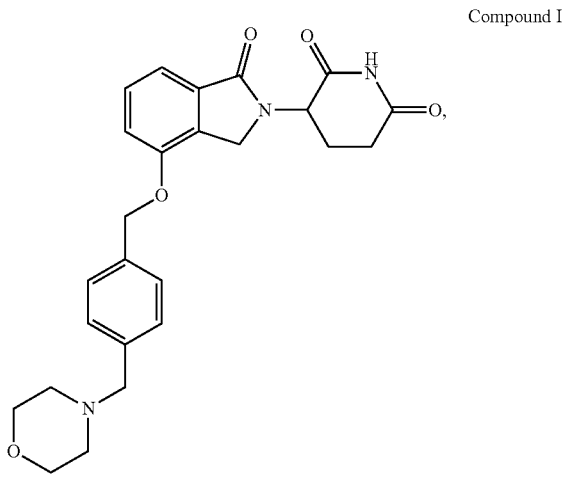 [SMILES: O=C1CCC(N2Cc3c(OCc4ccc(CN5CCOCC5)cc4)cccc3C2=O)C(=O)N1]

Compound I or a pharmaceutically acceptable salt, solvate, hydrate, stereoisomer, tautomer or racemic mixtures thereof.

In one embodiment, the compound is (S)-3-[4-(4-morpholin-4-ylmethyl-benzyloxy)-1-oxo-1,3-dihydro-isoindol-2-yl]-piperidine-2,6-dione, having the following structure:

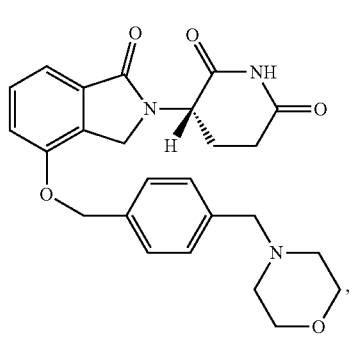

Compound IA or a pharmaceutically acceptable salt, solvate, hydrate, or tautomer thereof.

In one embodiment, the compound is (S)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (S)-3-[4-(4-morpholin-4-ylmethyl-benzyloxy)-1-oxo-1,3-dihydro-isoindol-2-yl]-piperidine-2,6-dione.

In one embodiment, the compound is (S)-3-[4-(4-morpholin-4-ylmethyl-benzyloxy)-1-oxo-1,3-dihydro-isoindol-2-yl]-piperidine-2,6-dione hydrochloride.

In one embodiment, the compound is (R)-3-[4-(4-morpholin-4-ylmethyl-benzyloxy)-1-oxo-1,3-dihydro-isoindol-2-yl]-piperidine-2,6-dione, having the following structure:

Compound IB

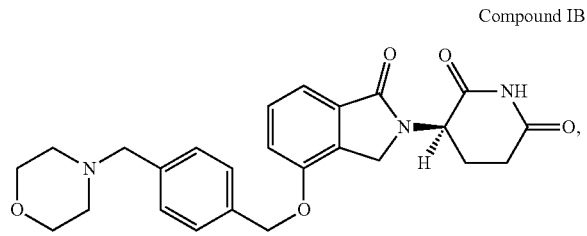 [SMILES: O=C1CC[C@@H](N2Cc3c(OCc4ccc(CN5CCOCC5)cc4)cccc3C2=O)C(=O)N1]

or a pharmaceutically acceptable salt, solvate, hydrate, or tautomer thereof.

In one embodiment, the compound is (R)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (R)-3-[4-(4-morpholin-4-ylmethyl-benzyloxy)-1-oxo-1,3-dihydro-isoindol-2-yl]-piperidine-2,6-dione.

In one embodiment, the compound is selected from 3-[4-(4-morpholin-4-ylmethyl-benzyloxy)-1-oxo-1,3-dihydro-isoindol-2-yl]-piperidine-2,6-dione, 3-[4-(4-morphlin-4-ylmethylbenzyloxy)-1-oxo-1,3-dihydro-isoindo-2-yl]piperidine-2,6-dione hydrochloride, (R)-3-[4-(4-morphlin-4-ylmethylbenzyloxy)-1-oxo-1,3-dihydro-isoindo-2-yl]piperidine-2,6-dione, (R)-3-[4-(4-morphlin-4-ylmethylbenzyloxy)-1-oxo-1,3-dihydro-isoindo-2-yl]piperidine-2,6-dione hydrochloride, (S)-3-[4-(4-morphlin-4-ylmethylbenzyloxy)-1-oxo-1,3-dihydro-isoindo-2-yl]piperidine-2,6-dione and (S)-3-[4-(4-morphlin-4-ylmethylbenzyloxy)-1-oxo-1,3-dihydro-isoindo-2-yl]piperidine-2,6-dione hydrochloride.

Compound I or a pharmaceutically acceptable salt, solvate, hydrate, stereoisomer, tautomer or racemic mixtures thereof can be prepared by methods known to one of skill in the art, for example, according to the procedure described in US Publication No. 2011/0196150, the entirety of which is incorporated herein by reference.

An exemplary method for preparation is described in Example 1.

7.2 Methods of Treatment

Provided herein are methods of treating, preventing, and/or managing diseases, disorders and/or conditions associated with immune-related and inflammatory diseases comprising administering a therapeutically effective amount of Compound I or a pharmaceutically acceptable salt, solvate, hydrate, stereoisomer, tautomer or racemic mixtures thereof to a patient in need thereof. In certain embodiments, the disease is selected from lupus, scleroderma, Sjögren syndrome, ANCA-induced vasculitis, anti-phospholipid syndrome and myasthenia gravis. In certain embodiments, the disease is lupus or scleroderma.

The sensitivity of Compound I or a pharmaceutically acceptable salt, solvate, hydrate, stereoisomer, tautomer or racemic mixtures thereof can be studied in various in vivo and in vitro assays, including animal models known to one of skill in the art for immune-related and inflammatory diseases, including, but not limited to MRL/MpJ-Faslpr/J mouse model of systemic lupus erythematosus, NZBWF1/J mouse model of systemic lupus erythematosus, bleomycin-induced skin fibrosis model, and murine tight skin-1 (Tsk-1) mouse model.

7.2.1 Treatment of Scleroderma

In certain embodiments, provided herein are methods of treating, preventing, and/or managing scleroderma or a symptom thereof, comprising administering a therapeutically effective amount of Compound I or a pharmaceutically acceptable salt, solvate, hydrate, stereoisomer, tautomer or racemic mixtures thereof to a patient having scleroderma. In one embodiment, provided herein are methods of treating, preventing, and/or managing scleroderma or a symptom thereof, comprising administering an effective amount of (S)-3-[4-(4-morphlin-4-ylmethylbenzyloxy)-1-oxo-1,3-dihydro-isoindo-2-yl]piperidine-2,6-dione or a pharmaceutically acceptable salt thereof.

In certain embodiments, provided herein are methods of preventing scleroderma or a symptom thereof, comprising administering an effective amount of Compound I or a pharmaceutically acceptable salt, solvate, hydrate, stereoisomer, tautomer or racemic mixtures thereof to a patient at risk of having scleroderma. In one embodiment, provided herein are methods of preventing scleroderma or a symptom thereof, comprising administering an effective amount of (S)-3-[4-(4-morphlin-4-ylmethylbenzyloxy)-1-oxo-1,3-dihydro-isoindo-2-yl]piperidine-2,6-dione or a pharmaceutically acceptable salt thereof.

In certain embodiments, the scleroderma is localized, systemic, limited or diffuse scleroderma.

In certain embodiments, the systemic scleroderma comprises CREST syndrome (Calcinosis, Raynaud's syndrome, esophagaeal dysfunction or dysmotility, sclerodactyly, telangiectasia). Scleroderma is also known as systemic sclerosis or progressive systemic sclerosis. In certain embodiments, provided herein are methods of treating or preventing Raynaud's disease or syndrome. In certain embodiments, systemic sclerosis comprises scleroderma lung disease, scleroderma renal crisis, cardiac manifestations, muscular weakness (including fatigue or limited CREST), gastrointestinal dysmotility and spasm, and abnormalities in the central, peripheral and autonomic nervous system (including carpal tunnel syndrome followed by trigeminal neuralgia). It also includes general disability, including depression, and impact on quality of life.

In certain embodiments, limited scleroderma is limited to the hands, the face, neck, or combinations thereof.

In certain embodiments, diffuse scleroderma comprises skin tightening and also occurs above the wrists (or elbows). In certain embodiments, the diffuse systemic sclerosis is sine scleroderma, comprising internal organ fibrosis, but no skin tightening; or familial progressive systemic sclerosis.

In one embodiment, scleroderma is not associated with wasting, such as disease-related wasting.

In one embodiment, provided herein are methods for the reduction, inhibition, or prevention of one or more of the following symptoms of scleroderma: (i) gradual hardening, thickening, and tightening of the skin (e.g., in extremities, such as hands, face, and feet); (ii) skin discoloration; (iii) numbness of extremities; (iv) shiny skin; (v) small white lumps under the surface of the skin that erupt into a chalky white fluid; (vi) Raynaud's esophagaeal dysfunction (pain, numbness, and/or color changes in the hands caused by spasm of the blood vessels upon exposure to cold or emotional stress); (vii) telangiectasia (red spots on, e.g., the hands, palms, forearms, face, and lips); (viii) pain and/or stiffness of the joints; (ix) swelling of the hands and feet; (x) itching of the skin; (xi) stiffening and curling of the fingers; (xii) ulcers (sores) on the outside of certain joints, such as knuckles and elbows; (xiii) digestive problems, such as heartburn, difficulty in swallowing, diarrhea, irritable bowel, and constipation; (xiv) fatigue and weakness; (xv) shortness of breath; (xvi) arthritis; (xvii) hair loss; (xviii) internal organ problems; (xix) digital ulcers; or (xx) digital auto-amputation, comprising administering an effective amount of Compound I to a patient in need thereof.

Without being bound to any particular theory, it is believed that Compound I or a pharmaceutically acceptable salt, solvate, hydrate, stereoisomer, tautomer or racemic mixtures thereof enhances Th1 immune response, and suppresses Th2 immune response, which may result in anti-fibrotic effects in the skin.

Further provided herein are methods for improving or reducing the skin thickness of a patient having scleroderma comprising administering an effective amount of Compound I or a pharmaceutically acceptable salt, solvate, hydrate, stereoisomer, tautomer or racemic mixtures thereof to the patient. In one embodiment, the skin thickness is reduced by about 20%, about 25%, about 30%, about 40%, about 50%, about 60%, about 70% about 80%, about 90% or more.

Further provided herein are methods for achieving one or more clinical endpoints associated with scleroderma comprising administering an effective amount of Compound I or a pharmaceutically acceptable salt, solvate, hydrate, stereoisomer, tautomer or racemic mixtures thereof to a patient in need thereof.

Further provided herein are methods for increasing the overall survival, objective response rate, time to progression, progression-free survival and/or time-to-treatment failure of a patient having scleroderma comprising administering an effective amount of Compound I or a pharmaceutically acceptable salt, solvate, hydrate, stereoisomer, tautomer or racemic mixtures thereof to the patient.

Further provided herein are methods for decreasing mortality, respiratory mortality and/or respiratory hospitalization of a patient having scleroderma comprising administering an effective amount of Compound I or a pharmaceutically acceptable salt, solvate, hydrate, stereoisomer, tautomer or racemic mixtures thereof to the patient.

Further provided herein are methods for improving the modified Rodnan skin score of a patient having scleroderma comprising administering an effective amount of Compound I or a pharmaceutically acceptable salt, solvate, hydrate, stereoisomer, tautomer or racemic mixtures thereof to the patient. In one embodiment, the improvement in modified Rodnan skin score is 5, 10, 15 or 20 points or more.

Further provided herein are methods for improving or reducing the skin thickness of a patient having scleroderma comprising administering an effective amount of Compound I or a pharmaceutically acceptable salt, solvate, hydrate, stereoisomer, tautomer or racemic mixtures thereof to the patient. In one embodiment, the skin thickness is reduced by about 20%, about 25%, about 30%, about 40%, about 50%, about 60%, about 70% about 80%, about 90% or more.

Further provided herein are methods for improving or reducing skin induration of a patient having scleroderma comprising administering an effective amount of Compound I or a pharmaceutically acceptable salt, solvate, hydrate, stereoisomer, tautomer or racemic mixtures thereof to the patient.

Further provided herein are methods for improving the dermatology quality of life index of a patient having scleroderma comprising administering an effective amount of Compound I or a pharmaceutically acceptable salt, solvate, hydrate, stereoisomer, tautomer or racemic mixtures thereof to the patient.

Further provided herein are methods for improving the pulmonary function of a patient having scleroderma comprising administering an effective amount of Compound I or a pharmaceutically acceptable salt, solvate, hydrate, stereoisomer, tautomer or racemic mixtures thereof to the patient.

Further provided herein are methods for improving the carbon monoxide diffusing capacity of a patient having scleroderma comprising administering an effective amount of Compound I or a pharmaceutically acceptable salt, solvate, hydrate, stereoisomer, tautomer or racemic mixtures thereof to the patient. In one embodiment, the carbon monoxide diffusing capacity of a patient is improved by an improvement in the diffusing capacity of the lung for carbon monoxide ($D_L$co) of about 10%, about 20%, about 25%, about 30%, about 40%, about 50%, about 60%, about 70% about 80%, about 90% or more.

Further provided herein are methods for improving the Mahler Dyspnea index of a patient having scleroderma comprising administering an effective amount of Compound I or a pharmaceutically acceptable salt, solvate, hydrate, stereoisomer, tautomer or racemic mixtures thereof to the patient. In one embodiment, the improvement in Mahler Dyspnea index is 4, 5, 6, 7, 8, 9 or 10 points or more.

Further provided herein are methods for improving the Saint George's Respiratory Questionnaire score of a patient having scleroderma comprising administering an effective amount of Compound I or a pharmaceutically acceptable salt, solvate, hydrate, stereoisomer, tautomer or racemic mixtures thereof to the patient. In one embodiment, the improvement in Saint George's Respiratory Questionnaire score is 4, 8, 12, 16, 20, 24, 28, 32, 36, 40, 44, 48, 52 points or more.

Further provided herein are methods for improving the UCLA scleroderma clinical trial consortium gastrointestinal tract score of a patient having scleroderma comprising administering an effective amount of Compound I or a pharmaceutically acceptable salt, solvate, hydrate, stereoisomer, tautomer or racemic mixtures thereof to the patient.

Further provided herein are methods for treating or preventing digital ulcer of a patient or patient population having scleroderma comprising administering an effective amount of Compound I or a pharmaceutically acceptable salt, solvate, hydrate, stereoisomer, tautomer or racemic mixtures thereof to the patient.

Further provided herein are methods improving flow-mediated dilatation of a patient having scleroderma comprising administering an effective amount of Compound I or a pharmaceutically acceptable salt, solvate, hydrate, stereoisomer, tautomer or racemic mixtures thereof to the patient.

Further provided herein are methods improving or increasing the six minute walk distance of a patient having scleroderma comprising administering an effective amount of Compound I or a pharmaceutically acceptable salt, solvate, hydrate, stereoisomer, tautomer or racemic mixtures thereof to the patient. In one embodiment, the improvement in the six minute walk distance is about 200 meters, about 250 meters, about 300 meters, about 350 meters, about 400 meters or more.

7.2.2 Treatment of Lupus Erythematosus

In certain embodiments, provided herein are methods of treating, preventing, and/or managing lupus erythematosus or a symptom thereof, comprising administering a therapeutically effective amount of Compound I or a pharmaceutically acceptable salt, solvate, hydrate, stereoisomer, tautomer or racemic mixtures thereof to a patient having lupus erythematosus. In one embodiment, provided herein are methods of treating, preventing, and/or managing lupus erythematosus or a symptom thereof, comprising administering a therapeutically effective amount of (S)-3-[4-(4-morphlin-4-ylmethylbenzyloxy)-1-oxo-1,3-dihydro-isoindo-2-yl]piperidine-2,6-dione or a pharmaceutically acceptable salt thereof to a patient having lupus erythematosus.

In one embodiment, provided herein are methods of preventing lupus erythematosus or a symptom thereof, comprising administering an effective amount of Compound I or a pharmaceutically acceptable salt, solvate, hydrate, stereoisomer, tautomer or racemic mixtures thereof to a patient at risk of having lupus erythematosus. In one embodiment, provided herein are methods of preventing lupus erythematosus or a symptom thereof, comprising administering an effective amount of (S)-3-[4-(4-morphlin-4-ylmethylbenzyloxy)-1-oxo-1,3-dihydro-isoindo-2-yl]piperidine-2,6-dione or a pharmaceutically acceptable salt thereof to a patient at risk of having lupus erythematosus.

In certain embodiments, provided herein are methods for treating, preventing, and/or managing systemic lupus erythematosus (SLE), cutaneous lupus erythematosus (CLE) or drug-induced lupus.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: *Harrison's Principles of Internal Medicine* (16th edition). New York (US): McGraw-Hill; 2005. pp. 1960-1967).

Symptoms of SLE vary from person to person, and may come and go. In most patients, the symptoms include joint pain and swelling. Frequently affected joints are the fingers, hands, wrists, and knees. Some patients develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash-a "butterfly" rash over the cheeks and bridge of the nose affects about half of people with SLE, in some patients, the rash gets worse in sunlight, and the rash may also be widespread.

Other symptoms depend on what part of the body is affected, and may include the following:
Brain and nervous system: headaches, numbness, tingling, seizures, vision problems, personality changes,
Digestive tract: abdominal pain, nausea, and vomiting,
Heart: abnormal heart rhythms (arrhythmias),
Lung: coughing up blood and difficulty breathing, and
Skin: patchy skin color, fingers that change color when cold (Raynaud's phenomenon).
Some patients only have skin symptoms. This is called discoid lupus.

In one embodiment, provided herein are methods of treating moderate, severe, or very severe SLE. The term "severe SLE" as used herein refers to an SLE condition where the patient has one or more severe or life-threatening symptoms (such as hemolytic anemia, extensive heart or lung involvement, kidney disease, or central nervous system involvement).

Further provided herein are methods for achieving one or more clinical endpoints associated with SLE comprising administering an effective amount of Compound I or a pharmaceutically acceptable salt, solvate, hydrate, stereoisomer, tautomer or racemic mixtures thereof to a patient in need thereof.

Further provided herein are methods for increasing the overall survival, objective response rate, time to progression, progression-free survival and/or time-to-treatment failure of a patient having SLE comprising administering an effective amount of Compound I or a pharmaceutically acceptable salt, solvate, hydrate, stereoisomer, tautomer or racemic mixtures thereof to the patient.

In certain embodiment, Compound I or a pharmaceutically acceptable salt, solvate, hydrate, stereoisomer, tautomer or racemic mixtures thereof acts as an inhibitor of primary human memory CD19+ B-cell differentiation to the plasmablast stage. Without being bound to any particular theory, it is believed that Compound I or a pharmaceutically acceptable salt, solvate, hydrate, stereoisomer, tautomer or racemic mixtures thereof blocks cells at a premature stage thereby decreasing the numbers of plasmablasts that are capable of producing high levels of immunoglobulin. A functional consequence of this effect is reduced immunoglobulin G (IgG) and immunoglobulin M (IgM) production in these differentiation cultures.

In certain embodiments, Compound I or a pharmaceutically acceptable salt, solvate, hydrate, stereoisomer, tautomer or racemic mixtures thereof inhibits of the ability of primary human memory CD19+ B-cells to differentiate to the plasmablast stage. In certain embodiments, Compound I or a pharmaceutically acceptable salt, solvate, hydrate, stereoisomer, tautomer or racemic mixtures thereof has no significant effect on mature CD138+ plasma cells in short term cultures. In certain embodiments, Compound I or a pharmaceutically acceptable salt, solvate, hydrate, stereoisomer, tautomer or racemic mixtures thereof inhibits B cell differentiation factors including interferon regulatory factor 4 (TRF4), lymphocyte-induced maturation protein (BLIMP), X-box-protein-1 (XBP-1) and B cell lymphoma 6 (Bcl6).

7.2.3 Treatment of Sarcoidosis

In certain embodiments, provided herein are methods of treating, preventing, and/or managing sarcoidosis or a symptom thereof, comprising administering a therapeutically effective amount of Compound I or a pharmaceutically acceptable salt, solvate, hydrate, stereoisomer, tautomer or racemic mixtures thereof to a patient having sarcoidosis. In one embodiment, provided herein are methods of treating, preventing, and/or managing sarcoidosis or a symptom thereof, comprising administering an effective amount of (S)-3-[4-(4-morphlin-4-ylmethylbenzyloxy)-1-oxo-1,3-dihydro-isoindo-2-yl]piperidine-2,6-dione or a pharmaceutically acceptable salt thereof.

In certain embodiments, provided herein are methods of preventing sarcoidosis or a symptom thereof, comprising administering an effective amount of Compound I or a pharmaceutically acceptable salt, solvate, hydrate, stereoisomer, tautomer or racemic mixtures thereof to a patient at risk of having sarcoidosis. In one embodiment, provided herein are methods of preventing sarcoidosis or a symptom thereof, comprising administering an effective amount of (S)-3-[4-(4-morphlin-4-ylmethylbenzyloxy)-1-oxo-1,3-dihydro-isoindo-2-yl]piperidine-2,6-dione or a pharmaceutically acceptable salt thereof.

Sarcoidosis is a disease characterized by granuloma formation, enhanced by lymphocyte and macrophages, usually classified as a T-helper type 1 response. Sarcoidosis patients often develop damage in a number of organs including, but not limited to, pulmonary, CNS, GI, lymphatics, optic, and renal systems. In one embodiment, the sarcoidosis is with lung involvement (e.g., pulmonary sarcoid), with skin involvement (e.g., cutaneous sarcoid), with heart involvement, or with brain involvement. In certain embodiments, the sarcoidosis is chronic cutaneous sarcoid (CCS). In one embodiment, the CCS is with pulmonary involvement. In another embodiment, the CCS is without pulmonary involvement. As used herein, sarcoidosis also includes the diseases associated with sarcoidosis (e.g., lupus pernio).

In one embodiment, provided herein are methods for the reduction, inhibition, or prevention of one or more of the following symptoms of sarcoidosis: (i) granulomas formulation; (ii) lupus pernio; (iii) skin lesions; (iv) dyspnea; (v) dry cough; (vi) chest pain, and (vii) fatigue, comprising administering an effective amount of Compound I to a patient in need thereof.

In certain embodiments, the patient has been diagnosed with chronic cutaneous sarcoid for at least 12 months. In some embodiments, the diagnosis of chronic cutaneous sarcoid is confirmed by cutaneous sarcoid biopsy. In certain embodiments, the patient has a Minimum Modified Sarcoidosis Activity and Severity Index (MSASI) of ≥1. In certain embodiments, the patient has at least 2 lesions >1 cm in longest dimension. In certain embodiments, the patient has no improvement from another chronic cutaneous sarcoid treatment for at least 3 months. In certain embodiments, the patient has a forced vital capacity (FVC) of ≥45% of predicted normal value. In certain embodiments, the patient has an estimated Glomerular Filtration Rate (eGFR) ≥60 mL/min. In some embodiments, the eGFR is calculated by MDRD [Modification of Diet in Renal Disease].

Further provided herein are methods for achieving one or more clinical endpoints associated with sarcoidosis comprising administering an effective amount of Compound I or a pharmaceutically acceptable salt, solvate, hydrate, stereoisomer, tautomer or racemic mixtures thereof to a patient in need thereof.

Further provided herein are methods for increasing the overall survival, objective response rate, time to progression, progression-free survival and/or time-to-treatment failure of a patient having sarcoidosis comprising administering an effective amount of Compound I or a pharmaceutically acceptable salt, solvate, hydrate, stereoisomer, tautomer or racemic mixtures thereof to the patient.

In certain embodiments, the clinical endpoint is improvement in the Modified Sarcoidosis Activity and Severity Index (MSASI) score of the patient having sarcoidosis. In some embodiments, provided herein are methods for improving or increasing the Modified Sarcoidosis Activity and Severity Index (MSASI) score of a patient having sarcoidosis comprising administering an effective amount of Compound I or a pharmaceutically acceptable salt, solvate, hydrate, stereoisomer, tautomer or racemic mixtures thereof to the patient. In one embodiment, the symptom domains of erythema, induration and desquamation are scored as follows: 0=none; 1=slight; 2=moderate; 3=severe; and 4=very severe. In one embodiment, the symptom score for domains of erythema, induration and/or desquamation in the patient is improved by at least 1, at least 2, at least 3, or at least 4 levels. In one embodiment, the area score of the index lesion is assessed as follows: 0=0%; 1=1-9%; 2=10-29%; 3=30-49%; 4=50-69%; 5=70-89%; and 6=90-100%. In one embodiment, the area score of the index lesion is improved by at least 20%, at least 30%, at least 40%, at least 50%, at least 60%, at least 70%, at least 80%, at least 90%, or more.

In certain embodiments, the clinical endpoint is improvement in the Physician's and Subject's Global Assessment of Disease Activity score of the patient having sarcoidosis. In some embodiments, provided herein are methods for improving or increasing the Physician's and Subject's Global Assessment of Disease Activity score of a patient having sarcoidosis comprising administering an effective amount of Compound I or a pharmaceutically acceptable salt, solvate, hydrate, stereoisomer, tautomer or racemic mixtures thereof to the patient. In one embodiment, the Physician's and Subject's Global Assessment of Disease Activity score of the patient is improved by at least 20%, at least 30%, at least 40%, at least 50%, at least 60%, at least 70%, at least 80%, at least 90%, or more.

In certain embodiments, the clinical endpoint is improvement in the 6-Minute Walking Test (6WMT) score of the patient having sarcoidosis. In some embodiments, provided herein are methods for improving or increasing the 6WMT score of a patient having sarcoidosis comprising administering an effective amount of Compound I or a pharmaceutically acceptable salt, solvate, hydrate, stereoisomer, tautomer or racemic mixtures thereof to the patient. In one embodiment, the 6WMT score is improved by at least 1, at least 2, at least 3, at least 4, at least 5, at least 6, at least 7, at least 8, or at least 9 levels based on the Borg Scale.

In certain embodiments, the clinical endpoint is improvement in the Functional Assessment of Chronic Illness Therapy-Fatigue (FACIT-F) score of the patient having sarcoidosis. In some embodiments, provided herein are methods for improving or increasing the FACIT-F score of a patient having sarcoidosis comprising administering an effective amount of Compound I or a pharmaceutically acceptable salt, solvate, hydrate, stereoisomer, tautomer or racemic mixtures thereof to the patient. In one embodiment, the FACIT-F score of the patient is improved by at least 20%, at least 30%, at least 40%, at least 50%, at least 60%, at least 70%, at least 80%, at least 90%, or more.

In certain embodiments, the clinical endpoint is improvement in the Dermoscopy for Lesion Assessment score of the patient having sarcoidosis. In some embodiments, provided herein are methods for improving or increasing the Dermoscopy for Lesion Assessment score of a patient having sarcoidosis comprising administering an effective amount of Compound I or a pharmaceutically acceptable salt, solvate, hydrate, stereoisomer, tautomer or racemic mixtures thereof to the patient. In one embodiment, the Dermoscopy for Lesion Assessment score of the patient is improved by at least 20%, at least 30%, at least 40%, at least 50%, at least 60%, at least 70%, at least 80%, at least 90%, or more.

In certain embodiments, the clinical endpoint is improvement in the Physician's Overall Skin Response Assessment score of the patient having sarcoidosis. In some embodiments, provided herein are methods for improving or increasing the Physician's Overall Skin Response Assessment score of a patient having sarcoidosis comprising administering an effective amount of Compound I or a pharmaceutically acceptable salt, solvate, hydrate, stereoisomer, tautomer or racemic mixtures thereof to the patient. In one embodiment, the Physician's Overall Skin Response Assessment is scored as follows: 1=markedly worsened; 2=worsened; 3=unchanged; 4=near resolution; and 5=complete resolution. In one embodiment, the Physician's Overall Skin Response Assessment score in the patient is improved by at least 1, at least 2, at least 3, or at least 4 levels.

In certain embodiments, the clinical endpoint is improvement in lesion of the patient having sarcoidosis as determined by photographic assessment. In some embodiments, provided herein are methods for improving lesion of a patient having sarcoidosis as determined by photographic assessment comprising administering an effective amount of Compound I or a pharmaceutically acceptable salt, solvate, hydrate, stereoisomer, tautomer or racemic mixtures thereof to the patient. In one embodiment, the lesion of the patient is improved by at least 20%, at least 30%, at least 40%, at least 50%, at least 60%, at least 70%, at least 80%, at least 90%, or more.

In certain embodiments, the clinical endpoint is improvement in lesion of the patient having sarcoidosis as determined by skin biopsy. In some embodiments, provided herein are methods for improving lesion of a patient having sarcoidosis as determined by skin biopsy comprising administering an effective amount of Compound I or a pharmaceutically acceptable salt, solvate, hydrate, stereoisomer, tautomer or racemic mixtures thereof to the patient. In one embodiment, the lesion is a non-facial lesion. In one embodiment, the improvement of lesion is characterized as one or more of changes in granuloma size and number, and epidermal thickness, and IHC staining for cells such as Giant cells, T cell staining (e.g., CD4 and CD8), and Dendritic cells/Langerhans staining (e.g., CD1a, CD83, DC-LAMP). In one embodiment, the lesion of the patient is improved by at least 20%, at least 30%, at least 40%, at least 50%, at least 60%, at least 70%, at least 80%, at least 90%, or more.

In certain embodiments, the clinical endpoint is improvement in one or more biomarkers associated with sarcoidosis of the patient having sarcoidosis. In some embodiments, provided herein are methods for improving, increasing, or decreasing one or more biomarkers associated with sarcoidosis of a patient having sarcoidosis comprising administering an effective amount of Compound I or a pharmaceutically acceptable salt, solvate, hydrate, stereoisomer, tautomer or racemic mixtures thereof to the patient. In one embodiment, the biomarker is a serum biomarker. In one embodiment, the biomarker is serum ACE, IgG, 25-hydroxy vitamin D (25-OH-vit D), or 1,25-dihydroxy vitamin D (1,25-vitD). In one embodiment, the biomarker is a plasma biomarker. In one embodiment, the biomarker is IL-12, sIL2R, or TNF-α. In one embodiment, the biomarker is peripheral blood total lymphocyte counts and B cell subsets and T cell activation markers (such as but not limited to HLA-DR, CD45RA, CD45RO, CD69, IL-2R, CD80, CD86).

In certain embodiments, the clinical endpoint is improvement in FVC or $FEV_1$ of the patient having sarcoidosis. In some embodiments, provided herein are methods for improving or increasing FVC or $FEV_1$ of a patient having sarcoidosis comprising administering an effective amount of Compound I or a pharmaceutically acceptable salt, solvate, hydrate, stereoisomer, tautomer or racemic mixtures thereof to the patient. In one embodiment, the FVC or $FEV_1$ of the patient is improved by at least 20%, at least 30%, at least 40%, at least 50%, at least 60%, at least 70%, at least 80%, at least 90%, or more.

In certain embodiments, the clinical endpoint is improvement in the chest radiographic Likert score of the patient having sarcoidosis. In some embodiments, provided herein are methods for improving or increasing the chest radiographic Likert score of a patient having sarcoidosis comprising administering an effective amount of Compound I or a pharmaceutically acceptable salt, solvate, hydrate, stereoisomer, tautomer or racemic mixtures thereof to the patient. In one embodiment, the chest radiographic Likert score is on a Likert scale of 1 to 5 (markedly worsened, worsened, unchanged, improved, and markedly improved). In one embodiment, the chest radiographic Likert score in the patient is improved by at least 1, at least 2, at least 3, or at least 4 levels.

In certain embodiments, the clinical endpoint is improvement in the Saint George's Respiratory Questionnaire score in the patient having sarcoidosis. Further provided herein are methods for improving the Saint George's Respiratory Questionnaire score of a patient having sarcoidosis comprising administering an effective amount of Compound I or a pharmaceutically acceptable salt, solvate, hydrate, stereoisomer, tautomer or racemic mixtures thereof to the patient. In one embodiment, the improvement in Saint George's Respiratory Questionnaire score is 4, 8, 12, 16, 20, 24, 28, 32, 36, 40, 44, 48, 52 points or more.

In certain embodiments, the clinical endpoint is improvement in the dyspnea index (BDI)/transition dyspnea index (TDI) in the patient having sarcoidosis. In some embodiments, provided herein are methods for improving or increasing the dyspnea index (BDI)/transition dyspnea index (TDI) of a patient having sarcoidosis comprising administering an effective amount of Compound I or a pharmaceutically acceptable salt, solvate, hydrate, stereoisomer, tautomer or racemic mixtures thereof to the patient. In one embodiment, at baseline, dyspnea is rated using five grades from 0 (severe) to 4 (unimpaired) for each of three categories (baseline functional impairment, baseline magnitude of task, and baseline magnitude of effort) to form a baseline score (0 to 12); during the transition period, the TDI assesses changes in dyspnea using seven grades ranging from −3 (major deterioration) to +3 (major improvement); and the ratings for each of the three categories are then added to form a total transition focal score (range, −9 to +9). In one embodiment, the dyspnea index (BDI)/transition dyspnea index (TDI) in the patient is improved by at least 1, at least 2, at least 3, at least 4, at least 5, at least 6, at least 7, at least 8, or 9 levels.

In one embodiment, the improvement provided herein is measured after the treatment for a period of time. In one embodiment, the treatment time is 1 week, 2 weeks, 4 weeks, 6 weeks, 12 weeks, 6 months, or a year. In one embodiment, the treatment time is 12 weeks.

In certain embodiments, the dosage of Compound I or a pharmaceutically acceptable salt, solvate, hydrate, stereoisomer, tautomer or racemic mixtures thereof is in the range of from about 0.1 mg QD to about 1 mg QD. In one embodiment, the dosage is in the range of from about 0.3 mg QD to about 0.6 mg QD. In one embodiment, the dosage is about 0.3 mg QD. In another embodiment, the dosage is about 0.6 mg QD.

7.2.4 Treatment of Other Immune-Related Diseases or Disorders

Further provided herein are methods of treating, managing, or preventing other immune-related diseases or conditions using Compound I or a pharmaceutically acceptable salt, solvate, hydrate, stereoisomer, tautomer or racemic mixtures thereof. In certain embodiments, provided herein are methods of treating, managing, or preventing other immune-related diseases or conditions using (S)-3-[4-(4-morphlin-4-ylmethylbenzyloxy)-1-oxo-1,3-dihydro-isoindo-2-yl]piperidine-2,6-dione or a pharmaceutically acceptable salt thereof. In certain embodiments, for example, provided herein is a method of treating an individual having a disease or disorder, wherein the disease or disorder is caused by, or is associated with, an inappropriate or undesirable immune response, e.g., a disease, disorder or condition that can be treated beneficially by immunosuppression, comprising administering to the individual Compound I or a pharmaceutically acceptable salt, solvate, hydrate, stereoisomer, tautomer or racemic mixtures thereof. In certain embodiments, provided herein is a method of treating an individual having a disease or disorder, wherein the disease or disorder is caused by, or is associated with, an inappropriate or undesirable immune response, e.g., a disease, disorder or condition that can be treated beneficially by immunosuppression, comprising administering to the individual (S)-3-[4-(4-morphlin-4-ylmethylbenzyloxy)-1-oxo-1,3-dihydro-isoindo-2-yl]piperidine-2,6-dione or a pharmaceutically acceptable salt thereof.

In various specific embodiments, said immune-related disease is one or more of selected from Sjögren syndrome, ANCA-induced vasculitis, anti-phospholipid syndrome, myasthenia gravis, Addison's disease, alopecia areata, ankylosing spondylitis, antiphospholipid antibody syndrome, antiphospholipid syndrome (primary or secondary), asthma, autoimmune gastritis, autoimmune hemolytic anemia, autoimmune hepatitis, autoimmune inner ear disease, autoimmune lymphoproliferative disease, autoimmune thrombocytopenic purpura, Balo disease, Behcet's disease, bullous pemphigoid, cardiomyopathy, celiac disease, Chagas disease, chronic inflammatory demyelinating polyneuropathy, cicatrical pemphigoid (e.g., mucous membrane pemphigoid), cold agglutinin disease, degos disease, dermatitis hepatiformis, essential mixed cryoglobulinemia, Goodpasture's syndrome, Graves' disease, Guillain-Barre syndrome, Hashimoto's thyroiditis (Hashimoto's disease; autoimmune thyroditis), idiopathic pulmonary fibrosis, idiopathic thrombocytopenia purpura, IgA nephropathy, juvenile arthritis, lichen planus, Meniere disease, mixed connective tissue disease, morephea, narcolepsy, neuromyotonia, pediatric autoimmune neuropsychiatric disorders (PANDAs), pemphigus vulgaris, pernicious anemia, polyarteritis nodosa, polychondritis, polymyalgia rheumatica, primary agammaglobulinemia, primary biliary cirrhosis, Raynaud disease (Raynaud phenomenon), Reiter's syndrome, relapsing polychondritis, rheumatic fever, Sjogren's syndrome, stiff-person syndrome (Moersch-Woltmann syndrome), Takayasu's arteritis, temporal arteritis (giant cell arteritis), uveitis, vasculitis (e.g., vasculitis not associated with lupus erythematosus), vitiligo, and/or Wegener's granulomatosis.

7.2.5 Treatment for Patients with Renal Impairment

In certain embodiments, provided herein are methods of treating, preventing, and/or managing a disease provided herein in patients with impaired renal function. In certain embodiments, provided herein are methods of providing appropriate dose adjustments for patients with impaired renal function due to, but not limited to, disease, aging, or other patient factors.

In certain embodiments, provided herein are methods of treating, preventing, and/or managing a disease provided herein, or a symptom thereof, in patients with impaired renal function comprising administering a therapeutically effective amount of a compound provided herein to the patient with impaired renal function. In one embodiment, provided herein are methods of treating, preventing, and/or managing relapsed disease, or a symptom thereof, in patients with impaired renal function comprising administering a therapeutically effective amount of (S)-3-(4-((4-morphlinomethyl)benzyl)oxy)-1-oxoisoindolin-2-yl)piperidine-2,6-dione or a pharmaceutically acceptable salt thereof to a patient having relapsed disease with impaired renal function.

In one embodiment, provided herein are methods of preventing a relapse in patients with impaired renal function, comprising administering an effective amount of a compound provided herein to a patient with impaired renal function at risk of having a relapse. In one embodiment, provided herein are methods of preventing a relapse in patients with impaired renal function, comprising administering an effective amount of (S)-3-(4-((4-morphlinomethyl)benzyl)oxy)-1-oxoisoindolin-2-yl)piperidine-2,6-dione or a pharmaceutically acceptable salt thereof, to a patient with impaired renal function at risk of having a relapse.

In all of the embodiments provided herein, when a renally impaired patient is treated, there is a need for administering to the renally impaired patient a dose of the compound lower than the dose administered to a normal patient (e.g., a patient without renal impairment) because of the decreased ability of the renally impaired patient in eliminating pomalidomide or its metabolites. Thus, in one embodiment, provided herein is a method for treating a renally impaired patient with a dose of a compound provided herein lower than the dose administered to a normal patient.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

7.3 Dosages and Dosing Amounts

The dose of Compound I or a pharmaceutically acceptable salt, solvate, hydrate, stereoisomer, tautomer or racemic mixtures thereof to be administered to a patient is rather widely variable and can be subject to the judgment of a health-care practitioner. Doses of Compound I or a pharmaceutically acceptable salt, solvate, hydrate, stereoisomer, tautomer or racemic mixtures thereof vary depending on factors such as: specific indication to be treated, prevented, or managed; age and condition of a patient; and amount of second active agent used, if any. In general, Compound I or a pharmaceutically acceptable salt, solvate, hydrate, stereoisomer, tautomer or racemic mixtures thereof can be administered one to four or more times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight.

In one embodiment, one dose is given per day. In any given case, the amount of Compound I or a pharmaceutically acceptable salt, solvate, hydrate, stereoisomer, tautomer or racemic mixtures thereof administered will depend on such factors as the solubility of the active component, the formulation used and the route of administration. In one embodiment, application of a topical concentration provides intracellular exposures or concentrations of about 0.01-10 µM.

In certain embodiments, Compound I or a pharmaceutically acceptable salt, solvate, hydrate, stereoisomer, tautomer or racemic mixtures thereof is used in an amount of from about 0.1 mg to about 1000 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In other embodiments, the dose can be from about 0.1 mg to about 100 mg, from about 0.1 mg to about 50 mg, from about 0.1 mg to about 25 mg, from about 0.1 mg to about 20 mg, from about 0.1 mg to about 15 mg, from about 0.1 mg to about 10 mg, from about 0.1 mg to about 7.5 mg, from about 0.1 mg to about 5 mg, from about 0.1 mg to about 4 mg, from about 0.1 mg to about 3 mg, from about 0.1 mg to about 2 mg, or from about 1 mg to about 1 mg.

7.4 Combination Therapy

Compound I or a pharmaceutically acceptable salt, solvate, hydrate, stereoisomer, tautomer or racemic mixtures thereof can be combined with other pharmacologically active compounds ("second active agents") in methods and compositions provided herein. Certain combinations may work synergistically in the treatment of particular types diseases or disorders, and conditions and symptoms associated with such diseases or disorders. Compound I or a pharmaceutically acceptable salt, solvate, hydrate, stereoisomer, tautomer or racemic mixtures thereof can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

In another embodiment, the method of treatment provided herein comprises the administration of a second therapeutic agent, wherein the second therapeutic agent is an anti-inflammatory drug, e.g., a steroidal anti-inflammatory drug, or a non-steroidal anti-inflammatory drug (NSAID), acetaminophen, naproxen, ibuprofen, acetylsalicylic acid, and the like. In a more specific embodiment in which an NSAID is administered, a proton pump inhibitor (PPI), e.g., omeprazole may also administered. In one embodiment, the anti-inflammatory agent is a corticosteroid. In another embodiment, the antiinflammatory agent is colchicine.

In another embodiment, the second therapeutic agent is an immunomodulatory compound or an immunosuppressant compound such as azathioprine (Imuran™, Azasan™), methotrexate (Rheumatrex™, Trexall™), penicillamine (Depen™, Cuprimine™), cyclophosphamide (Cytoxan™), mycophenalate (CellCept™, Myfortic™), bosentan (Tracleer®), prednisone (Deltasone™, Liquid Pred™), and a PDE5 inhibitor. In another embodiment, where the affected individual has digital ulcerations and pulmonary hypertension, a vasodilator such as prostacyclin (iloprost) may be administered.

In another embodiment, the second therapeutic agent is an HDAC inhibitor, such as romidepsin, vorinostat, panobinostat, valproic acid, or belinostat; or a biological agent, such as an interleukin, an immunomodulatory monoclonal antibody, or bacillus Calmette-Guerin (BCG).

In another embodiment, the second therapeutic agent is an inhibitor of ActRII receptors or an activin-ActRII inhibitor. Inhibitors of ActRII receptors include ActRIIA inhibitors and ActRIIB inhibitors. Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker.

An exemplary activin-binding ActRIIA polypeptide fused to a human Fe domain is provided in SEQ ID NO: 1.

```
                                                  SEQ ID NO: 1
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPPTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK
```

An exemplary fusion protein comprising a soluble extracellular domain of ActRIIB fused to an Fe domain is provided in SEQ ID NO: 2.

```
                                                  SEQ ID NO: 2
ETRECIYYNANWELERTNQSGLERCEGEQDKRLHCYASWRNSSGTIELVK

KGCWDDDFNCYDRQECVATEENPQVYFCCCEGNFCNERFTHLPEAGGPEV

TYEPPPTGGGTHTCPPCPAPELLGGPSVFLFPPKPKDTLMISRTPEVTCV

VVDVSHEDPEVKFNWYVDGVEVHNAKTKPREEQYNSTYRVVSVLTVLHQD

WLNGKEYKCKVSNKALPAPIEKTISKAKGQPREPQVYTLPPSREEMTKNQ

VSLTCLVKGFYPSDIAVEWESNGQPENNYKTTPPVLDSDGSFFLYSKLTV

DKSRWQQGNVFSCSVMHEALHNHYTQKSLSLSPGK
```

Further examples of non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety.

In one embodiment, the inhibitor of ActRII receptors is ACE-11. In another embodiment, the inhibitor of ActRII receptors is ACE-536.

Any combination of the above therapeutic agents, suitable for treatment of the diseases or symptoms thereof, can be administered. Such therapeutic agents can be administered in any combination with Compound I or a pharmaceutically acceptable salt, solvate, hydrate, stereoisomer, tautomer or racemic mixtures thereof, at the same time or as a separate course of treatment.

7.5 Cycling Therapy

In certain embodiments, Compound I or a pharmaceutically acceptable salt, solvate, hydrate, stereoisomer, tautomer or racemic mixtures thereof provided herein is cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.03 mg to about 10 mg per day, followed by a rest of one or two weeks. In other embodiments, the dose can be from about 0.1 mg to about 8 mg, from about 0.3 mg to about 6 mg, from about 1 mg to about 4 mg, or about 2 mg, followed by a rest.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

7.6 Biomarkers

In certain embodiments, provided herein are biomarkers for the treatment of various disease or disorders provided herein. In one embodiment, the biomarker is cluster of differentiation-44 ("CD44"), a molecule found on the surface of B cells. In another embodiment, the biomarker is cluster of differentiation-83 ("CD83"), a molecule found on the surface of B cells. In other embodiments, the biomarker is a combination of CD44 and CD83.

The levels of the protein biomarkers provided herein can be detected or quantitated by any methods known in the art. In certain embodiments, antibody-based methods are used. In certain embodiments, the detecting or quantitating method is immunoblotting (western blot), an enzyme-linked immunosorbent assay (ELISA), immunohistochemistry, flow cytometry, a cytometric bead array, or mass spectroscopy.

In certain embodiments, the detecting or quantitating method is immunoblotting (western blot). In certain embodiments, the detecting or quantitating method is an enzyme-linked immunosorbent assay (ELISA). In certain embodiments, the detecting or quantitating method is a direct ELISA. In certain embodiments, the detecting or quantitating method is an indirect ELISA. In certain embodiments, the detecting or quantitating method is an sandwich ELISA. In certain embodiments, the detecting or quantitating method is immunohistochemistry. In certain embodiments, the detecting or quantitating method is flow cytometry. In certain embodiments, the detecting or quantitating method is a cytometric bead array. In certain embodiments, the detecting or quantitating method is mass spectroscopy.

Certain embodiments include methods of identifying a subject who is likely to be responsive to a treatment of a disease, disorder, or condition with a treatment compound. In certain embodiments the method involves determining the level of a biomarker in a biological sample from the subject. In certain embodiments the biomarker is CD44. In certain embodiments the biomarker is CD83.

In certain embodiments methods of identifying a subject who is likely to be responsive to a treatment of a disease, disorder, or condition with a treatment compound, comprise: a) determining the level of a biomarker in a biological sample from the subject, wherein the biomarker is CD44, CD83 or combination thereof, and b) comparing the level of the biomarker in the biological sample from the subject to a reference level of the biomarker; wherein the subject is likely to be responsive to the treatment if the level of the biomarker in the biological sample from the subject is altered as compared to the reference level of the biomarker.

In certain embodiments methods of identifying a subject who is likely to be responsive to a treatment of a disease, disorder, or condition with a treatment compound, comprise: a) determining the level of a biomarker in a biological sample from the subject, wherein the biomarker is CD44, CD83 or combination thereof, b) determining the level of the biomarker in a control sample; and c) comparing the level of the biomarker in the biological sample from the subject to the level of the biomarker in the control sample; wherein the subject is likely to be responsive to the treatment if the level of the biomarker in the biological sample from the subject is altered as compared to the level of the biomarker in the control sample.

In certain embodiments methods of identifying a subject who is likely to be responsive to a treatment of a disease, disorder, or condition with a treatment compound, comprise: a) determining the level of a biomarker in a biological sample from the subject, wherein the biomarker is CD83; and b) comparing the level of the biomarker in the biological sample from the subject to a reference level of the biomarker; wherein the subject is likely to be responsive to the treatment if the level of the biomarker in the biological sample from the subject is higher than the reference level of the biomarker.

In certain embodiments methods of identifying a subject who is likely to be responsive to a treatment of a disease, disorder, or condition with a treatment compound, comprise: a) determining the level of a biomarker in a biological sample from the subject, wherein the biomarker is CD83; b) determining the level of the biomarker in a control sample; and c) comparing the level of the biomarker in the biological sample from the subject to the level of the biomarker in the control sample; wherein the subject is likely to be responsive to the treatment if the level of the biomarker in the biological sample from the subject is higher than the level of the biomarker in the control sample.

In certain embodiments methods of identifying a subject who is likely to be responsive to a treatment of a disease, disorder, or condition with a treatment compound, comprise: a) determining the level of a biomarker in a biological sample from the subject, wherein the biomarker is CD44; and b) comparing the level of the biomarker in the biological sample from the subject to a reference level of the biomarker; wherein the subject is likely to be responsive to the treatment if the level of the biomarker in the biological sample from the subject is lower than the reference level of the biomarker.

In certain embodiments methods of identifying a subject who is likely to be responsive to a treatment of a disease, disorder, or condition with a treatment compound, comprise: a) determining the level of a biomarker in a biological sample from the subject, wherein the biomarker is CD44; b) determining the level of the biomarker in a control sample; and c) comparing the level of the biomarker in the biological sample from the subject to the level of the biomarker in the control sample; wherein the subject is likely to be responsive to the treatment if the level of the biomarker in the biological sample from the subject is lower than the level of the biomarker in the control sample.

In certain embodiments methods of predicting the responsiveness of a subject to a treatment of a disease, disorder, or condition with a treatment compound, comprise: a) determining the level of a biomarker in a biological sample from the subject, wherein the biomarker is CD44, CD83 or combination thereof, and b) comparing the level of the biomarker in the biological sample to a reference level of the biomarker; wherein the difference between the level of the biomarker in the biological sample from the subject and the reference level of the biomarker correlates with the responsiveness of the subject to the treatment.

In certain embodiments methods of predicting the responsiveness of a subject to a treatment of a disease, disorder, or condition with a treatment compound, comprise: a) determining the level of a biomarker in a biological sample from the subject, wherein the biomarker is CD44, CD83 or combination thereof, b) determining the level of the biomarker in a control sample; and c) comparing the level of the biomarker in the biological sample from the subject to the level of the biomarker in the control sample; wherein the difference between the level of the biomarker in the biological sample from the subject and the level of the biomarker in the control sample correlates with the responsiveness of the subject to the treatment.

In certain embodiments methods of predicting the responsiveness of a subject to a treatment of a disease, disorder, or condition with a treatment compound, comprise: a) determining the level of a biomarker in a biological sample from the subject, wherein the biomarker is CD83; and b) comparing the level of the biomarker in the biological sample to a reference level of the biomarker, wherein an increased level of the biomarker in the biological sample from the subject in comparison with the reference level of the biomarker correlates with an increased responsiveness of the subject to the treatment.

In certain embodiments methods of predicting the responsiveness of a subject to a treatment of a disease, disorder, or condition with a treatment compound, comprise: a) determining the level of a biomarker in a biological sample from the subject, wherein the biomarker is CD83; b) determining the level of the biomarker in a control sample; and c) comparing the level of the biomarker in the biological sample from the subject to the level of the biomarker in the control sample; wherein an increased level of the biomarker in the biological sample from the subject in comparison with the level of the biomarker in the control sample correlates with an increased responsiveness of the subject to the treatment.

In certain embodiments methods of predicting the responsiveness of a subject to a treatment of a disease, disorder, or condition with a treatment compound, comprise: a) determining the level of a biomarker in a biological sample from the subject, wherein the biomarker is CD44; and b) comparing the level of the biomarker in the biological sample to a reference level of the biomarker, wherein a decreased level of the biomarker in the biological sample from the subject in comparison with the reference level of the biomarker correlates with an increased responsiveness of the subject to the treatment.

In certain embodiments methods of predicting the responsiveness of a subject to a treatment of a disease, disorder, or condition with a treatment compound, comprise: a) determining the level of a biomarker in a biological sample from the subject, wherein the biomarker is CD44; b) determining the level of the biomarker in a control sample; and c) comparing the level of the biomarker in the biological sample from the subject to the level of the biomarker in the control sample; wherein a decreased level of the biomarker in the biological sample from the subject in comparison with the level of the biomarker in the control sample correlates with an increased responsiveness of the subject to the treatment.

In certain embodiments methods of monitoring the efficacy of a treatment of a disease, disorder, or condition in a subject treated with a treatment compound, comprise: a) obtaining a first biological sample from the subject; b) determining the level of a biomarker in the first biological sample, wherein the biomarker is CD 44, CD83 or combination thereof; c) administering the treatment compound to the subject; d) thereafter obtaining a second biological sample from the subject; e) determining the level of the biomarker in the second biological sample; and f) comparing the levels of the biomarker in the first and second biological samples; wherein the subject is responsive to the treatment if the level of the biomarker in the second biological sample of the subject is altered as compared to the level of the biomarker in the first biological sample of the subject.

In certain embodiments methods of monitoring the efficacy of a treatment of a disease, disorder, or condition in a subject treated with a treatment compound, comprise: a) obtaining a first biological sample from the subject; b) determining the level of a biomarker in the first biological sample, wherein the biomarker is CD83; c) administering the treatment compound to the subject; d) thereafter obtaining a second biological sample from the subject; e) determining the level of the biomarker in the second biological sample, and f) comparing the levels of the biomarker in the first and second biological samples; wherein the subject is responsive to the treatment if the level of the biomarker in the second biological sample of the subject is higher than the level of the biomarker in the first biological sample of the subject.

In certain embodiments methods of monitoring the efficacy of a treatment of a disease, disorder, or condition in a subject treated with a treatment compound, comprise: a) obtaining a first biological sample from the subject; b) determining the level of a biomarker in the first biological sample, wherein the biomarker is CD44; c) administering the treatment compound to the subject; d) thereafter obtaining a second biological sample from the subject; e) determining the level of the biomarker in the second biological sample, and f) comparing the levels of the biomarker in the first and second biological samples; wherein the subject is responsive to the treatment if the level of the biomarker in the second biological sample of the subject is lower than the level of the biomarker in the first biological sample of the subject.

In certain embodiments methods of monitoring the compliance of a subject with a treatment of a disease, disorder, or condition with a treatment compound, comprise: a) obtaining a biological sample from the subject; b) determining the level of a biomarker in the biological sample, wherein the biomarker is CD44, CD83 or combination thereof, and c) comparing the level of the biomarker with the level of the biomarker in a control untreated sample from the subject; wherein the change in the level of the biomarker in the biological sample in comparison with the level of the biomarker in the control sample indicates the compliance of the subject with the treatment.

In certain embodiments methods of monitoring the compliance of a subject with a treatment of a disease, disorder, or condition with a treatment compound, comprise: a) obtaining a biological sample from the subject; b) determining the level of a biomarker in the biological sample, wherein the biomarker is CD83; and c) comparing the level of the biomarker with the level of the biomarker in a control untreated sample from the subject; wherein an increased level of the biomarker in the biological sample in comparison with the level of the biomarker in the control sample indicates the compliance of the subject with the treatment.

In certain embodiments methods of monitoring the compliance of a subject with a treatment of a disease, disorder, or condition with a treatment compound, comprise: a) obtaining a biological sample from the subject; b) determining the level of a biomarker in the biological sample, wherein the biomarker is CD44; and c) comparing the level of the biomarker with the level of the biomarker in a control untreated sample from the subject; wherein a decreased level of the biomarker in the biological sample in comparison with the level of the biomarker in the control sample indicates the compliance of the subject with the treatment.

In certain embodiments the treatment compound is an immunomodulatory compound. In certain embodiments the treatment compound is 3-[4-(4-morpholin-4-ylmethyl-benzyloxy)-1-oxo-1,3-dihydro-isoindol-2-yl]-piperidine-2,6-dione hydrochloride, or a pharmaceutically acceptable salt, solvate, hydrate, stereoisomer, tautomer or racemic mixtures thereof. In one embodiment, the compound is (S)-3-[4-(4-morpholin-4-ylmethyl-benzyloxy)-1-oxo-1,3-dihydro-isoindol-2-yl]-piperidine-2,6-dione, or a pharmaceutically acceptable salt, solvate, or hydrate thereof.

7.7 Pharmaceutical Compositions and Dosage Forms

Pharmaceutical compositions can be used in the preparation of individual, single unit dosage forms. Pharmaceutical compositions and dosage forms provided herein comprise a compound provided herein, or a pharmaceutically acceptable salt, solvate, hydrate, stereoisomer, racemate, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences,* $20^{th}$ ed., Mack Publishing, Easton Pa. (2000).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles &Practice,* 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

7.7.1 Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 20th ed., Mack Publishing, Easton Pa. (2000).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

7.7.2 Controlled Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus, the compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

7.7.3 Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

7.7.4 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th, 18th and 20th eds., Mack Publishing, Easton Pa. (1980, 1990 and 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th, 18th and 20th eds., Mack Publishing, Easton Pa. (1980, 1990 and 2000).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, hydrates, prodrugs, clathrates, or stereoisomers of the active ingredients can be used to further adjust the properties of the resulting composition.

7.7.5 Kits

In one embodiment, active ingredients provided herein are not administered to a patient at the same time or by the same route of administration. In another embodiment, provided are kits which can simplify the administration of appropriate amounts of active ingredients.

In one embodiment, a kit comprises a dosage form of a compound provided herein. Kits can further comprise additional active ingredients such as other anti-inflammatory, immunomodulatory or immunosuppressant compounds, or a combination thereof. Examples of the additional active ingredients include, but are not limited to, those disclosed herein.

In other embodiments, kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

8. EXAMPLES

The following Examples are presented by way of illustration, not limitation. In the examples, test compound refers to (S)-3-[4-(4-morphlin-4-ylmethylbenzyloxy)-1-oxo-1,3-dihydro-isoindo-2-yl]piperidine-2,6-dione.

8.1 Example 1: Preparation of (S)-3-[4-(4-Morphlin-4-Ylmethylbenzyloxy)-1-Oxo-1,3-Dihydro-Isoindo-2-Yl]Piperidine-2,6-Dione Hydrochloride

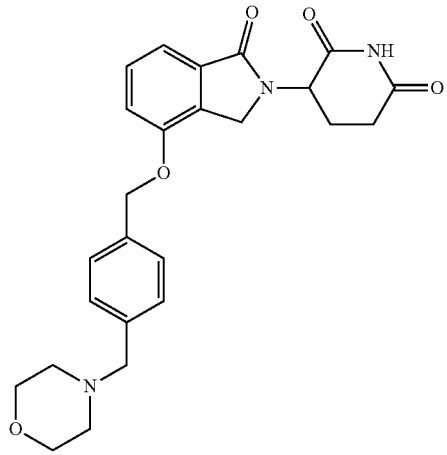 [SMILES: O=C1CCC(N2Cc3c(OCc4ccc(CN5CCOCC5)cc4)cccc3C2=O)C(=O)N1]

8.1.1 3-Hydroxy-2-Methyl-Benzoic Acid Methyl Ester

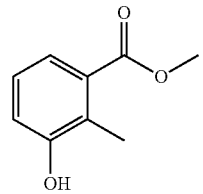

3-Hydroxy-2-methylbenzoic acid (105 g, 690 mmol) was added to MeOH (800 mL) in a 2 L three neck round bottom flask equipped with condenser, thermometer and stirring bar followed by the addition of MeOH (250 ml). $H_2SO_4$ (10 mL, 180 mmol) was added to above solution. The reaction mixture was stirred at 62° C. for 17 hours. The solvent was removed in vacuo. The residue (200 mL) was added to water (600 mL) slowly at room temperature and a white solid was formed. The suspension was stirred in an ice bath for 30 minutes and filtered. The solid was washed with water (5×250 mL) and dried to give 3-hydroxy-2-methyl-benzoic acid methyl ester as a white solid (100 g, 87% yield). The compound was used in the next step without further purification: LCMS MH=167; $^1$H NMR (DMSO-d$_6$) δ 2.28 (s, 3H, CH$_3$), 3.80 (s, 3H, CH$_3$), 6.96-7.03 (m, 1H, Ar), 7.09 (t, J=7.8 Hz, 1H, Ar), 7.14-7.24 (m, 1H, Ar), 9.71 (s, 1H, OH).

8.1.2 3-(Tert-Butyl-Dimethyl-Silanyloxy)-2-Methyl-Benzoic Acid Methyl Ester

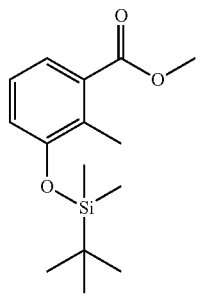 [SMILES: COC(=O)c1cccc(O[Si](C)(C)C(C)(C)C)c1C]

To a 1 L three neck RB flask equipped with stirring bar and thermometer, were added DMF (300 mL), methyl 3-hydroxy-2-methylbenzoate (90 g, 542 mmol) and imidazole (92 g, 1,354 mmol). TBDMS-Cl (90 g, 596 mmol) was added to the above solution in portions to control the internal temp between 15-19° C. over 20 minutes, and after addition, the internal temp dropped below 1° C. The ice bath was removed and the reaction mixture was stirred at room temperature for 16 hours. The reaction mixture was added to ice water (500 mL), and the resulting solution was divided into two portions (700 mL×2). Each portion was extracted with EtOAc (700 mL). Each organic layer was washed with cold water (350 mL) and brine (350 mL). Organic layers were combined and dried by MgSO$_4$. The combined organic layer was concentrated to give 3-(tert-butyl-dimethyl-silanyloxy)-2-methyl-benzoic acid methyl ester as a light brown oil (160 g, 100% crude yield). The compound was used in the next step without further purification: LCMS MH=281; $^1$H NMR (DMSO-d$_6$) δ −0.21 (s, 6H, CH$_3$, CH$_3$), 0.73-0.84 (m, 9H, CH$_3$, CH$_3$, CH$_3$), 2.10 (s, 3H, CH$_3$), 3.60 (s, 3H, CH$_3$), 6.82 (dd, 1H, Ar), 6.97 (t, J=7.9 Hz, 1H, Ar), 7.13 (dd, J=1.1, 7.7 Hz, 1H, Ar).

8.1.3 2-Bromomethyl-3-(Tert-Butyl-Dimethyl-Silanyloxy)-Benzoic Acid Methyl Ester

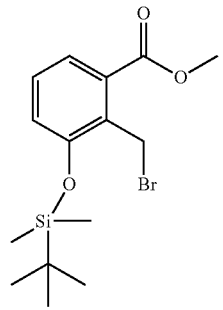 [SMILES: COC(=O)c1cccc(O[Si](C)(C)C(C)(C)C)c1CBr]

NBS (49.8 g, 280 mmol) was added to methyl 3-(tert-butyl dimethylsilyloxy)-2-methylbenzoate (78.4 g, 280 mmol) in methyl acetate (500 mL) at room temperature to give an orange colored suspension. The resulting reaction mixture was heated in an oil bath at 40° C. and shined by 300 wt sunlight bulb at reflux for 4 hours. The reaction mixture was cooled down and washed by Na$_2$SO$_3$ solution (2×600 mL, 50% saturated concentration), water (500 mL) and brine (600 mL). The organic layer was dried by MgSO$_4$ and decolorized by charcoal. The organic layer was concentrated to give 2-bromomethyl-3-(tert-butyl-dimethyl-silanyloxy)-benzoic acid methyl ester as a light brown oil (96 g, 91% crude yield). The compound was used in the next step without further purification: LCMS M-Br=279; $^1$H NMR (DMSO-d$_6$) δ 0.05-0.11 (m, 6H, CH$_3$, CH$_3$), 0.82 (s, 9H, CH$_3$, CH$_3$, CH$_3$), 3.65 (s, 3H, CH$_3$), 4.74 (s, 2H, CH$_2$), 6.94 (dd, J=1.3, 8.1 Hz, 1H, Ar), 7.10-7.20 (m, 1H, Ar), 7.21-7.29 (m, 1H, Ar).

8.1.4 4-Carbamoyl-Butyric Acid Methyl Ester

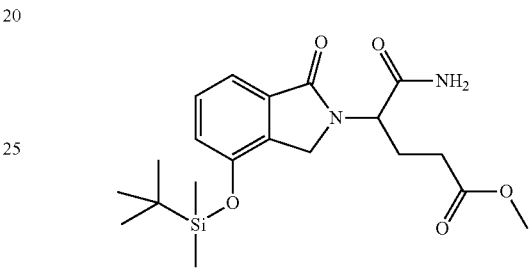

To a stirred solution of methyl 2-(bromomethyl)-3-(tert-butyldimethylsilyloxy)benzoate (137.5 g, 325 mmol) in acetonitrile (1100 mL) in a 2 L round bottom flask, was added methyl 4,5-diamino-5-oxopentanoate hydrochloride (70.4 g, 358 mmol). To the suspension was added DIPEA (119 ml, 683 mmol) through an addition funnel over 10 minutes and the suspension was stirred at room temperature for 1 hour before the mixture was heated in an oil bath at 40° C. for 23 hours. The reaction mixture was concentrated under vacuo. The residue was stirred in ether (600 mL), and a white solid precipitated out. The mixture was filtered and the solid was washed with ether (400 mL). The filtrate was washed with HCl (1N, 200 mL), NaHCO$_3$ (sat. 200 mL) and brine (250 mL). The aqueous acid layer and basic layer were kept separately. Then the solid was further washed with ether (250 mL) and the liquid was washed with above acid solution and basic solution. The two organic layers were combined and concentrated under vacuo to give 4-[4-(tert-Butyl-dimethyl-silanyloxy)-1-oxo-1,3-dihydro-isoindol-2-yl]-4-carbamoyl-butyric acid methyl ester as a brown oil (152 g, 115% crude yield, 77% purity by H NMR). The compound was used in the next step without further purification: LCMS MH=407.

8.1.5 4-Carbamoyl-4-(4-Hydroxy-1-Oxo-1,3-Dihydro-Isoindol-2-Yl)-Butyric Acid Methyl Ester

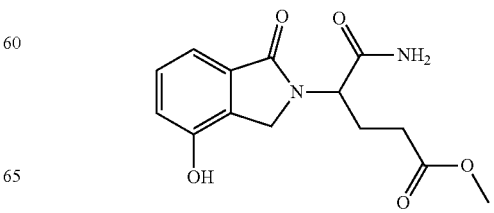

To a stirred cold solution of methyl 5-amino-4-(4-(tert-butyldimethylsilyloxy)-1-oxoisoindolin-2-yl)-5-oxopentanoate (152 g, 288 mmol) in DMF (500 mL) and water (55 mL), was added by K$_2$CO$_3$ (19.89 g, 144 mmol) by portions over 5 minutes. The resulting reaction mixture was stirred at room temperature for 40 minutes. The reaction mixture was cooled in an ice bath. To the mixture, HCl (12M, 23.99 ml, 288 mmol) was added slowly. After the addition, acetonitrile (280 mL) was added to the mixture and a solid precipitated out. The mixture was stirred at room temperature for 10 minutes and filtered. The solid was washed with acetonitrile (50 mL×4). The filtrate was concentrated under high vacuo to give a yellow oil (168 g). The oil was dissolved in acetonitrile (600 mL) and stirred at room temperature for 10 minutes. The mixture was filtered and the solid was washed with acetonitrile (25 mL×2). The filtrate was concentrated under high vacuo to give a yellow oil (169 g), which was added to a mixture of water (1200 mL) and ether (1000 mL). The mixture was stirred for 3 minutes and the layers were separated. The aqueous solution was concentrated under high vacuo and the residue was stirred in acetonitrile (160 mL) and a white solid was formed after overnight stirring. The mixture was filtered to give 4-carbamoyl-4-(4-hydroxy-1-oxo-1,3-dihydro-isoindol-2-yl)-butyric acid methyl ester as a white solid (46 g, 54% yield). The filtrate was concentrated and the residue was further crystallized in acetonitrile (60 mL) to give more 4-carbamoyl-4-(4-hydroxy-1-oxo-1,3-dihydro-isoindol-2-yl)-butyric acid methyl ester as a white solid (11.7 g, 14% yield). The filtrate was concentrated and the residue was purified by ISCO chromatography to give more 4-carbamoyl-4-(4-hydroxy-1-oxo-1,3-dihydro-isoindol-2-yl)-butyric acid methyl ester as a white solid (13.2 g, 15% yield). The total product obtained was 70.9 g in 83% yield: LCMS MH=293; $^1$H NMR (DMSO-d$_6$) δ 1.95-2.34 (m, 4H, CH$_2$, CH$_2$), 3.51 (s, 3H, CH$_3$), 4.32 (d, J=17.6 Hz, 1H, CHH), 4.49 (d, J=17.4 Hz, 1H, CHH), 4.73 (dd, J=4.7, 10.2 Hz, 1H, CHH), 6.99 (dd, J=0.8, 7.9 Hz, 1H, Ar), 7.10-7.23 (m, 2H, Ar, NHH), 7.25-7.38 (m, 1H, Ar), 7.58 (s, 1H, NHH), 10.04 (s, 1H, OH).

8.1.6 3-(4-((4-(Morpholinomethyl)Benzyl)Oxy)-1-Oxoisoindolin-2-Yl)Piperidine-2,6-Dione

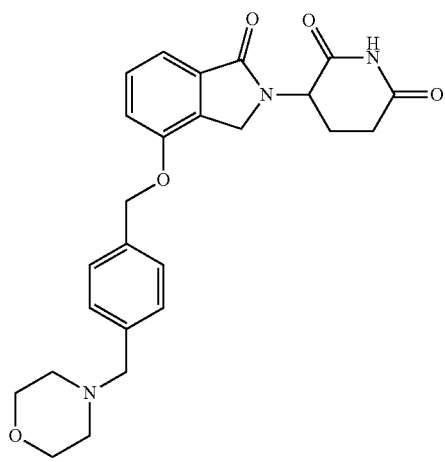 [SMILES: O=C1CCC(N2Cc3c(OCc4ccc(CN5CCOCC5)cc4)cccc3C2=O)C(=O)N1]

Step 1: To the solution of 3-(4-hydroxy-1-oxo-1,3-dihydro-isoindol-2-yl)-piperidine-2,6-dione (2.5 g, 8.56 mmol) in THF (60 mL) was added triphenyl phosphine (polymer supported 1.6 mmol/g, 12 g, 18.8 mmol). The mixture was stirred at room temperature for 15 minutes. Diisopropyl azodicarboxylate (3.96 mL, 18.8 mmol) was added at 0° C., and the mixture was stirred at 0° C. for 30 minutes. (4-Morpholin-4-ylmethyl-phenyl)-methanol (2.62 g, 12.4 mmol) was added at 0° C., and the mixture was allowed to warm to room temperature and stirred at room temperature overnight. The reaction mixture was filtered, and the filtrate was concentrated. The resulting oil was purified on silica gel column eluted with methylene chloride and methanol (gradient, product came out at 6% methanol) to give 4-carbamoyl-4-[4-(4-morpholin-4-ylmethyl-benzyloxy)-1-oxo-1,3-dihydro-isoindol-2-yl]-butyric acid methyl ester (2.2 g, 54% yield). The product was used in the next step without further purification.

Step 2: To the TH solution (50 mL) of 4-carbamoyl-4-[4-(4-morpholin-4-ylmethyl-benzyloxy)-1-oxo-1,3-dihydro-isoindol-2-yl]-butyric acid methyl ester (2.2 g, 4.57 mmol) was added potassium tert-butoxide (0.51 g, 4.57 mmol) at 0° C. The mixture was stirred at 0° C. for 10 minutes and was quenched with 1N HCl (5 mL, 5 mmol) followed by saturated NaHCO$_3$ (25 mL). The mixture was extracted with EtOAc (2×50 mL). The organic layer was washed with water (30 mL), brine (30 mL), dried over MgSO$_4$ and concentrated. To the resulting solid was added EtOAc (10 mL) followed by hexane (10 mL) under stirring. The suspension was filtered to give 3-(4-((4-(morpholinomethyl)benzyl)oxy)-1-oxoisoindolin-2-yl)piperidine-2,6-dione as white solid (1.5 g, 73% yield). HPLC: Waters Symmetry C$_{18}$, 5 μm, 3.9×150 mm, 1 mL/min, 240 nm, gradient to 95/5 acetonitrile/0.1% H$_3$PO$_4$ in 5 min: t$_R$=4.78 min (97.5%); mp: 210-212° C.; $^1$H NMR (DMSO-d$_6$) δ 1.86-2.09 (m, 1H, CHH), 2.29-2.38 (m, 4H, CH$_2$, CH$_2$), 2.44 (dd, J=4.3, 13.0 Hz, 1H, CHH), 2.53-2.64 (m, 1H, CHH), 2.82-2.99 (m, 1H, CHH), 3.46 (s, 2H, CH$_2$), 3.52-3.61 (m, 4H, CH$_2$, CH$_2$), 4.18-4.51 (m, 2H, CH$_2$), 5.11 (dd, J=5.0, 13.3 Hz, 1H, NCH), 5.22 (s, 2H, CH$_2$), 7.27-7.38 (m, 5H, Ar), 7.40-7.53 (m, 3H, Ar), 10.98 (s, 1H, NH) $^{13}$C NMR (DMSO-d$_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for C$_{25}$H$_{27}$N$_3$O$_5$+0.86 H$_2$O: C, 64.58; H, 6.23; N, 9.04; Found: C, 64.77; H, 6.24; N, 8.88.

(S)-3-(4-((4-(morpholinomethyl)benzyl)oxy)-1-oxoisoindolin-2-yl)piperidine-2,6-dione and (R)-3-(4-((4-(morpholinomethyl)benzyl)oxy)-1-oxoisoindolin-2-yl)piperidine-2,6-dione were prepared from 3-(4-((4-(morpholinomethyl)benzyl)oxy)-1-oxoisoindolin-2-yl)piperidine-2,6-dione through chiral separation.

8.2 Example 2: Effect on the Expression of Transcription Factors in Primary Human B Cell Differentiation Model In this example, the effect of (S)-3-[4-(4-morphlin-4-ylmethylbenzyloxy)-1-oxo-1,3-dihydro-isoindo-2-yl]piperidine-2,6-dione (test compound) on the expression of transcription factors controlling plasma cell differentiation, and immunoglobulin production, using an in vitro human B-cell differentiation culture system.

The following abbreviations are used in this example:

| Abbreviation or Specialist Term | Explanation or Definition |
| --- | --- |
| BCL6 | B-cell lymphoma 6 protein |
| BLIMP-1 | B-lymphocyte-induced maturation protein 1 |
| EtOH | Ethanol |
| FBS | Fetal bovine serum |
| DMSO | Dimethyl sulfoxide |
| IRF-4 | Interferon regulatory factor 4 |
| MFI | Mean fluorescence intensity |
| PAX5 | Paired box protein Pax-5 |
| SLE | Systemic lupus erythematosus |
| XBP-1 | X-box binding protein 1 |

50 ml Buffy coat from healthy donors were obtained from Blood Center of New Jersey. SLE Lupus PBMC samples were obtained from Conversant Bio (Huntsville, Ala. 35806).

The following cell culture reagents were used in this study.

| ITEM | Source |
| --- | --- |
| Iscoves Modified Dulbecco medium | Invitrogen |
| Fetal Bovine Serum | Lonza |
| Human Insulin | Sigma |
| Human Transferrin | Sigma |
| penicillin/ streptomycin | Lonza |
| Recombinant Human IL-2 | R & D Systems |
| Recombinant Human IL-6 | R & D Systems |
| Recombinant Human IL-10 | R & D Systems |
| Recombinant Human IL-15 | R & D Systems |
| CD40 Ligand/TNFSF5/ histidine-tagged | R & D Systems |
| polyHistidine mouse IgG1 antibody | R & D Systems |
| ODN 2006-Human TLR9 ligand | Invivogen |
| Human Interferon ALPHA A | PB interferon source |

The following were used in flow cytometry analysis.

| ITEM | Source |
| --- | --- |
| FITC anti-human CD19 | IBD Pharmigen |
| FITC anti-human CD20 | IBD Pharmigen |
| PE anti-human CD27 | IBD Pharmigen |
| PE anti-human CD38 | IBD Pharmigen |
| APC anti-human CD38 | IBD Pharmigen |
| FITC anti-mouse IgG1k Isotype | IBD Pharmigen |
| PE anti-mouse IgG1k Isotype | IBD Pharmigen |
| FITC anti-mouse IgG2bk Isotype | IBD Pharmigen |
| APC anti-mouse IgG1k Isotype | IBD Pharmigen |
| Stain Buffer | IBD Pharmigen |

The following gene primers were used for RT-PCR:

| ITEM | Source |
| --- | --- |
| AICDA gene expression assay | Applied Biosystem |
| BCL6 gene expression assay | Applied Biosystem |
| GAPDH gene expression assay | Applied Biosystem |
| IGJ gene expression assay | Applied Biosystem |
| IRF4 gene expression assay | Applied Biosystem |
| PAX5 gene expression assay | Applied Biosystem |
| PRDM1 gene expression assay | Applied Biosystem |
| XBP1 gene expression assay | Applied Biosystem |
| Reverse Transcription Kit | Applied Biosystem |
| Master Mix | Applied Biosystem |

8.2.1 Purification of hPBMCs

Fifty ml human buffy coat was aliquoted 25 ml each into two 50 ml conical tubes and 25 ml sterile HBSS was added to each conical tube. The tubes were gently mixed by inverting. Fifteen ml of room temperature Ficoll-Paque Plus (GE Healthcare; cat #17-1440-02) was aliquoted into four 50 ml conical tubes. Then 25 ml of the Buffy coat/HBSS mixture was layered gently and slowly on top of the Ficoll. The samples were centrifuged at 450 rpm for 35 minutes. The top layered containing plasma was pipetted off and discarded. The interface containing mononuclear cells was transferred into two 50 ml conical tubes. Both conical tubes were filled to total volume of 50 ml with HBSS and centrifuged at 1200 rpm for 10 minutes. The cells were washed again in HBSS and spun at 1000 rpm for 10 minutes. Cell pellet was resuspended with 20 mL of B cell media (Iscoves+10% PFBS, 1% P/S, and 5 µg/mL human insulin and counted on the cell counter.

8.2.2 B Cell Enrichment CD19+

Purified PBMCs were counted and aliquoted at $2 \times 10^8$ cells per tube. The cells were centrifuged at 1200 rpm for 5 minutes and then supernatants were discarded. The cells were resuspended in 4 mL of Robosep Buffer (Stemcell Technologies catalog #20104) and transferred to a 14 mL polystyrene round bottom tube (BD catalog #352057) and mixed well. Then 200 µL of EasySep Human B cell enrichment cocktail was added (StemCell Technologies catalog #19054). Samples were vortexed and incubated at room temperature for 10 minutes. Next 300 µL of EasySep Magnetic particles (vortexed) (StemCell Technologies catalog #19054) were added to the tube. Samples were vortexed and incubated at room temperature for 5 minutes. After the 5 minute incubation, 5 mL of Robosep buffer was added to the tube and mixed well by pipetting up and down. The tube was immediately places in the silver magnet (StemCell Technologies catalog #19054) and incubated at room temperature for 5 minutes. After incubation, in one continuous motion, invert magnet and tube and pour off desired fraction into a 50 mL conical. These procedures were repeated for remaining PBMCs (per one donor) and combined. The combined fraction was centrifuged at 1200 rpm for 5 minutes and then supernatants were discarded and cells were resuspended in 5 mL of B cell media. The isolated CD19+ cells were counted on the cell counter.

8.2.3 B Cell Differentiation Assay

Step 1—B cell Activation—day 0 through day 4: Prepare fresh B cell cocktail by adding 50 µg/mL of human transferrin to B cell media. (Iscoves+10% PFBS, 1% P/S, and 5 µg/mL human insulin). Filter required volume of media needed for experiment through a 0.22 µM filter. Add B cell differentiation cocktail (final concentration): recombinant human IL-2 (20 U/mL), IL-10 (50 ng/mL), IL-15 (10 ng/mL), CD40 Ligand/TNFSF5/histidine-tagged (50 ng/mL), polyHistidine mouse IgG1 antibody (5 µg/mL), and ODN 2006—Human TLR9 ligand (10 µg/mL) to cells. Five milliliters ($1 \times 10^5$/ml) of CD19+ B cell were added to each well of a 6 well flat-bottom plate (final cell count=$5 \times 10^5$/well). Five L (lx)±compound/DMSO was added to each test well (0.1% final DMSO) and incubated at 37° C. for 4 days.

Step 2—Plasmablast Generation—day 4 through day 7: Cells were harvested and counted on the cell counter; an aliquot was removed for flow analysis, the remaining cells were washed with PBS. Prepare fresh B cell cocktail by adding 1 µg/ml of human transferrin to B cell media. (Iscoves+10% PFBS, 1% P/S, and 5 µg/mL human insulin) Filter required volume of media needed for experiment through a 0.22 µM filter. Add B cell differentiation cocktail (final concentration): recombinant human IL-2 (20 U/mL), IL-10 (50 ng/mL), IL-15 (10 ng/mL), IL-6 (50 ng/mL) to cells. Add fresh B cell cocktail and transfer cells back to the original wells and bring volume back to 5 mL. Five L (1×)±compound/DMSO was added to each test well (0.1% final DMSO) and incubated at 37° C. for 4 days.

On day 7, cells were harvested and counted on the cell counter. Cells were then divided for flow analysis and the remaining cells were lysed with RLTbuffer and stored at −80° C. for RNA extraction and gene expression. Supernatants were aliquoted and frozen at −20° C. for immunoglobulin assays.

8.2.4 Preparation of Test Compound Stock Solutions and Dilutions

The test compounds was weighed and dissolved in sterile 100% DMSO (dimethyl sulfoxide; Research Organics, Cleveland, Ohio) to create 40 mM stock solution. Dilutions of the 40 mM stock were used in the assay to obtain final test compound concentrations based on experimental design.

8.2.5 RNA Extraction and Gene Expression

Differentiated B cells (see section 8.2.3) were harvested for total ribonucleic acid (RNA) preparation with a Qiacube RNA extraction instrument (Qiagen, Valencia, Calif.) using QIAGEN RNeasy mini spin-column kits. Purified RNA was reverse transcribed into cDNA with thermal cycler [MJ Research; Inc., St. Bruno, Quebec, Canada) using a reverse-transcriptase kit (Applied Biosystems). The gene expression assay was carried out using 7500 RT-PCR system (Applied Biosystems) in triplicate. A glyceraldehyde 3-phosphate dehydrogenase gene expression assay control was run for each sample and used as a normalization control. For each gene, samples within each experiment were normalized to 0.1% DMSO treatment only for that particular time point.

Supernatants (from section 8.2.3) were harvested and analyzed by ELISA for IgG and IgM production (ZeptoMetrix Corp. Buffalo, N.Y.).

8.2.6 Cell Phenotyping

Differentiated B cells (see section 8.2.3) were harvested, counted, and aliquoted at about 1×10$^6$ cells or less per 4 mL tube. The cells were washed 1× with stain buffer. Next, the cells then were blocked with 10% human serum/PBS for 20-30 minutes. Following blocking, the cells were centrifuged for 5 minutes at 1200 rpm and supernatants discarded. In the 100 µL of remaining buffer, 20 µL of various BD Pharmigen flow antibodies were added according to experimental design. The cells were stained for 20-30 minutes at 4° C. Then the cells were washed 2× with stain buffer and supernatants discarded. Next, 500 µL of stain buffer or PBS was added to the tubes. The samples were immediately analyzed or put at 4° C. overnight. Cells were stained with mouse anti-human CD20 and CD38, CD19 and CD27, or respective isotype controls. All samples were analyzed using a FACSCanto flow cytometer, FACSDiva analysis software (BD Bioscience), and FlowJo Analysis software.

8.2.7 Cell Viability Analysis

To determine live cell count, B cells (see section 8.2.3) were stained with 0.4% trypan blue and live cells counted using the Countess automated cell counter (Invitrogen) in duplicate samples.

The data was graphed using GraphPad Prism 5.0 software. $IC_{50}$ values were calculated using non-linear regression, sigmoidal-dose response constraining the top to 100% and bottom to 0% allowing for a variable slope. The results for test compounds in the Ig assays were expressed as the percentage inhibition relative to control DMSO values.

Figure 2:
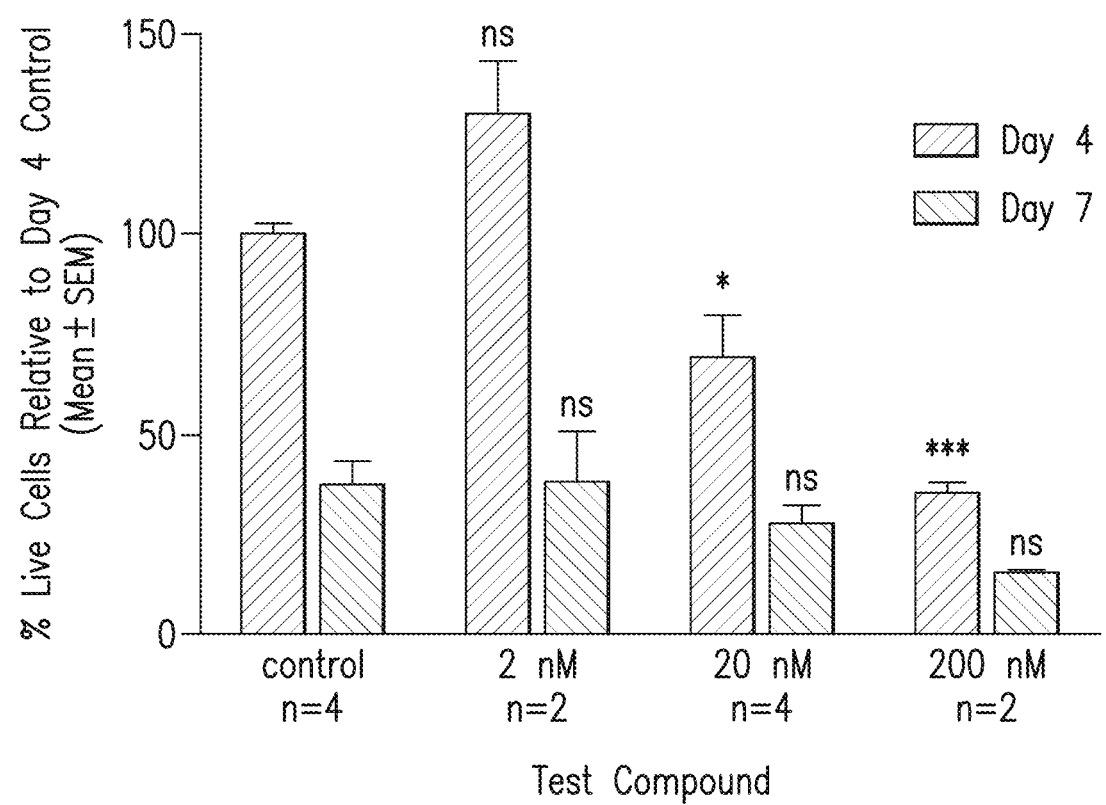
FIG. 2 depicts effect of (S)-3-[4-(4-morpholin-4-ylmethyl-benzyloxy)-1-oxo-1,3-dihydro-isoindo-2-yl]piperidine-2,6-dione on cell viability during plasmablast differentiation.
Figure 3:
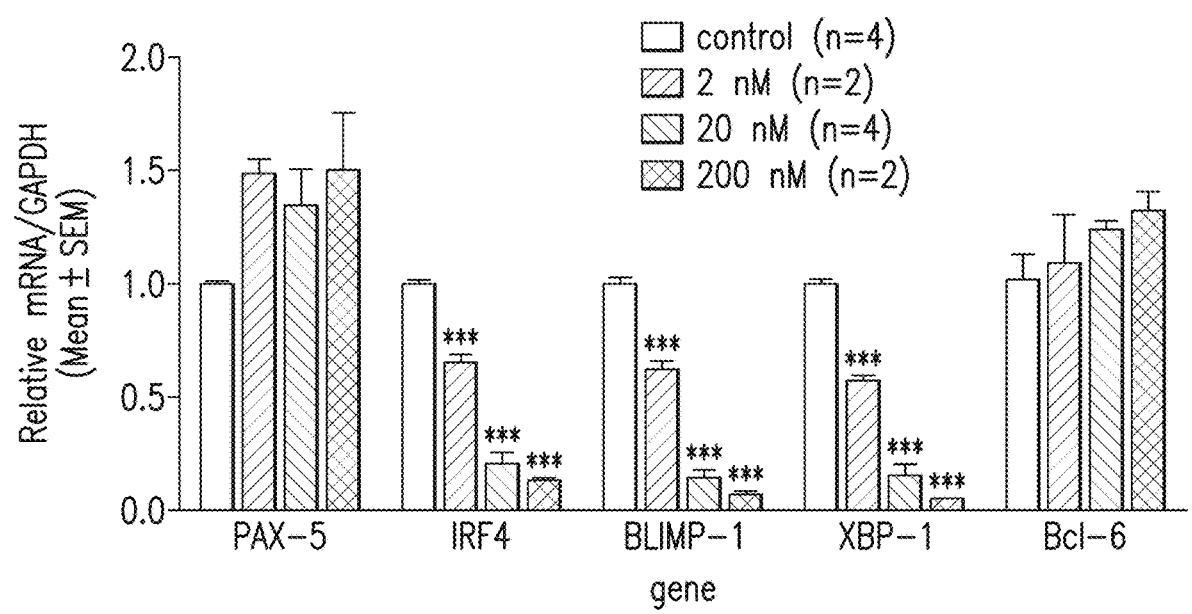
FIG. 3 depicts effect of (S)-3-[4-(4-morpholin-4-ylmethyl-benzyloxy)-1-oxo-1,3-dihydro-isoindo-2-yl]piperidine-2,6-dione on B and plasma cell transcription factor expression.
Figure 4:
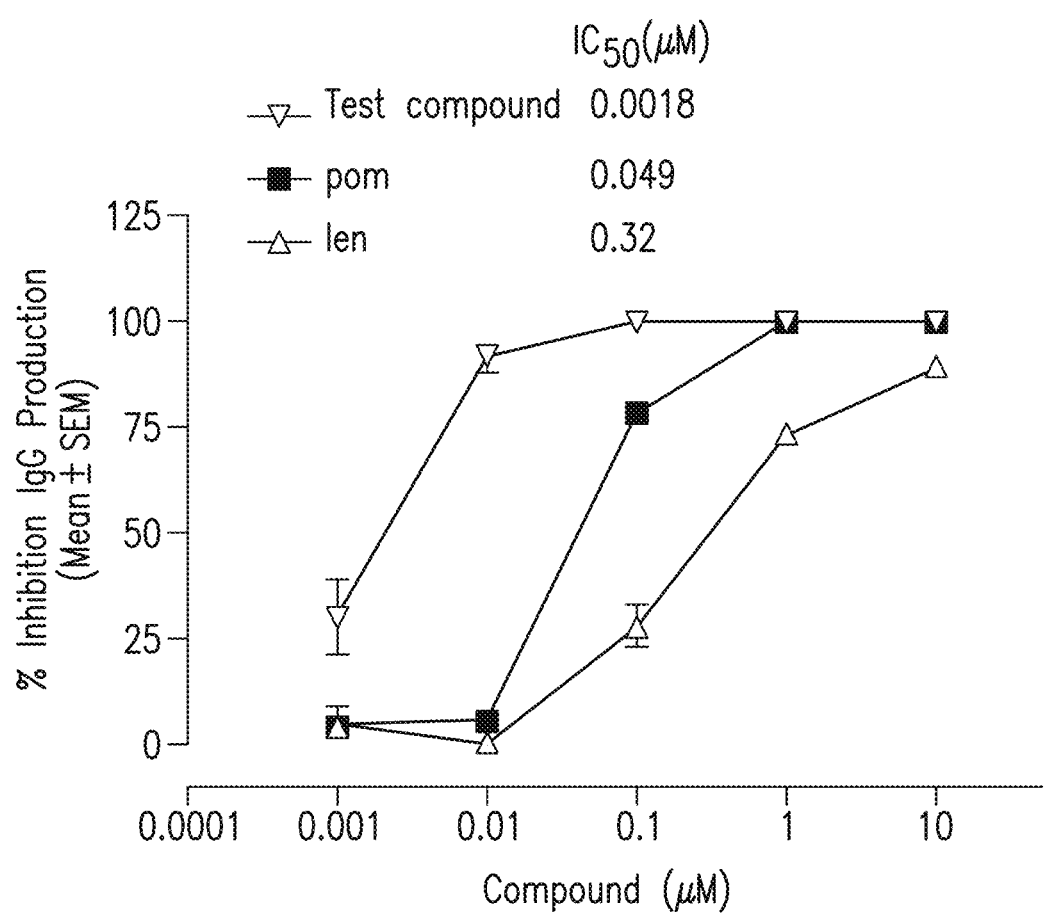
FIG. 4 depicts effect of (S)-3-[4-(4-morphlin-4-ylmethyl-benzyloxy)-1-oxo-1,3-dihydro-isoindo-2-yl]piperidine-2,6-dione on IgG production in plasmablast cultures.

The test compound dose-dependently reduced the percentage of CD20-CD38+ plasmablasts, and increased the percentage of CD20+CD38-activated B cells. The plasmablast population (quadrant 1) was 30.4% in the DMSO control at day 7, and the test compound reduced the population to 27.3% at 2 nM, 2.1% at 20 nM, and 0.4% at 200 nM (FIG. 1). The test compound reduced B cell viability during the first 4 days of culture (FIG. 2). The effect of the test compound on B and plasma cell transcription factor expression is depicted in FIG. 3. The effect of the test compound on IgG production in plasmablast cultures is depicted in FIG. 4.

Figure 5A:
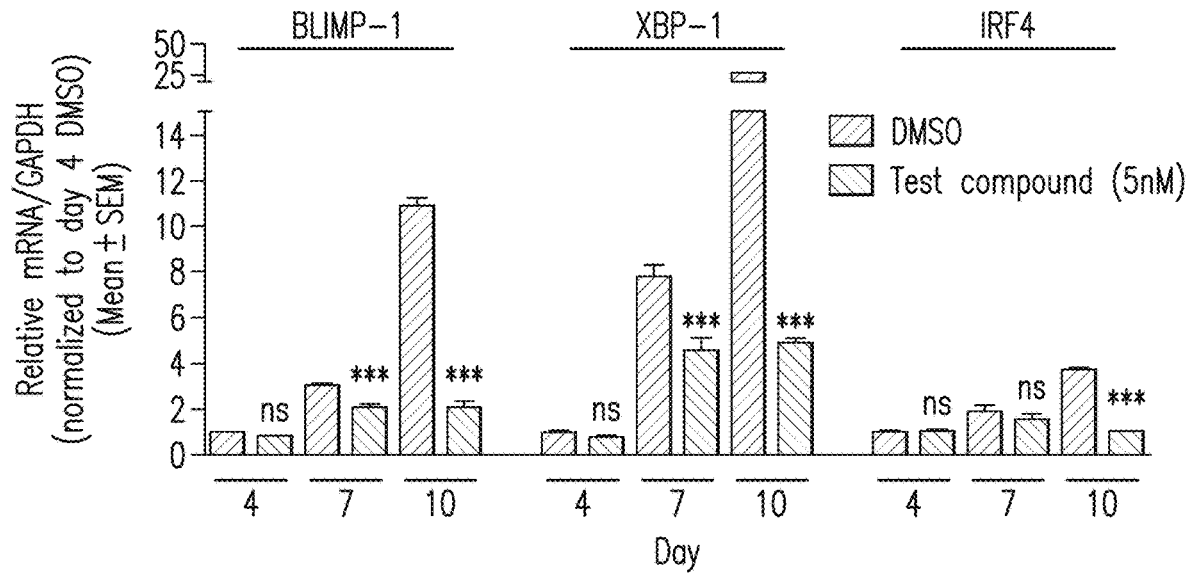
FIGS. 5A and 5B depict effect of (S)-3-[4-(4-morphlin-4-ylmethylbenzyloxy)-1-oxo-1,3-dihydro-isoindo-2-yl]piperidine-2,6-dione on B and plasma cell transcription factor expression.
Figure 5B:
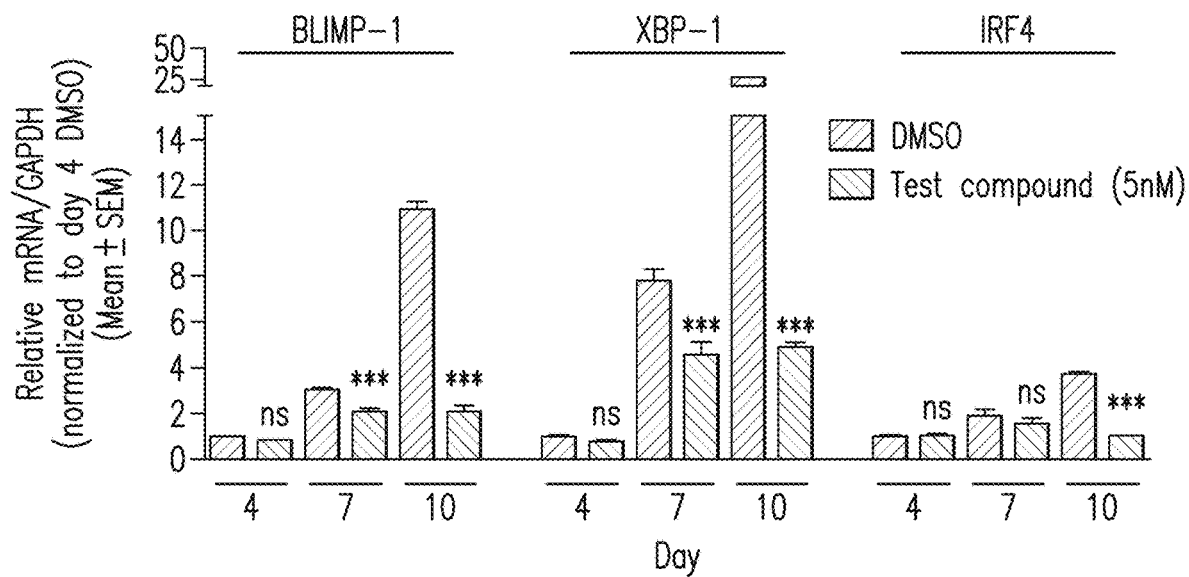

The test compound dose-dependently inhibited expression of plasma cell transcription factors RF4, BLIMP1, and XBP1 significantly. The test compound enhanced B cell transcription factor PAX5. The effect of the test compound on B and plasma cell transcription factor expression is depicted in FIGS. 5A and 5B.

Figure 6:
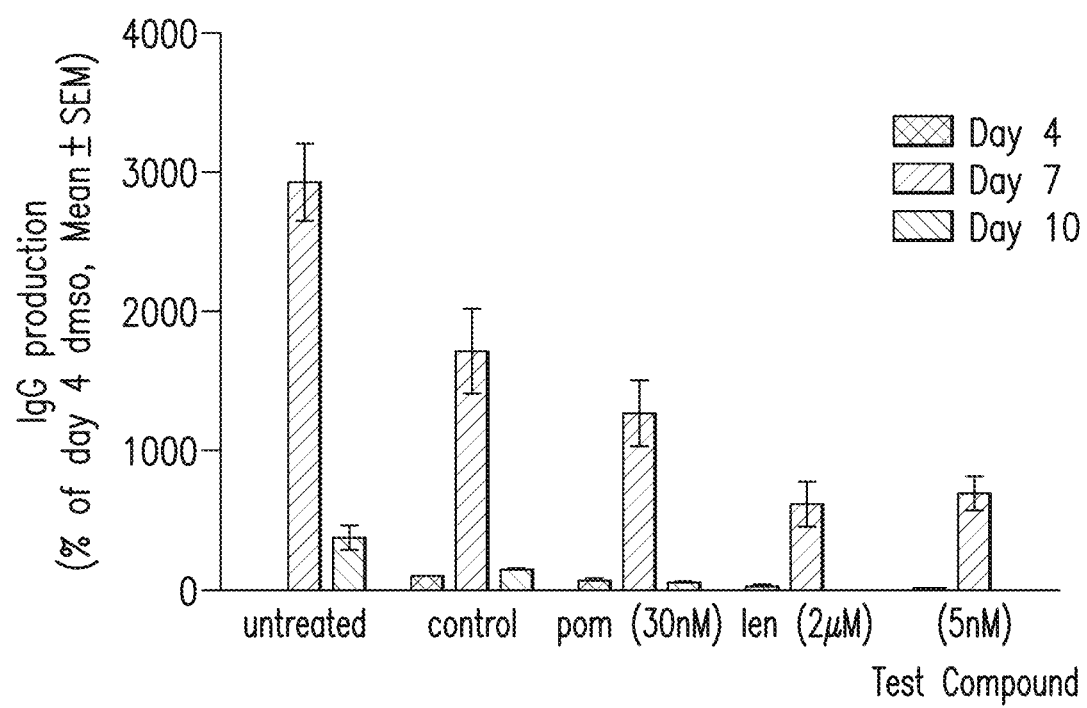
FIG. 6 depicts effect of (S)-3-[4-(4-morphlin-4-ylmethylbenzyloxy)-1-oxo-1,3-dihydro-isoindo-2-yl]piperidine-2,6-dione on IgG production in B cell cultures on days 4, 7 and 10.
Figure 7:
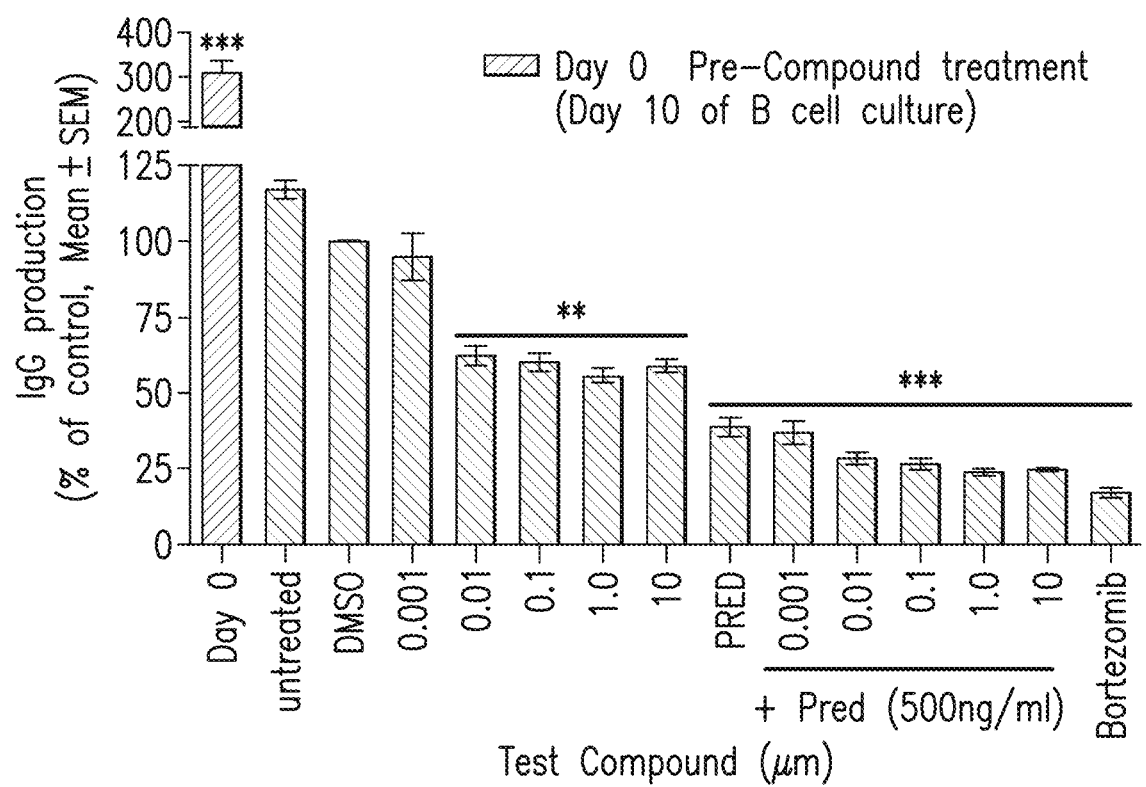
FIG. 7 depicts effect of (S)-3-[4-(4-morphlin-4-ylmethylbenzyloxy)-1-oxo-1,3-dihydro-isoindo-2-yl]piperidine-2,6-dione, alone and in combination with prednisolone, on IgG production by in vitro-differentiated plasma blasts/plasma cells.
Figure 8:
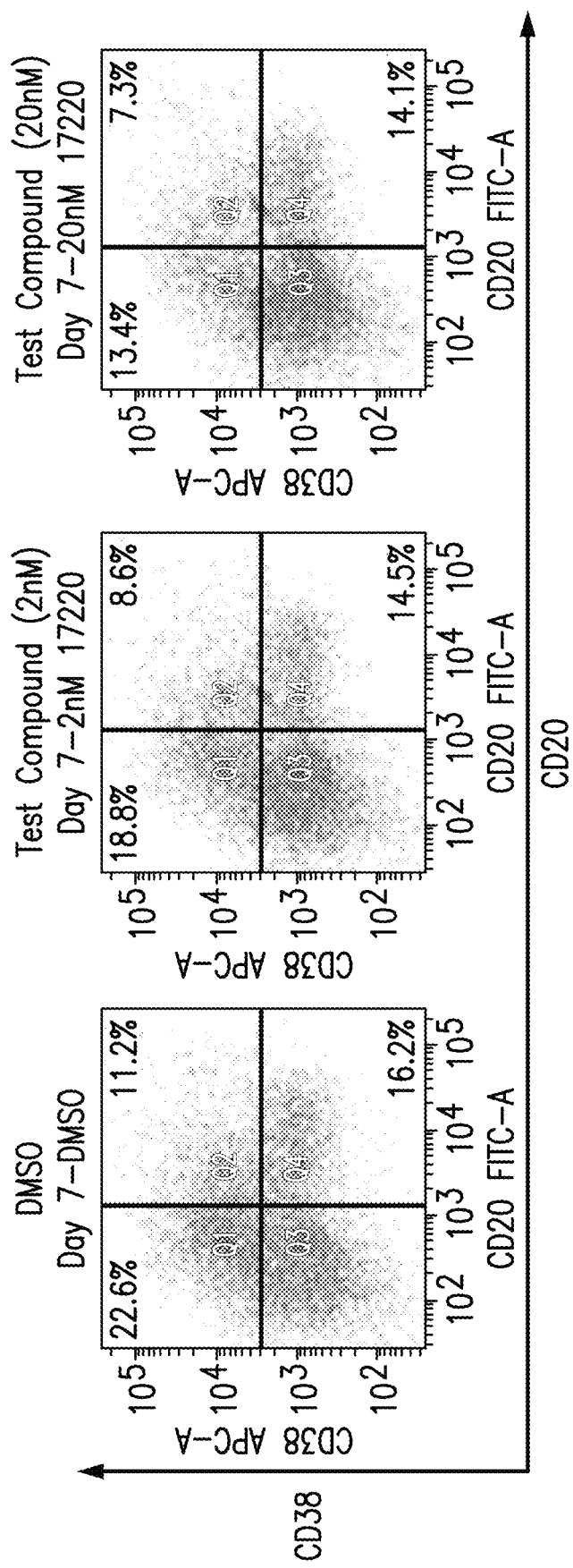
FIG. 8 depicts effect of (S)-3-[4-(4-morphlin-4-ylmethylbenzyloxy)-1-oxo-1,3-dihydro-isoindo-2-yl]piperidine-2,6-dione on CD20/CD38 expression during B cell differentiation at day 7.
Figure 9:
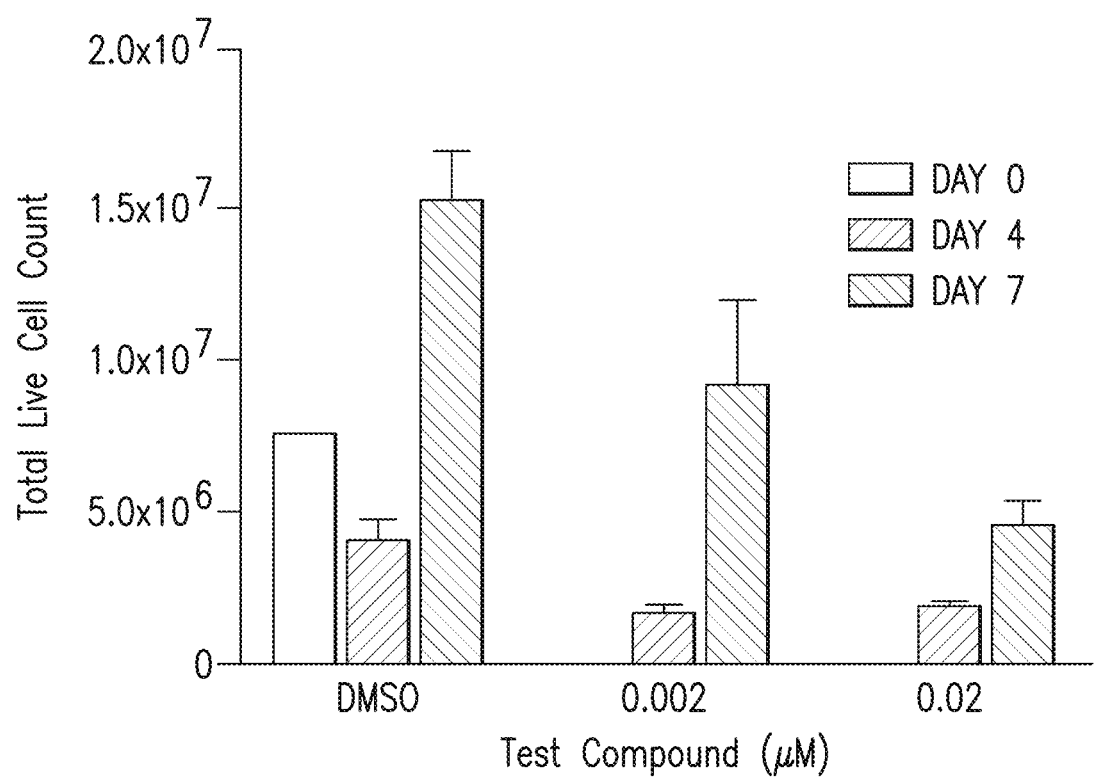
FIG. 9 depicts effect of (S)-3-[4-(4-morphlin-4-ylmethylbenzyloxy)-1-oxo-1,3-dihydro-isoindo-2-yl]piperidine-2,6-dione on cell viability during plasmablast differentiation.

The test compound, pomalidomide, and lenalidomide inhibit IgG production with $IC_{50}$ of 0.0018 µM, 0.049 µM, and 0.32 µM, respectively. The data indicated that the test compound is 27-fold more potent than pomalidomide at inhibiting IgG production during plasmablast differentiation. The effect of the test compound on IgG production in B cell cultures on days 4, 7 and 10 is depicted in FIG. 6. The effect of the test compound, alone and in combination with prednisolone, on IgG production by in vitro-differentiated plasma blasts/plasma cells is depicted in FIG. 7. The effect of the test compound on CD20/CD38 expression during B cell differentiation at day 7 is depicted in FIG. 8. The effect of the test compound on cell viability during plasmablast differentiation is depicted in FIG. 9.

Figure 10:
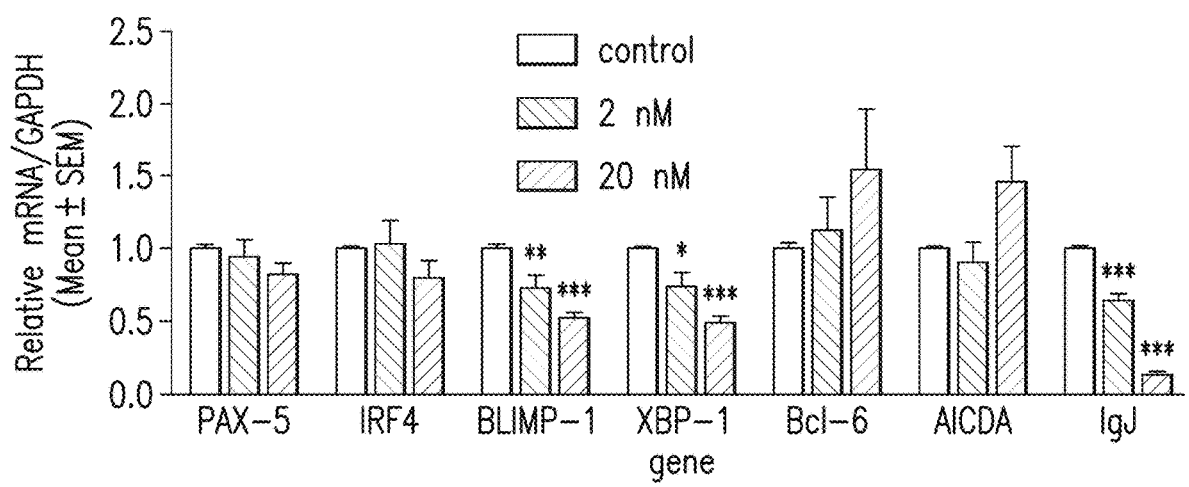
FIG. 10 depicts effect of (S)-3-[4-(4-morphlin-4-ylmethylbenzyloxy)-1-oxo-1,3-dihydro-isoindo-2-yl]piperidine-2,6-dione on B cell differentiation and function in SLE patient PBMC in vitro.

In peripheral blood mononuclear cell isolated by patients with systemic lupus erythematosus (SLE), the test compound inhibited IgG and IgM production with $IC_{50}$s of 3.2 nM and 0.9 nM, respectively. These findings indicated that the test compound has the potential to inhibit B cell differentiation to the plasma cell lineage, and suggested that the test compound may be useful in the treatment of autoimmune disorders such as SLE, which are characterized by the overproduction of autoantibodies. The effect of the test compound on B cell differentiation and function in SLE patient PBMC cells is depicted in FIG. 10. The effect of the test compound on IgG and IgM productions in normal and SLE patient PBMC cells is depicted in Table 1.

Figure 11A:
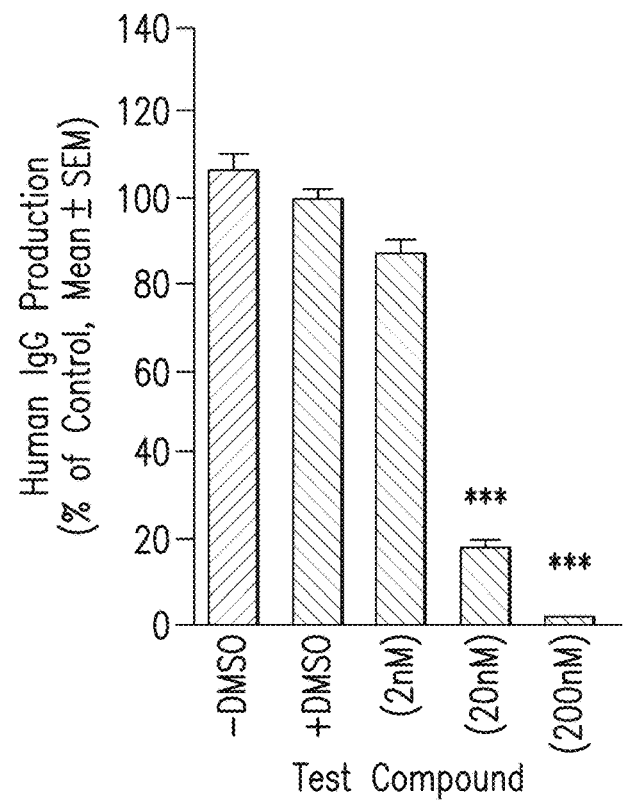
FIGS. 11A and 11B depict effect of (S)-3-[4-(4-morphlin-4-ylmethylbenzyloxy)-1-oxo-1,3-dihydro-isoindo-2-yl]piperidine-2,6-dione on IgG and IgM production, respectively, in B cell cultures on day 7.
Figure 11B:
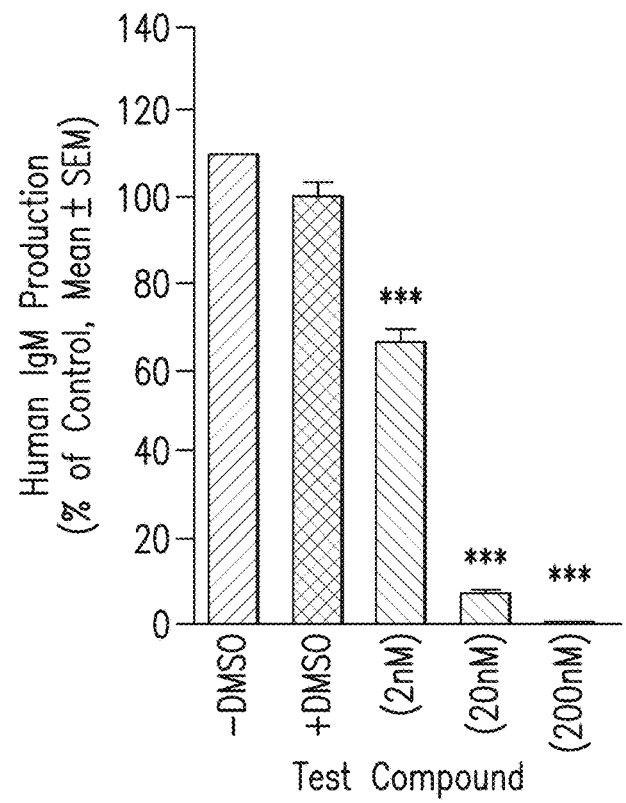

FIGS. 11A and 11B depict the effect of the test compound on human IgG and IgM production, respectively, in B cell cultures on day 7.

TABLE 1

Potency for Inhibition of Normal and SLE PBMC Production of IgG and IgM

| | IgG $IC_{50}$ (nM) | | IgM $IC_{50}$ (nM) | |
| --- | --- | --- | --- | --- |
| | SLE (n = 3) | Normal (n = 3) | SLE (n = 3) | Normal (n = 3) |
| Test Compound | 3.2 | 2.1 | 0.9 | 0.35 |
| pomalidomide | 19 | 63 | 3.8 | 17 |
| apremilast | >10,000 | >10,000 | >10,000 | >10,000 |

8.3 Example 3: B Cell Differentiation Assay Using Flow Cytometry and Laser Scanning Cytometry Cell Culture Materials: Enriched normal B cells and SLE patient peripheral blood mononuclear cells (PBMC) were cultured in the in vitro B cell differentiation system with IMDM medium (Invitrogen) and 10% FCS, supplemented with human transferrin and human insulin (Sigma) plus cytokine cocktail. Test compound was added to culture on day 0 and day 4.

B Cell Differentiation Protocol: Enriched B cells were isolated from fresh buffy-coat (leukocyte enriched units) by Ficoll-Hypaque density gradient centrifugation followed by incubation with EasySep negative selection human B cell enrichment kit (Stem cell technologies). In brief, $2 \times 10^8$/ml PBMC were mixed with 4 ml of Robosep buffer and transferred to a 14 mL polystyrene round bottom tube. EasySep Human B cell enrichment cocktail (200 µL) was added per tube, vortexed and incubated at room temperature for 10 minutes. EasySep Magnetic particles were added (300 µL per tube) and vortexed and incubated at room temperature for 5 minutes. Robosep buffer (5 mL) was added to each tube and mixed well by pipetting up and down. Tubes were placed in the silver magnet and incubated at room temperature for 5 minutes. The magnet and tube were picked up and in one continuous motion inverted, pouring off the desired fraction into a 50 mL conical. Cells were spun at 1200 rpm for 5 minutes. Supernatant was poured off and 5 mL of fresh B cell media added. After cells were counted, an aliquot was removed for FACS analysis and the remaining cells were used for culture. CD19+ B cells were isolated to ~95% purity as determined by flow cytometry. Purified B cells were plated at $1 \times 10^5$ cell/ml in a sterile 6 well plate at 5 ml per well. All cell cultures were performed in IMDM medium (Invitrogen) and 10% FCS, supplemented with human transferrin and human insulin (Sigma). B-cell activation, PB generation and PC generation were performed based on the modified in vitro system of differentiation of B cells into plasma cells. All recombinant human cytokines IL-2, IL-4, IL-6, IL-10, IL-15, INF-α, and CD40 L and anti-polyhistidine mAb were added at indicated culture steps. Various concentrations of test compound (2, 20 and 200 nM) were added to culture on day 0 and day 4. On day 4, pool all cells together from same treatment, count cells, remove cells for FACS analysis and cytospin preparation. Plate the remaining cells at $2.5 \times 10^5$ cell/ml in a sterile 6 well plate at 5 ml per well. SLE PBMCs were cultured for 7 days under conditions to promote plasma cell differentiation as normal B cells.

Immunophenotyping For Flow Cytometric Analysis: Cells were stained using multicolor direct immunofluorescence stain for flow cytometric analysis. Surface staining was performed before cell fixation and permeabilization. Cells (50 µl; $1 \times 10^6$ cells/ml in washing buffer, 2% FBS with 0.1% NaN3 in PBS) were used for each staining. The cells were stained with isotype control mAb (1 g/106 cells) and multicolor FITC-conjugated anti-CD20 mAb and PE-conjugated anti-CD38 mAb, or PerCP-Cy5.5 conjugated anti-CD44 mAb, PE-conjugated anti-CD83 mAb were used for day 4 activated B cells (CD20+CD38-cells), and day 4 PBs and day 7 PBs (CD20-CD38+), and other staining, analyzed by flow cytometry as per manufacturer's instructions. The intracellular staining of transcription factor proteins (BCL-6, IRF-4, BLIMP-1, PAX-5 and XBP-1) and IgJ was performed according to the manufacturer's recommendations. Flow cytometric analysis was performed with a FACSCanto using FACSDiva 6 (BD Biosciences). For data analysis, Flowjo (Tree Star) software was used.

Preparation Of Cytospin From Single Cell Suspension And Immunofluorescence Staining for iCyte: A cell suspension of not more than $0.5 \times 10^6$ cells/ml of 2% FBS-containing PBS was prepared. Up to 200 µl of this suspension was loaded in each cuvette and spinned at 800 rpm for 3 min. The cuvette and the paper were carefully detached without damaging the fresh cytospin and proceeded with either immediate fixation or drying. Unfixed cytospins were stored for max 2 days at room temperature. Cells on slides were fixed with increasing concentrations of EtOH and allowed to dry prior to staining. After blocking non-specific binding with normal serum (species same as secondary antibody), sections were incubated with the mixture of following monoclonal antibodies in a humidified chamber at cool room for overnight: (i) anti-human CD38 as plasmablast cell marker, and (ii) anti-BCL-6, IRF-4, BLIMP-1, PAX5 and XBP-1 for transcription factor proteins. After washings, slides were incubated for 1 hr at room temperature in dark with the mixture of secondary antibodies which were raised in different species (with two different fluorochromes, i.e., Alexa Fluor-488 and Alexa Fluor-633). The slides were then rinsed in PBS, counterstained with DAPI for 20 minutes at room temperature, coverslipped with anti-fade fluorescent mounting medium, and sealed with nail polish. The slides were stored in dark at 4° C. To exclude false positives produced by nonspecific binding of the secondary antibody, all of the tissues were treated in the same manner with buffer substituting for the primary antibody. The color of the antibody staining was observed and quantity was analyzed in the tissue sections using iCyte.

Laser Scanning Cytometer Image Capturing And Fluorescence Quantitative Analysis: Dual-color immunofluorescence stain was performed on cells which were cytospined on slides (Cytospin 4, Thermo scientific) based on standard IHC method. Image capturing and fluorescence quantitative analysis were performed using a laser scanning cytometry (iCys quantitative imaging cytometry, CompuCyte). Two passes were set up (first pass for 488 and second pass for 405/633). Low resolution scan was used for mosaic scan, and high resolution scan for region scan and analysis. In brief, the slide was placed on the LSC stage and a region selected for scanning. The LSC utilized the argon laser operating at 5 mW. The slide was scanned using the 20× objective. Cells were identified and selected by contouring on blue fluorescence and a minimum cell size, as determined by DAPI staining. The cell detection threshold was set to select single cells based on forward angle light scatter displayed in a dot plot of cell area vs. forward scatter integral. Laser light-scatter events were captured and used to contour single cells within the scan data display. Contour discrimination was set from the nuclear portion of the scanned cell such that about 67% of the total light scatter pixelation was contoured. Green and long red PMT-detector gain voltages are set so that no greater than 75% maximum saturation of the max pixel in the respective fields is achieved during the scan. After establishing the scan area, the slide was analyzed using a 40× objective. A minimum of 6 scanning areas for each slide was examined. A cell gallery was created by relocation of cells from each of the major peaks in the histogram of integrated long red fluorescence. The morphologic composition of relocated cells was examined for purposes of quality assurance. Data can be analyzed in either integrated log fluorescence mode or in linear max pixel mode. Different cell population in LSC scanning was scored as percentage and MFI, and quantitative comparison to DMSO controls.

Data Analysis: Flow cytometry surface and intracellular molecules were analyzed by FACSCanto. Data analysis was done by Flowjo. The color of the antibody staining was observed and quantity was analyzed in the tissue sections using iCyte. Different cell population in FCM and LSC scanning was scored as percentage and MFI, and quantitative comparison to DMSO controls. The data was expressed as Mean SEM. All of the data was graphed using GraphPad Prism 6.1 (GraphPad Software; San Diego, Calif.). Statistical analysis was performed using One-Way ANOVA (Dunnett's multiple comparison test), and paired student t test. P values less than or equal to 0.05 were considered significant.

Figure 12A:
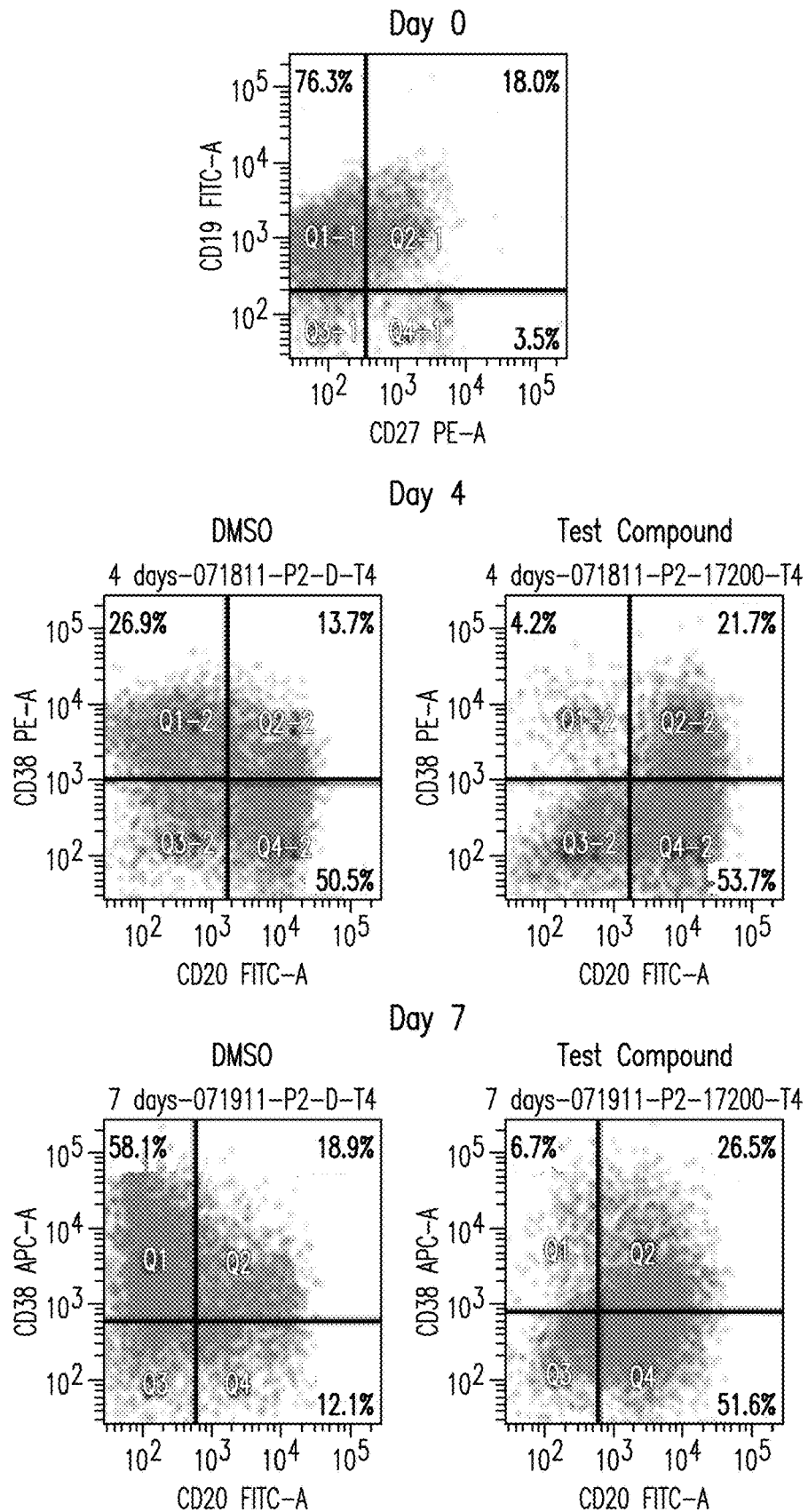
FIGS. 12A and 12B depict effect of (S)-3-[4-(4-morphlin-4-ylmethylbenzyloxy)-1-oxo-1,3-dihydro-isoindo-2-yl]piperidine-2,6-dione on differentiation of CD19+ B cell into plasma blasts/plasma cells.
Figure 12B:
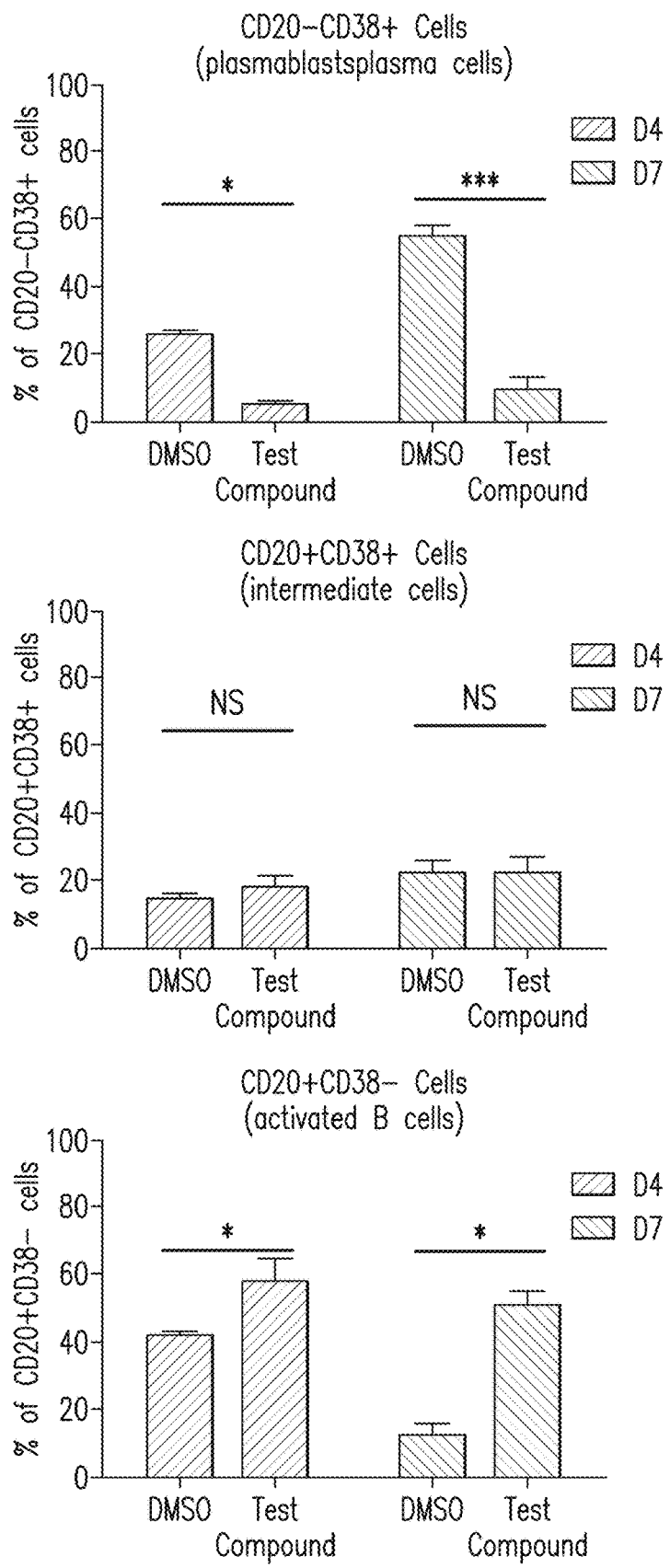
Figure 13:
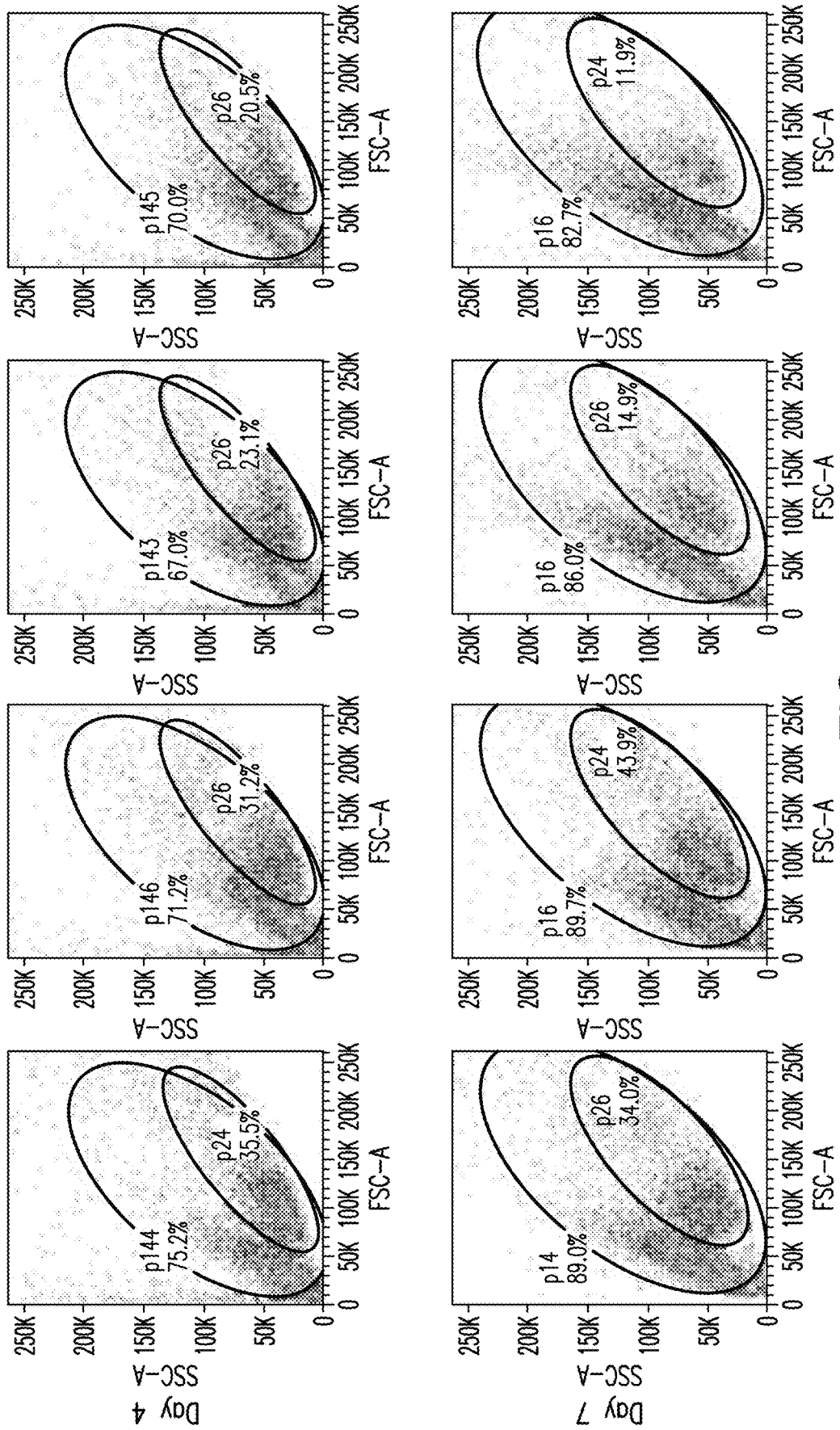
FIG. 13 depicts effect of (S)-3-[4-(4-morphlin-4-ylmethylbenzyloxy)-1-oxo-1,3-dihydro-isoindo-2-yl]piperidine-2,6-dione on large size cell population (gate p2) in normal B cell differentiation assay.

B cells were cultured using the modified in vitro system for differentiation of B cells into plasma cells as described above. Multicolor FITC-conjugated anti-CD20 mAb and PE-conjugated anti-CD38 mAb were used for day 4 activated B cells (CD20+CD38-cells) and day 7 plasmablasts (PBs) (CD20-CD38+). Data from 3 separate experiments representative of 3 donors are shown in Table 2. The results showed the test compound had a significant effect on B cell differentiation to the plasmablast/plasma cell lineage. It increased activated B cells and reduced plasmablasts, also reduced cell viability over time (FIGS. 12A and 12B). The activated B cells (CD20+CD38-cells) treated with the test compound (20 nM) did not change significantly between Day 4: (57.9% 11.5%) and Day 7 (50.5%±8.6%), but the test compound significantly increased activated B cells when compared with the vehicle (DMSO) control which at Day 4 (42.1% 1.5%, $p<0.05$) and at Day 7 (12.5%±5.7%, $p<0.05$). Meanwhile, the test compound significantly reduced plasmablasts/plasma cells (CD20-CD38+) at Day 4 (4.8% 2.3%) and at Day 7 (9.7% 5.4%) compared with DMSO control (Day 4, 25.9% 2.4% $p<0.05$; and at Day 7, 54.8% 5.0%, $p<0.001$). Furthermore, the test compound dose-dependently depleted large size cell population (gate p2) in the normal B cell differentiation assay (FIG. 13). The percentage of large size cells at Day 4 of the test compound treated was 31.2%, 23.1% and 20.4% for 2 nM, 20 nM and 200 nM treatments respectively. The percentage of large size cells at Day 7 of the test compound treated was 34.9%, 19.9% and 11.94% for 2 nM, 20 nM and 200 nM treatments respectively. Comparison with DMSO control, the number was at 35.5% and 34.9% at Day 4 and Day 7 respectively.

factor expression in plasmablasts/plasma cells. It significantly decreased IRF-4 ($p<0.5$), BLIMP-1 ($p<0.05$), and XBP-1 ($p<0.05$) expression at Day 4, but significantly increased BCL-6 ($p<0.05$) on Day 7.

Figure 15A:
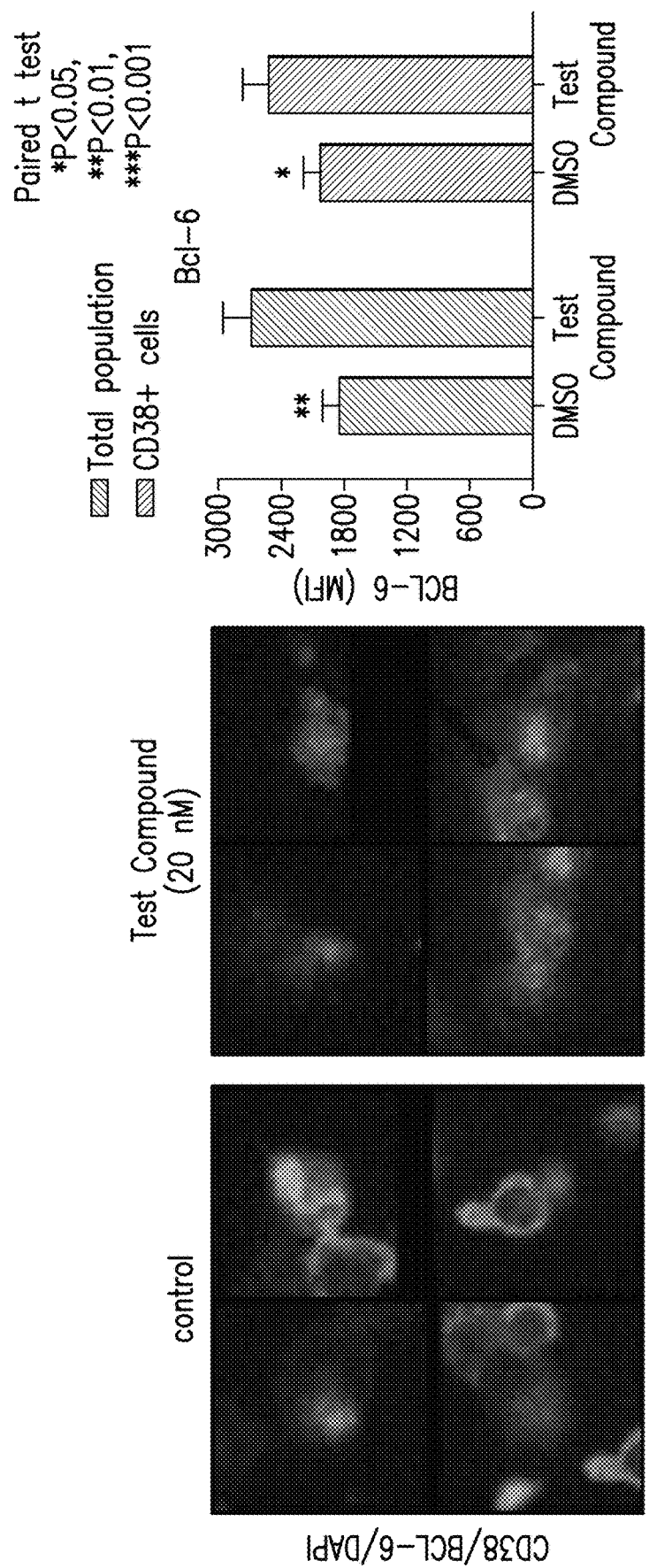
FIGS. 15A-15E depict effect of (S)-3-[4-(4-morphlin-4-ylmethylbenzyloxy)-1-oxo-1,3-dihydro-isoindo-2-yl]piperidine-2,6-dione (20 nM) on plasma cell transcription factor expression in day 7 cultured B cells.
Figure 15B:
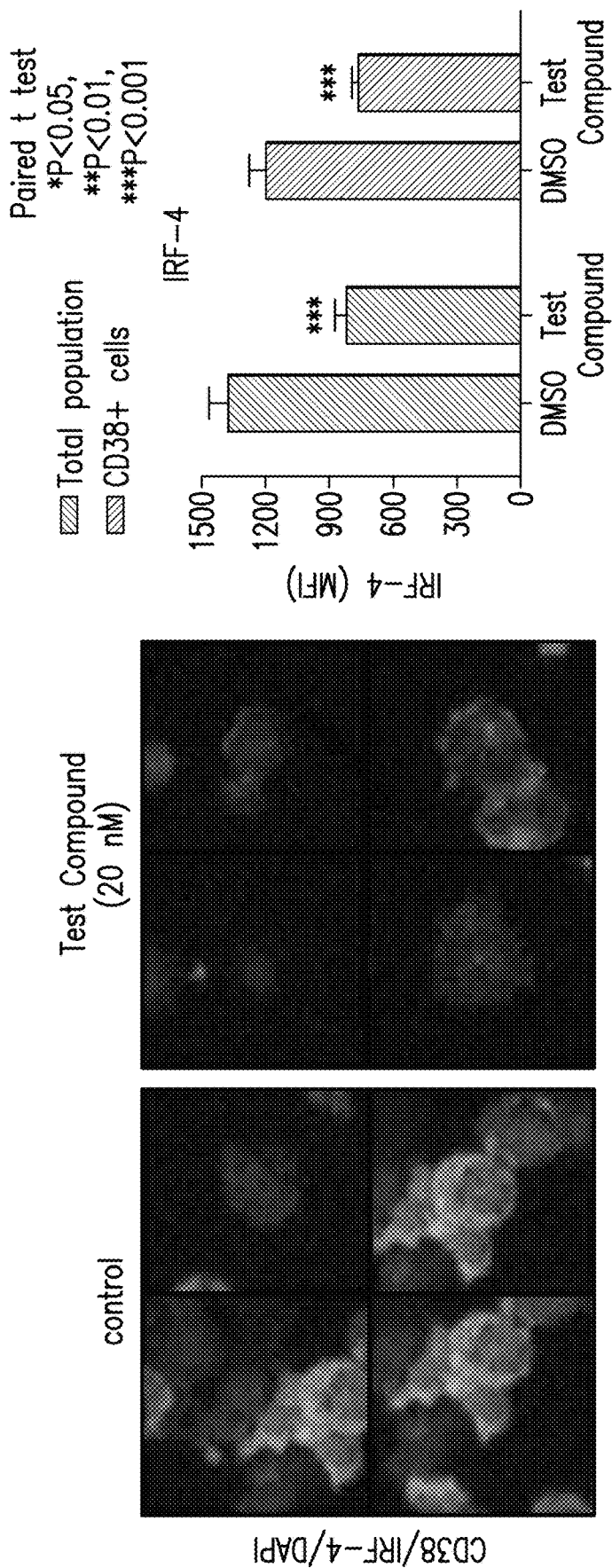
Figure 15C:
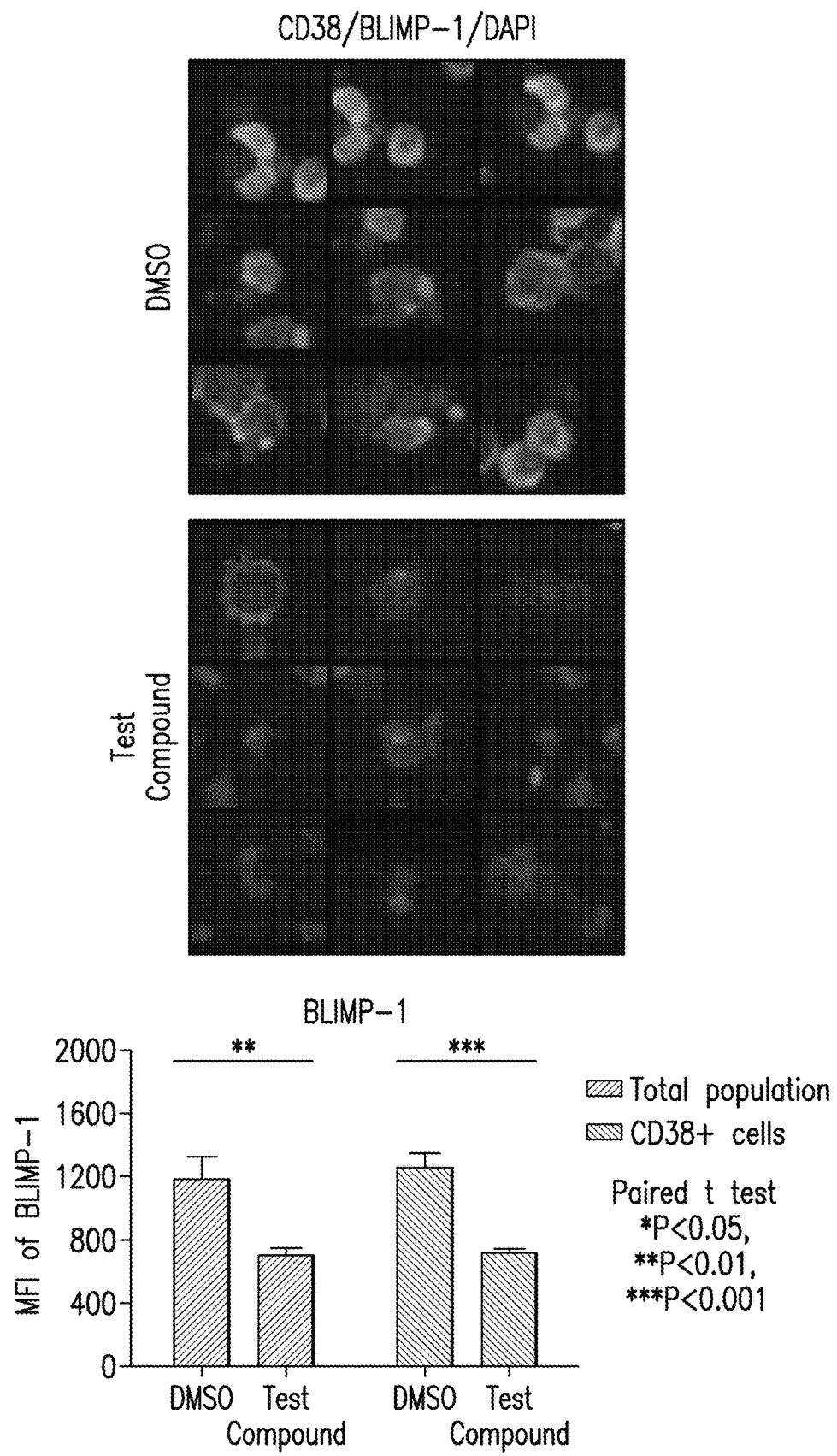
Figure 15D:
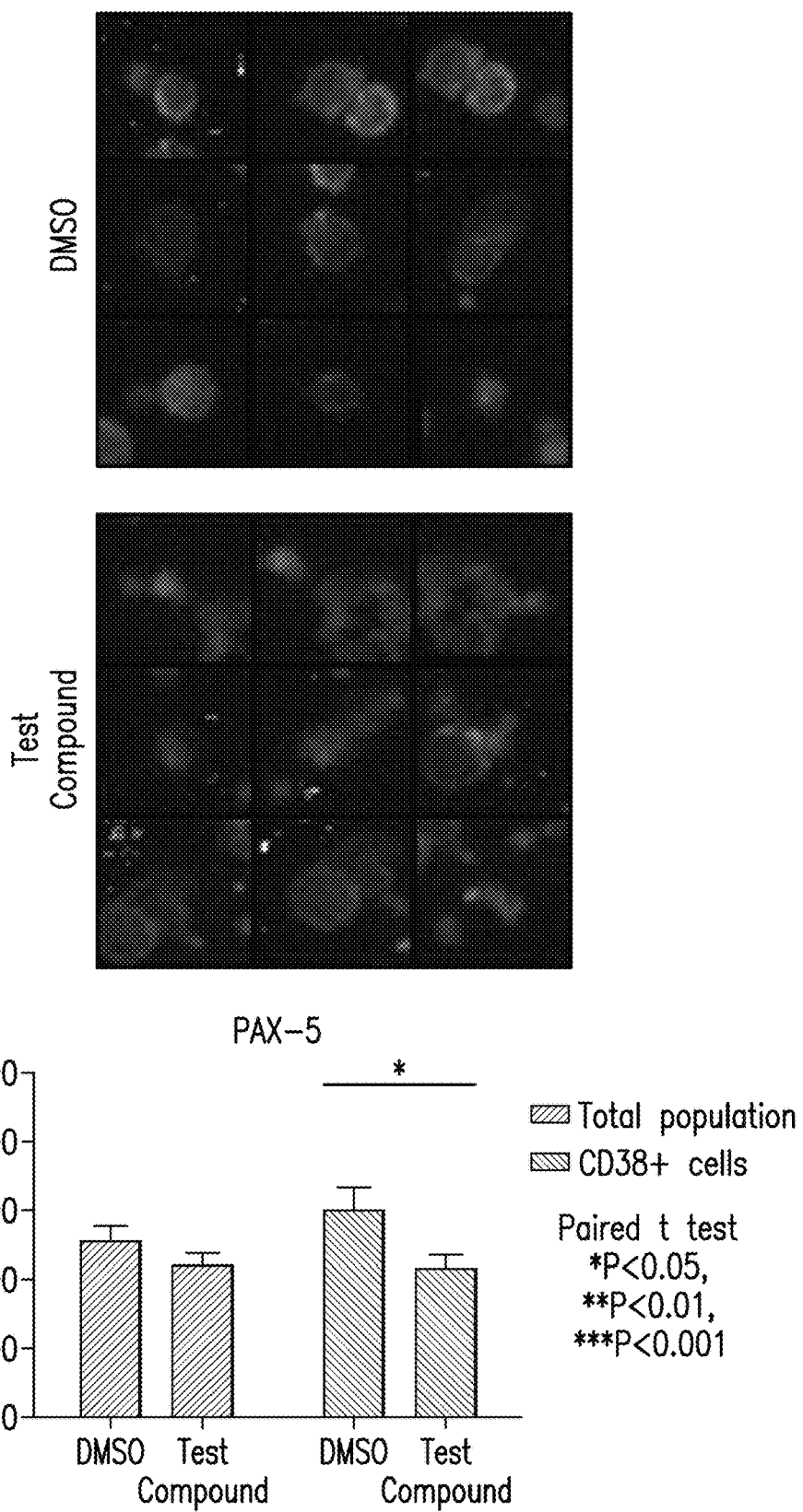
Figure 15E:
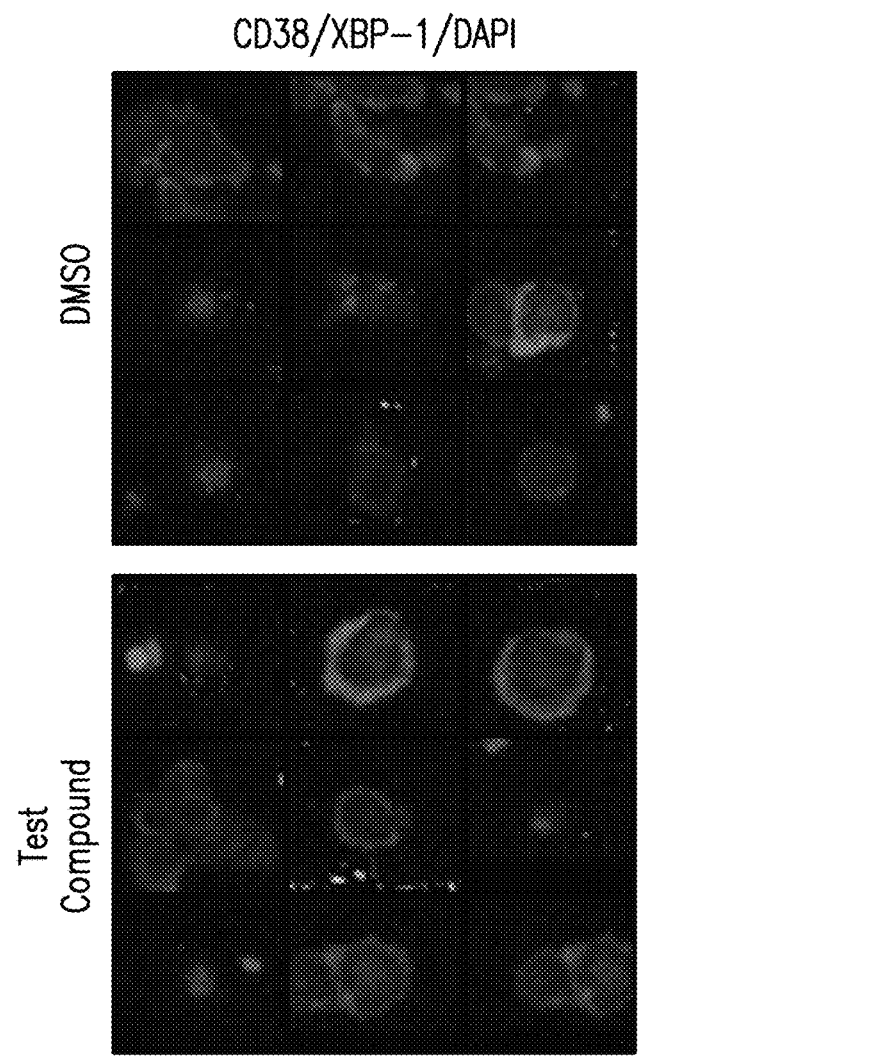
Figure 15E:
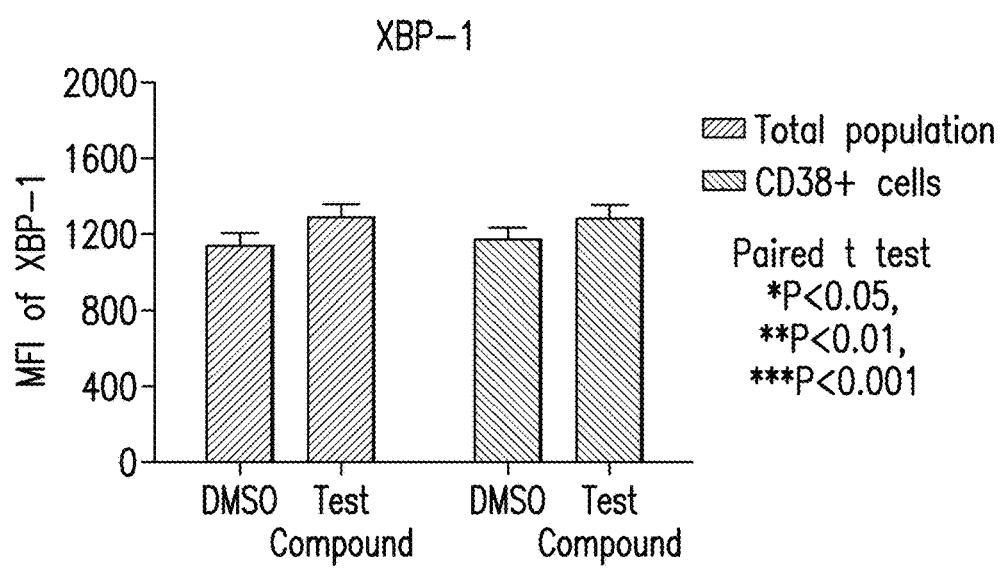
Figure 16:
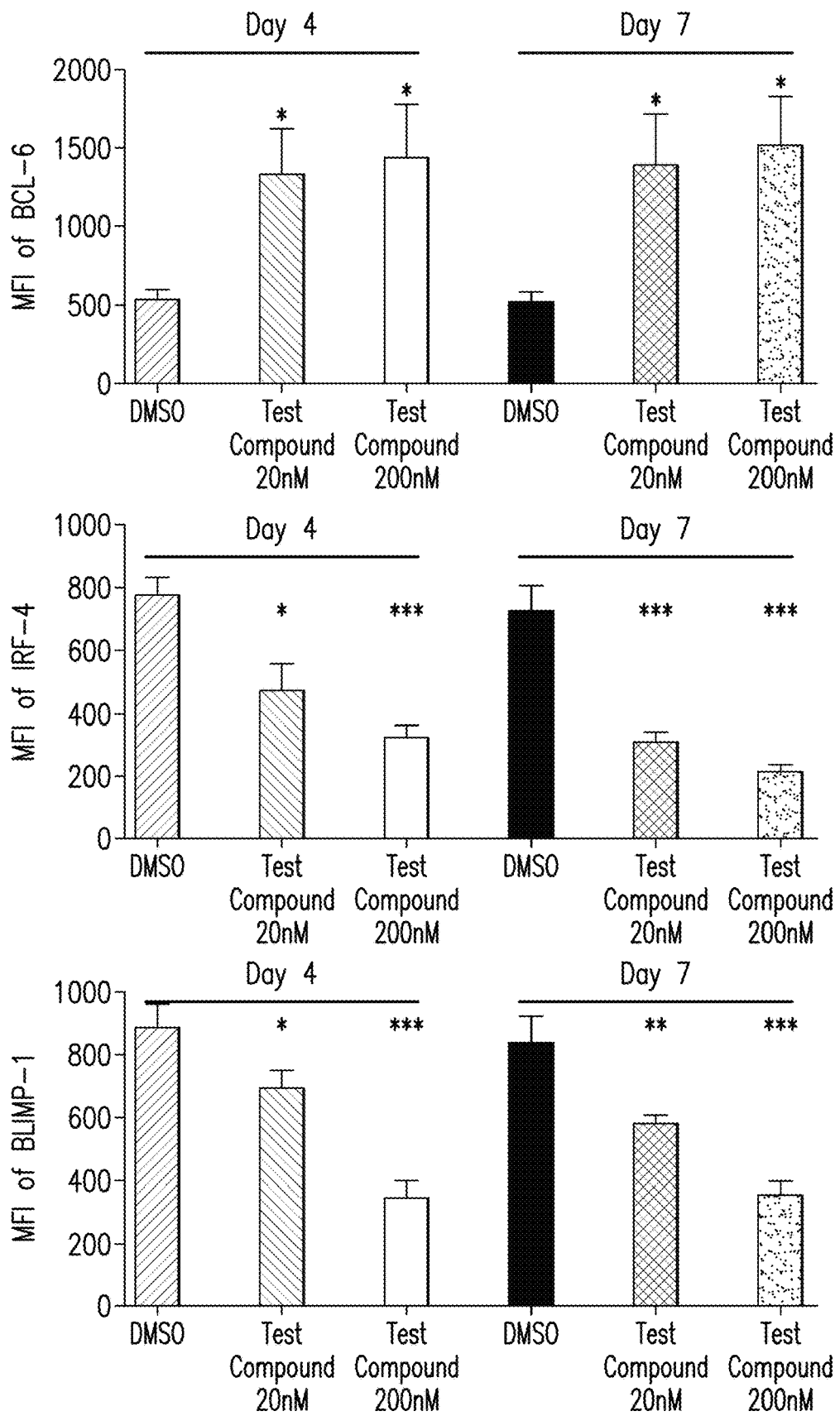
FIG. 16 depicts effect of (S)-3-[4-(4-morphlin-4-ylmethylbenzyloxy)-1-oxo-1,3-dihydro-isoindo-2-yl]piperidine-2,6-dione on transcription factors expression in CD38+ plasmablast/plasma cells from differentiating SLE patient PBMC.

Laser scanning cytometry (iCyte) was used for quantitative analysis to confirm the flow cytometry results described above. The B cells from normal donors and PBMC from SLE patients were cultured as described in above method. The cells were harvested at Day 4 and Day 7 for cytospining cells to slides, then followed double-immunofluorescence stain as described in Methods. CD38 (green) was expressed by plasmablasts/plasma cells, transcription factor (Red) BCL-6, IRF-4, BLIMP-1, PAX5, or XBP-1 was colocalized in cytoplasm or nucleus. The nucleus were counterstained with DAPI (blue). In Day 7 normal B cell samples, when compared with DMSO control, the test compound (20 nM) significantly increased BCL-6 (FIG. 15A, $p<0.01$), decreased IRF-4 (FIG. 15B, $p<0.001$) and BLIMP-1 (FIG. 15C, $p<0.01$) expression in whole lymphocyte population, and significantly increased BCL-6 ($p<0.05$), decreased IRF-4 ($p<0.001$), BLIMP-1 ($p<0.001$), and PAX-5 (FIG. 15D, $p<0.05$) expression in CD38+ plasmablast/plasma cells. There was no change of XBP-1 (FIG. 15E) in both cell populations. In SLE patient PBMC, three transcription factors were tested: BCL-6, IRF-4 and BLIMP-1. The data indicated that the test compound had similar activity in these transcription factors as with healthy donor cells. The test compound dose-depend significantly increased BCL-6 expression, and inhibited RF-4 and BLIMP-1 expression in CD38+ plasmablast/plasma cells from differentiating Day 4 and Day 7 SLE patient PBMC (FIG. 16).

Figure 17:
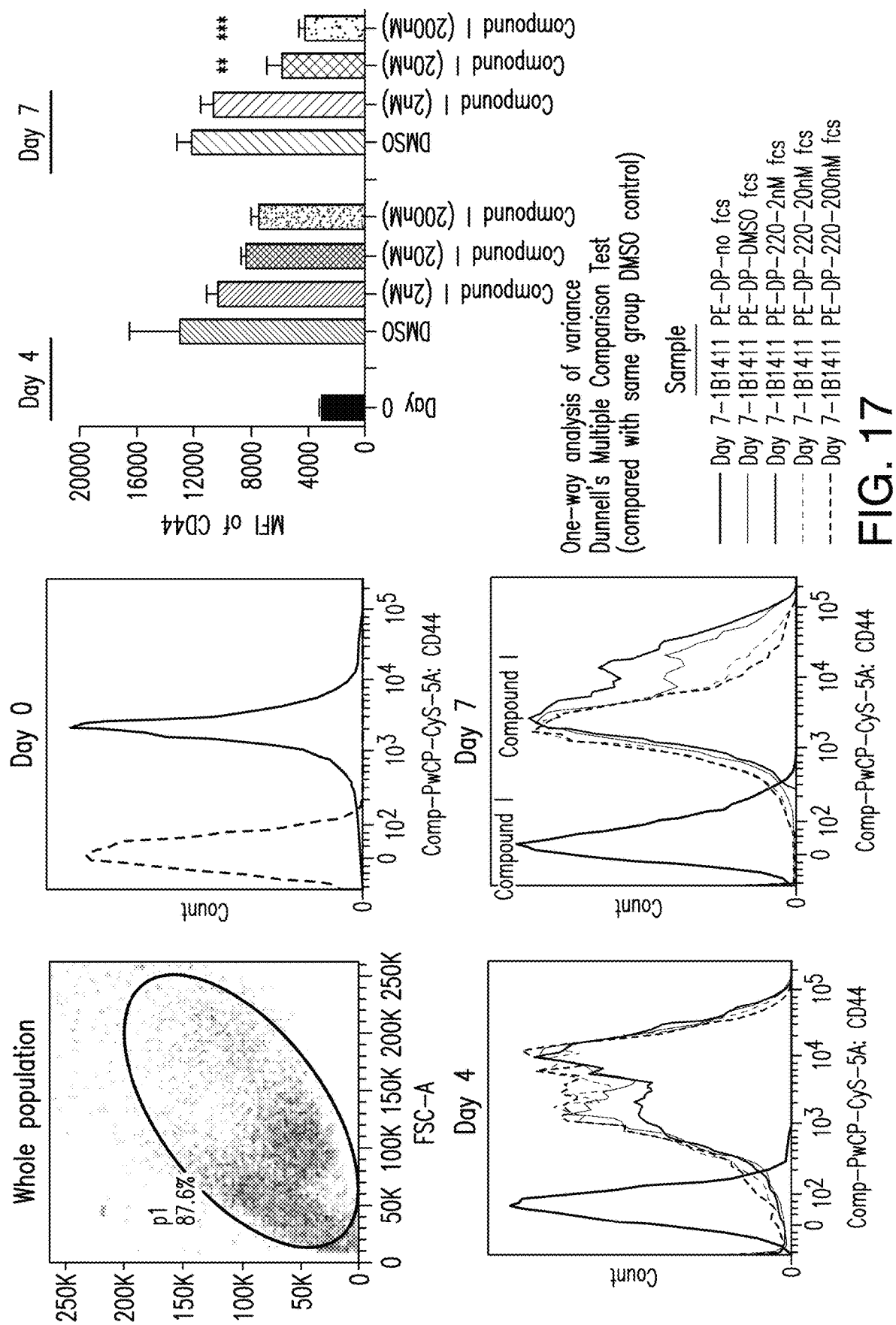
FIG. 17 depicts effect of (S)-3-[4-(4-morphlin-4-ylmethylbenzyloxy)-1-oxo-1,3-dihydro-isoindo-2-yl]piperidine-2,6-dione (represented as compound I in the figure) on CD44 MFI at day 7 B cell differentiation culture.
Figure 18:
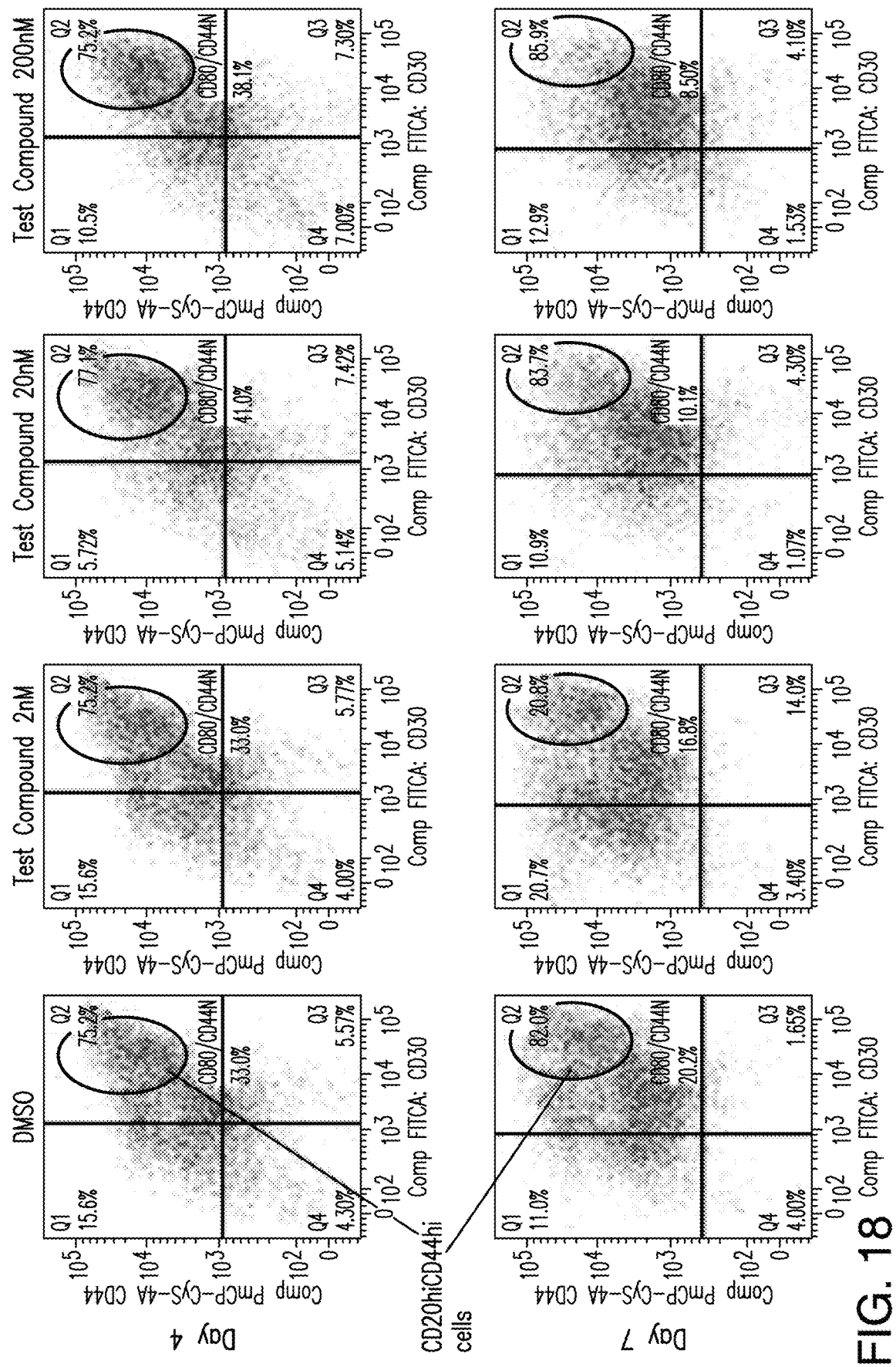
FIG. 18 depicts effect of (S)-3-[4-(4-morphlin-4-ylmethylbenzyloxy)-1-oxo-1,3-dihydro-isoindo-2-yl]piperidine-2,6-dione on $CD20^{high}/CD44^{high}$ cells at day 7 normal B cell differentiation assay.

Using the same B cells in vitro differentiation system, the activity of the test compound on CD44 and CD83 expression in B cell differentiation was further investigated. Multicolor FITC-conjugated anti-CD20 mAb, PerCP Cy5.5-conjugated anti-CD44 mAb and PE-conjugated anti-CD83 mAb are used for day 4 and day 7 cells. The effect of the test compound was evaluated from 3 separate experiments representative of 3 donors. The data indicated that the test compound had dose-dependently and significantly decreased CD44 mean fluorescence intensity (MFI) (FIG. 17, $p<0.01$) in Day 7 B cell differentiation samples, which was due to depletion of $CD20^{high}/CD44^{high}$ cells (FIG. 18).

TABLE 2

Test compound inhibits differentiation of plasmablasts

|  | Day 4 | | Day 7 | |
| --- | --- | --- | --- | --- |
|  | DMSO | Test compound | DMSO | Test compound |
| CD20-CD38++ plasmablasts/plasma cells, % | 25.9 ± 2.4 | 4.8 ± 2.3 | 54.8 ± 5.0 | 9.7 ± 5.4 |
| CD20+CD38+ intermediated cells, % | 14.7 ± 3.1 | 18.3 ± 5.5 | 22.8 ± 5.1 | 23 ± 7.7 |
| CD20+CD38- activated B cells, % | 42.1 ± 1.5 | 57.9 ± 11.5 | 12.5 ± 5.7 | 50.5 ± 8.6 |

Figure 14:
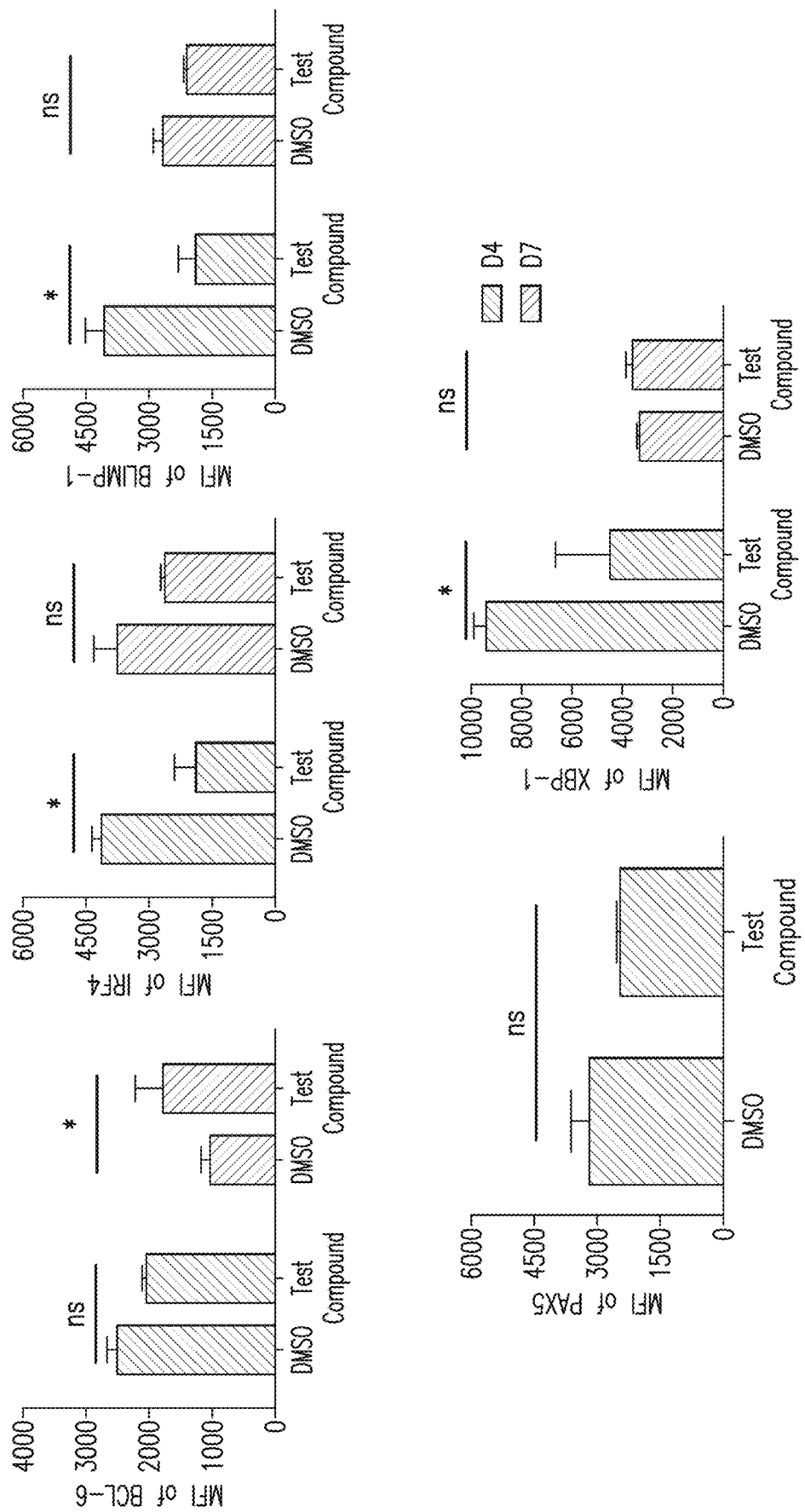
FIG. 14 depicts effect of (S)-3-[4-(4-morphlin-4-ylmethylbenzyloxy)-1-oxo-1,3-dihydro-isoindo-2-yl]piperidine-2,6-dione on plasma cell transcription factors in B cell differentiation culture.
Figure 19:
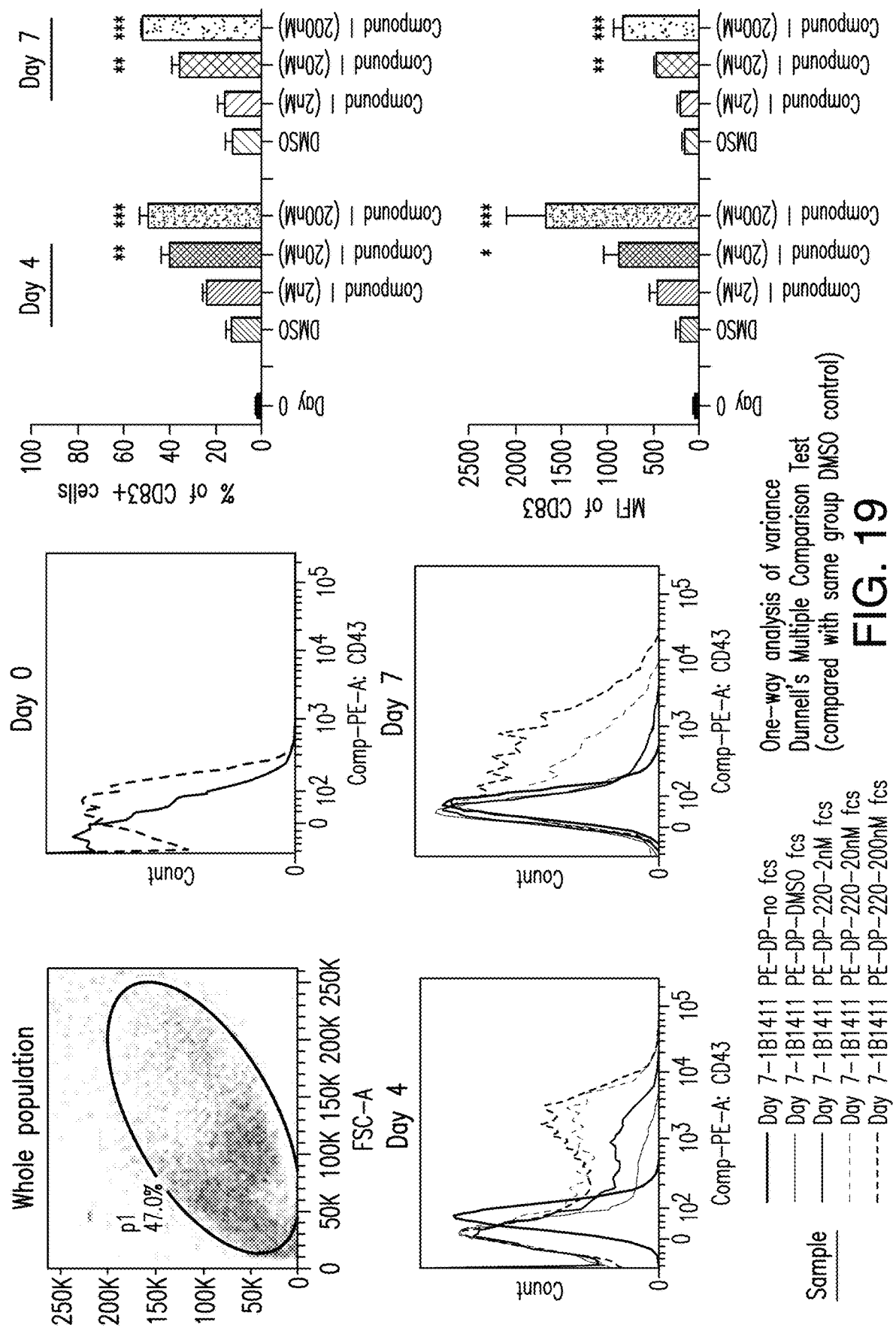
FIG. 19 depicts effect of (S)-3-[4-(4-morphlin-4-ylmethylbenzyloxy)-1-oxo-1,3-dihydro-isoindo-2-yl]piperidine-2,6-dione (represented as compound I in the figure) on CD83+ cells and expression at day 4 and day 7 B cell differentiation culture.

The effect of the test compound on Bcell and plasma cell transcription factor (BCL-6, IRF-4, BLIMP-1, PAX5 and XBP-1) expression was evaluated by flow cytometric method. B cells were cultured as described in above and cells were harvested at day 4, day 7 for immunofluoresence staining. The cells were first stained for CD20 and CD38, and after cell permeabilization, stained for BCL-6, IRF-4, BLIMP-1, PAX5 and XBP-1, then were analyzed by gating on whole lymphocytes. Data from 3 experiments representative of 3 are shown in FIG. 14. The results indicated that the test compound (20 nM) caused a shift in transcription The percentage of $CD20^{high}/CD44^{high}$ cells at Day 7 of the test compound treatment at 2 nM, 20 nM and 200 nM was 18.4%, 10.1% and 6.6% repetitively, compared with the DMSO control of 22.2%. Depletion of CD44+ cells may reduce leukocyte adhesion. The test compound also significantly increased total CD83+ cell population and enhance CD83+ expression (FIG. 19). The percentage of CD83+ cells at Day 4 of the test compound treatment of 2 nM, 20 nM and 200 nM was 24.1%±2.1%, 40.2%±3.6%, 49.5%±4.4% and 18.4%. The percentage of CD83+ cells at Day 7 of the test compound treatment of 2 nM, 20 nM and 200 nM was 16.3%±3.3%, 36.1%±3.4% and 51.9%±0.5%, compared with DMSO at 13.4%±2.4% and 12.9%±3.3 at Day 4 and Day 7 respectively.

Figure 20:
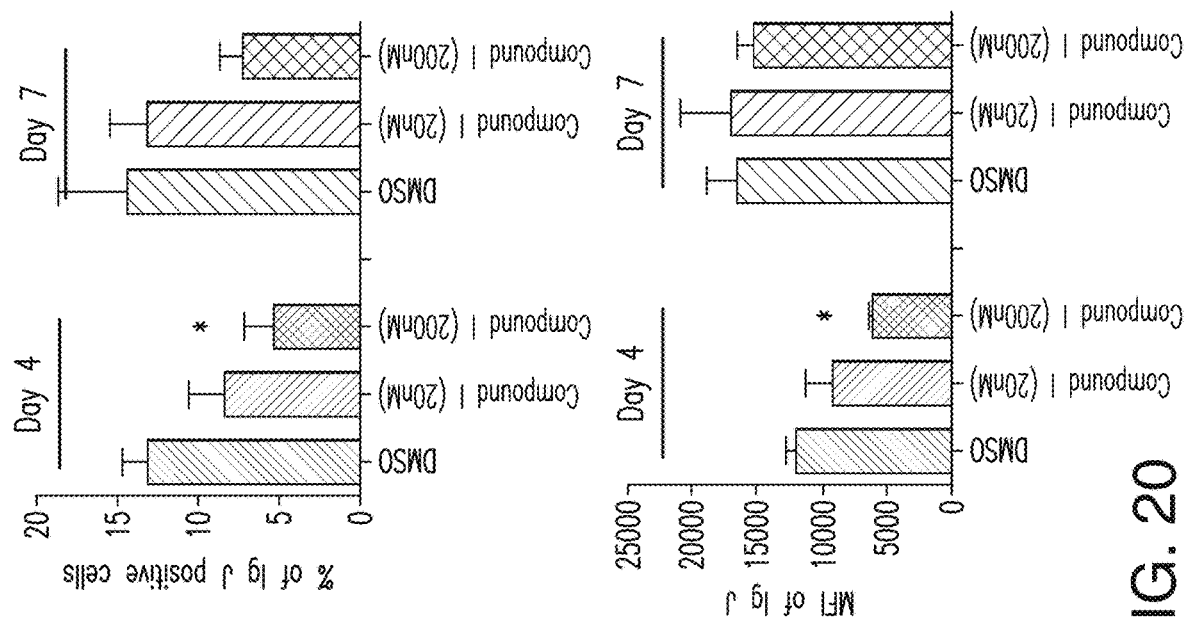
FIG. 20 depicts effect of (S)-3-[4-(4-morphlin-4-ylmethylbenzyloxy)-1-oxo-1,3-dihydro-isoindo-2-yl]piperidine-2,6-dione (represented as compound I in the figure) on Ig J chain expression during B cell differentiation culture.
Figure 20:
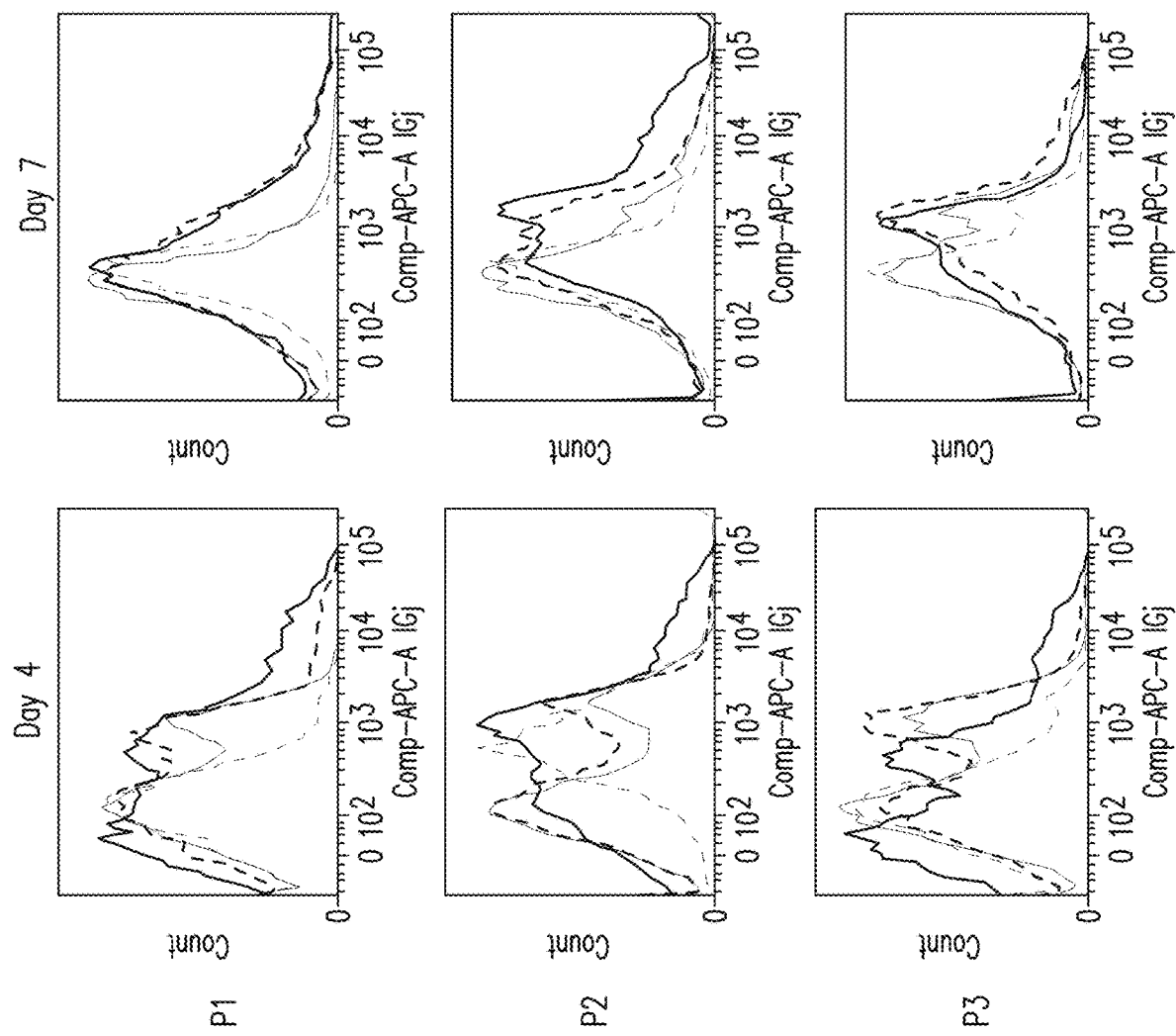

High level IgJ chain expression in rheumatoid arthritis (RA) patients predicts lack of response to rituximab. In order to evaluate if the test compound has any activity on IgJ production, the cells were also used for intracellular staining for IgJ. The results from three donors indicated that the test compound dose-dependently and significantly reduced Ig J chain expression in Day 4 B cell differentiation cultures. It not only reduced the number of IgJ-positive cells (Day 4, 20 nM at 8.4%±1.5%, 200 nM at 5.4%±1.8%; Day 7, 20 nM at 13.2%±2.3% and 200 nM at 7.2%±1.3, respectively, compared with DMSO control at 13.1%±1.5% and 14.4%±4.3 at Day 4 and Day 7 respectively), but also decreased the MFI of IgJ within the positive cells (FIG. 20). Reduced IgJ and IgG, IgM production may be a potential marker of response to the test compound in diseases like RA.

8.4 Example 4: Effect of Test Compounds on Cytokine and Chemokine Production in Anti-Human CD3-Stimulated Human T Cells This example demonstrates the effect of (S)-3-[4-(4-morphlin-4-ylmethylbenzyloxy)-1-oxo-1,3-dihydro-isoindo-2-yl]piperidine-2,6-dione, (R)-3-[4-(4-morphlin-4-ylmethylbenzyloxy)-1-oxo-1,3-dihydro-isoindo-2-yl]piperidine-2,6-dione and 3-[4-(4-morphlin-4-ylmethylbenzyloxy)-1-oxo-1,3-dihydro-isoindo-2-yl]piperidine-2,6-dione on cytokine and chemokine production in anti-human CD3-stimulated human T cells using multiplex Luminex Technology.

The following abbreviations are used:
Abbreviation Explanation or Definition
IL Interleukin
G-CSF Granulocyte Colony Stimulating Factor
GM-CSF Granulocyte Macrophage Colony Stimulating Factor
IFN-γ Interferon Gamma
TNF-α Tumor Necrosis Factor Alpha
RANTES Regulated on Activation, Normal T Cell Expressed and Secreted The following materials were used in this study:
RPMI-1640 Media supplemented with 10% FBS, 100 units/mL penicillin, 100 mg/mL streptomycin and 2 mM L-glutamine (Life Technologies)
RosetteSep® Human T-Cell Enrichment Cocktail (Stem-Cell, Cat #15061)
Luminex Human Cytokine/Chemokine 12-Plex Kit (Millipore, Cat #MPXHCYTO-60K-12)
Luminex IS100 instrument (Millipore)
Anti-human CD3 antibody, OKT3 clone (eBioscience, Cat #16-0037-85)

The test compounds were prepared as stock solutions of 4 mM in DMSO. T cells were isolated from buffy coat by negative selection using the RosetteSep® T Cell Enrichment Cocktail according to manufacturer's procedures.

All 96-well plates were pre-coated with 3 g/mL anti-human CD3 antibody in 100 μL 1×PBS for 4 hours at 37° C. The plates were washed 3 times with RPMI-1640 Complete Media prior to the T cell assay. The T cells were then plated in anti-CD3-pre-coated plates at a density of $2.5 \times 10^5$ cells/well in 180 μL RPMI-1640 Complete Media. The cells were treated with 20 μL 10× titrated test compounds at 10, 1, 0.1, 0.01, 0.001, 0.0001, and 0.00001 μM in duplicate. The final DMSO concentrations were 0.25%. The plates were incubated for 48 hours at 37° C., 5% $CO_2$.

After 48 hours, the supernatants were harvested and tested by a multiplex cytometric bead array (CBA) assay for the following cytokines/chemokines: IL-2, IL-3, IL-5, IL-10, IL-13, IL-15, IL-17A, GM-CSF, G-CSF, IFN-γ, TNF-α, and RANTES.

The CBA plates were analyzed on the Luminex IS100 instrument.

Data from each donor was graphed using GraphPad Prism 5.0 software and expressed as mean pg/mL±SEM and % of DMSO control±SEM.

The test compounds demonstrated immunomodulatory activity in anti-CD3 stimulated primary human T cells, altering the production of several cytokines and chemokines. Baseline levels of cytokines and chemokines produced by stimulated human T cells incubated with vehicle are presented in Table 3 below.

TABLE 3

Baseline levels of cytokines and chemokines

| Cytokine/Chemokine | Baseline Amount Produced (pg/mL) |
|---|---|
| IL-2 | 31 |
| IL- | 38 |
| IL-5 | 27 |
| IL-10 | 449 |
| IL-13 | 205 |
| IL-17A | 19 |
| GM-CSF | 132 |
| IFN-γ | 1271 |
| TNF-α | 411 |
| RANTES | 314 |

Figure 21:
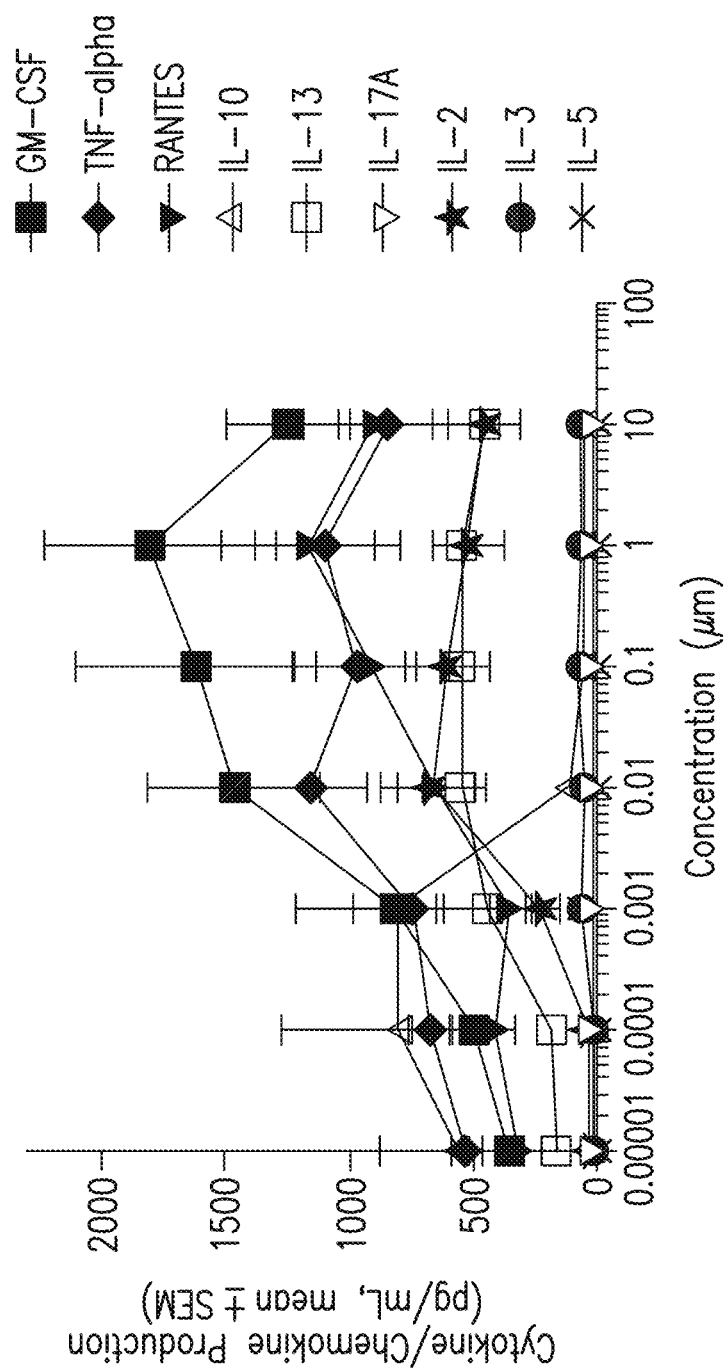
FIG. 21 illustrates the effect of 3-[4-(4-morphlin-4-ylmethylbenzyloxy)-1-oxo-1,3-dihydro-isoindo-2-yl]piperidine-2,6-dione on production of certain cytokines and chemokines in anti-CD3-stimulated human T cells, expressed as absolute amount produced.
Figure 22:
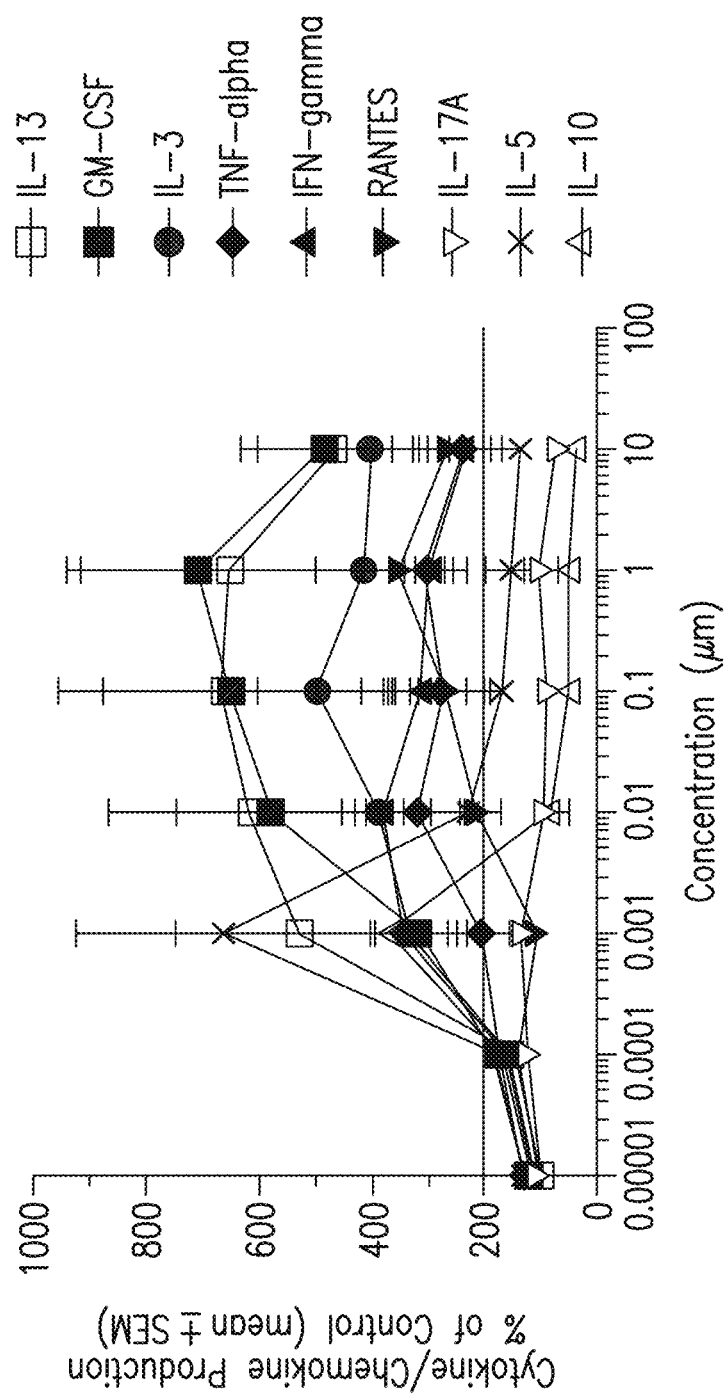
FIG. 22 illustrates the effect of 3-[4-(4-morphlin-4-ylmethylbenzyloxy)-1-oxo-1,3-dihydro-isoindo-2-yl]piperidine-2,6-dione on production of certain cytokines and chemokines in anti-CD3-stimulated human T cells, expressed as percentage of control.
Figure 23:
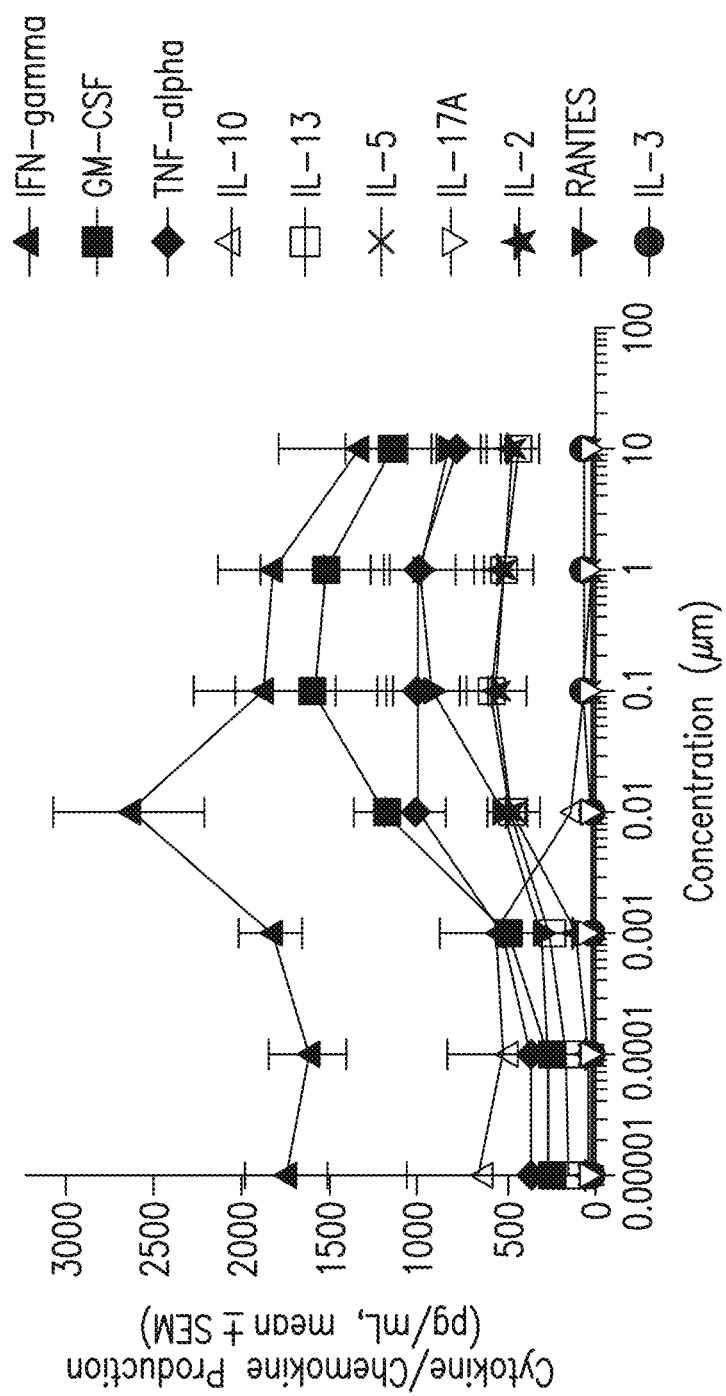
FIG. 23 illustrates the effect of (R)-3-[4-(4-ylmethylbenzyloxy)-1-oxo-1,3-dihydro-isoindo-2-yl]piperidine-2,6-dione on production of certain cytokines and chemokines in anti-CD3-stimulated human T cells, expressed as absolute amount produced.
Figure 24:
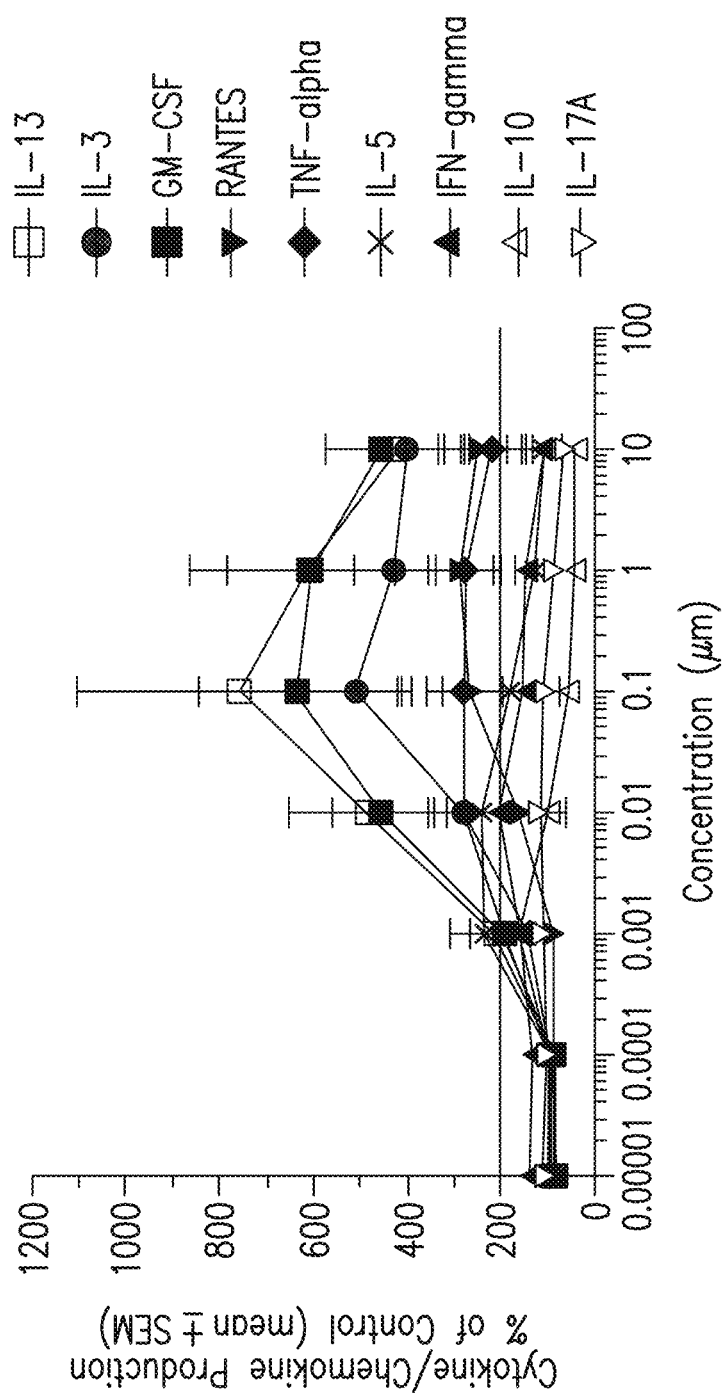
FIG. 24 illustrates the effect of (R)-3-[4-(4-ylmethylbenzyloxy)-1-oxo-1,3-dihydro-isoindo-2-yl]piperidine-2,6-dione on production of certain cytokines and chemokines in anti-CD3-stimulated human T cells, expressed as percentage of control.
Figure 25:
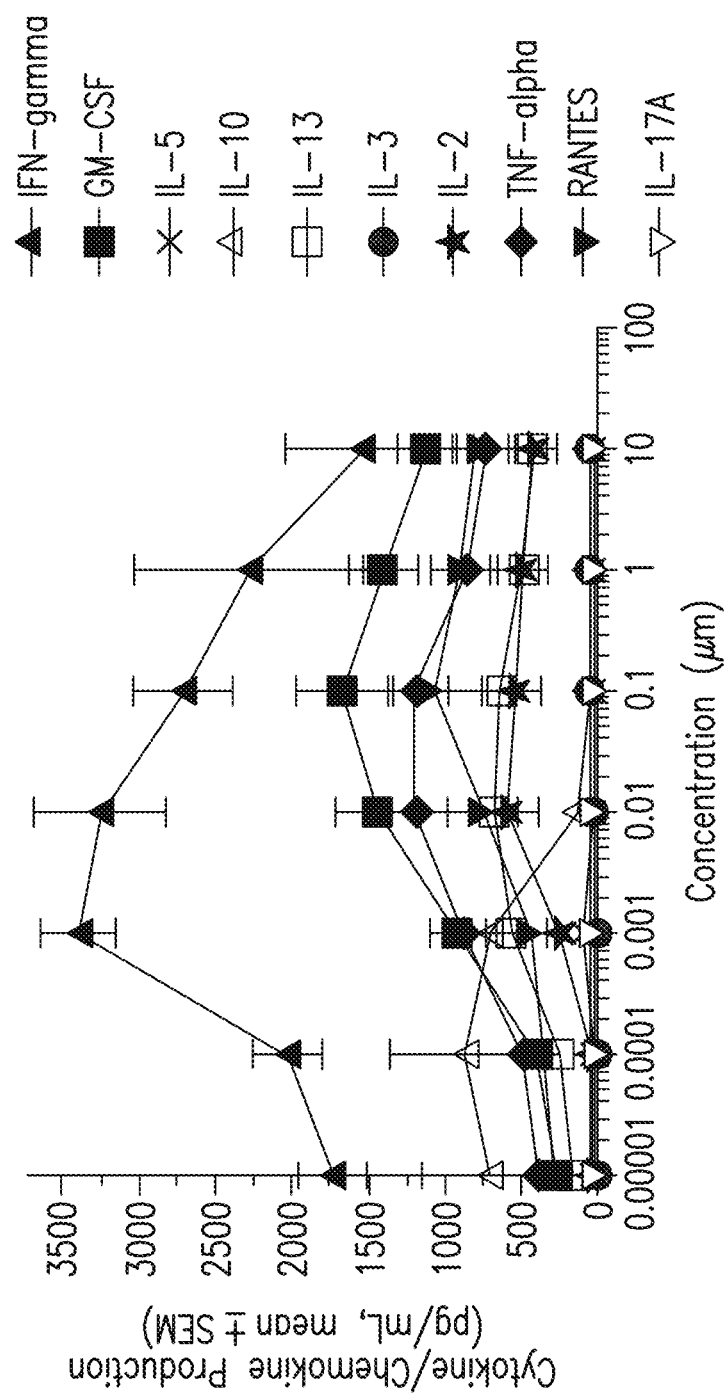
FIG. 25 illustrates the effect of (S)-3-[4-(4-ylmethylbenzyloxy)-1-oxo-1,3-dihydro-isoindo-2-yl]piperidine-2,6-dione on production of certain cytokines and chemokines in anti-CD3-stimulated human T cells, expressed as absolute amount produced.
Figure 26:
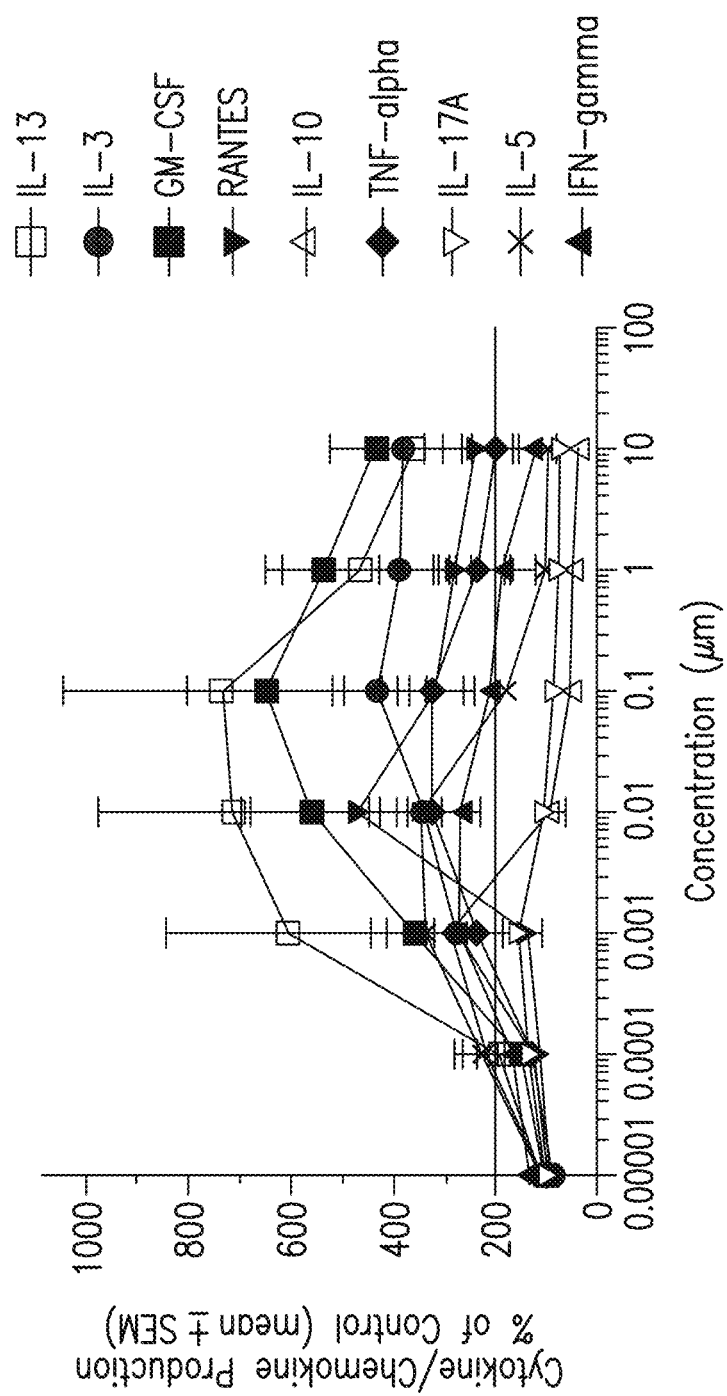
FIG. 26 illustrates the effect of (S)-3-[4-(4-ylmethylbenzyloxy)-1-oxo-1,3-dihydro-isoindo-2-yl]piperidine-2,6-dione on production of certain cytokines and chemokines in anti-CD3-stimulated human T cells, expressed as percentage of control.

The test compounds enhanced IL-2, IL-3, IL-5, IL-10, IL-13, GM-CSF, IFN-γ, RANTES, and TNF-α production in stimulated human T cells. The enhancement of production by test compounds was largely concentration-dependent for most of the cytokines and chemokines, except for IL-10 and IL-5. The test compounds enhanced IL-10 production at lower concentrations but inhibited enhancement of IL-10 production at higher concentrations. The test compounds enhanced IL-5 production primarily at a single concentration within the range of concentrations that increased production of other cytokines. Relatively small amounts of IL-2, IL-3, IL-5, and IL-17A were produced in control cells in comparison with other cytokines and chemokines (Table 1). Production of IL-17A did not change much by test compounds. Measurable quantities of GCSF and IL-15 were not produced in stimulated human T cells. The effect of 3-[4-(4-morpholin-4-ylmethylbenzyloxy)-1-oxo-1,3-dihydro-isoindo-2-yl]piperidine-2,6-dione on cytokine and chemokine production in anti-CD3-stimulated human T cells, expressed as absolute amount produced and as percentage of vehicle control cells are provided in FIGS. 21 and 22, respectively. The effect of (R)-3-[4-(4-morpholin-4-ylmethylbenzyloxy)-1-oxo-1,3-dihydro-isoindo-2-yl]piperidine-2, 6-dione on cytokine and chemokine production in anti-CD3-stimulated human T cells, expressed as absolute amount produced and as percentage of vehicle control cells are provided in FIGS. 23 and 24, respectively. The effect of (S)-3-[4-(4-morpholin-4-ylmethylbenzyloxy)-1-oxo-1,3-dihydro-isoindo-2-yl]piperidine-2,6-dione on cytokine and chemokine production in anti-CD3-stimulated human T cells, expressed as absolute amount produced and as percentage of vehicle control cells are provided in FIGS. 25 and 26, respectively. The dashed line denotes the level equivalent to double the baseline production ($EC_{200}$) in FIGS. 22, 24 and 26.

8.5 Example 5: Anti-Inflammatory Activity

Anti-inflammatory activities of 3-[4-(4-morpholin-4-ylmethyl-benzyloxy)-1-oxo-1,3-dihydro-isoindol-2-yl]-piperidine-2,6-dione, (R)-3-[4-(4-morpholin-4-ylmethyl-benzyloxy)-1-oxo-1,3-dihydro-isoindol-2-yl]-piperidine-2,6-dione and (S)-3-[4-(4-morphlin-4-ylmethylbenzyloxy)-1-oxo-1,3-dihydro-isoindo-2-yl]piperidine-2,6-dione were studied in human peripheral blood mononuclear cells (hPBMC). Luminex Technology was used to determine the inhibitory (enhancement) concentration, $IC_{50}$ for the compounds for the simultaneous profiling of pro-inflammatory cytokines/chemokines and IL-10 (anti-inflammatory cytokine) from LPS-stimulated healthy human donor PBMCs.

50 ml Buffy coat from healthy donors was obtained from Blood Center of New Jersey (East Orange, N.J.). Lipopolysaccharide (strain)(Cat #L-1887) was purchased from Sigma. Milliplex kits with antibody bound beads for Luminex xMAP Technology was purchased from Millipore (Billerica, Mass.) and combined into multiplex format prior to assay.

8.5.1 Purification of Human Peripheral Blood Mononuclear Cells 50 ml human buffy coat was aliquoted 25 ml each into two 50 ml conical tubes and 25 ml sterile HBSS was added to each conical tube. The tubes were gently mixed by inverting. Fifteen ml of room temperature Ficoll-Paque Plus (GE Healthcare (location); cat #17-1440-02) was aliquoted into four 50 ml conical tubes. Then 25 ml of the Buffy coat/HBSS mixture was layered gently and slowly on top of the Ficoll. The samples were centrifuged at 450 rpm for 35 minutes. The top layered containing plasma was pipetted off and discarded. The interface containing mononuclear cells was transferred into two 50 ml conical tubes. Both conical tubes were filled to total volume of 50 ml with HBSS and centrifuged at 1200 rpm for 10 minutes. The cells were washed again in HBSS and spun at 1000 rpm for 10 minutes. Cell pellet was resuspended with 20 ml RPMI complete medium (RPMI/5% human sera/1× pen/strep/glut) and counted.

8.5.2 Treatment of Human Peripheral Blood Mononuclear Cells

One hundred μl (2×106/ml) of hPBMCs were added to each well of a 96 well flat-bottom plate (final cell count=2× 105/well) and incubated at 37° C. for 1 hour. Twenty (10×) compound was added to each test well and twenty μl medium containing 2.5% DMSO was added to each control well ([DMSO]final=0.25%) and plate was incubated for 1 hour at 37° C. Cells were then stimulated with 80 of 2.5 ng/ml LPS ([LPS]final=1 ng/ml) and incubated for 18 hours at 37° C.

50 μl supernatant from each well was transferred into 3 new round-bottomed 96 well plates and stored at −20° C. for Luminex analysis. Duplicate wells were performed for each sample.

8.5.3 Luminex Analysis

Supernatant samples were analyzed for cytokines in multiplex format according to the manufacturer's instructions (Millipore, Billerica, Ma 01821) using a Luminex IS100 instrument. IL-12 and GM-CSF analyses were done in a two-plex format using neat supernatants while all other cytokines were done in a multiplex format using supernatants diluted 1:20. Data analysis was performed using Upstate Beadview software. $IC_{50}$s were calculated using non-linear regression, sigmoidal dose-response, constraining the top to 100% and bottom to 0%, allowing variable slope. The $EC_{50}$s were based on the upper constraint of the sigmoidal curves equaling 246.9%, representing the average IL-10 enhancement produced by pomalidomide (control) at 10 μM and the lower constraint to 100%. The $IC_{50}$ were performed using GraphPad Prism v5.00. The data values represent the mean±SEM (standard error of the mean) of n (number of experiments in duplicate).

Figure 27:
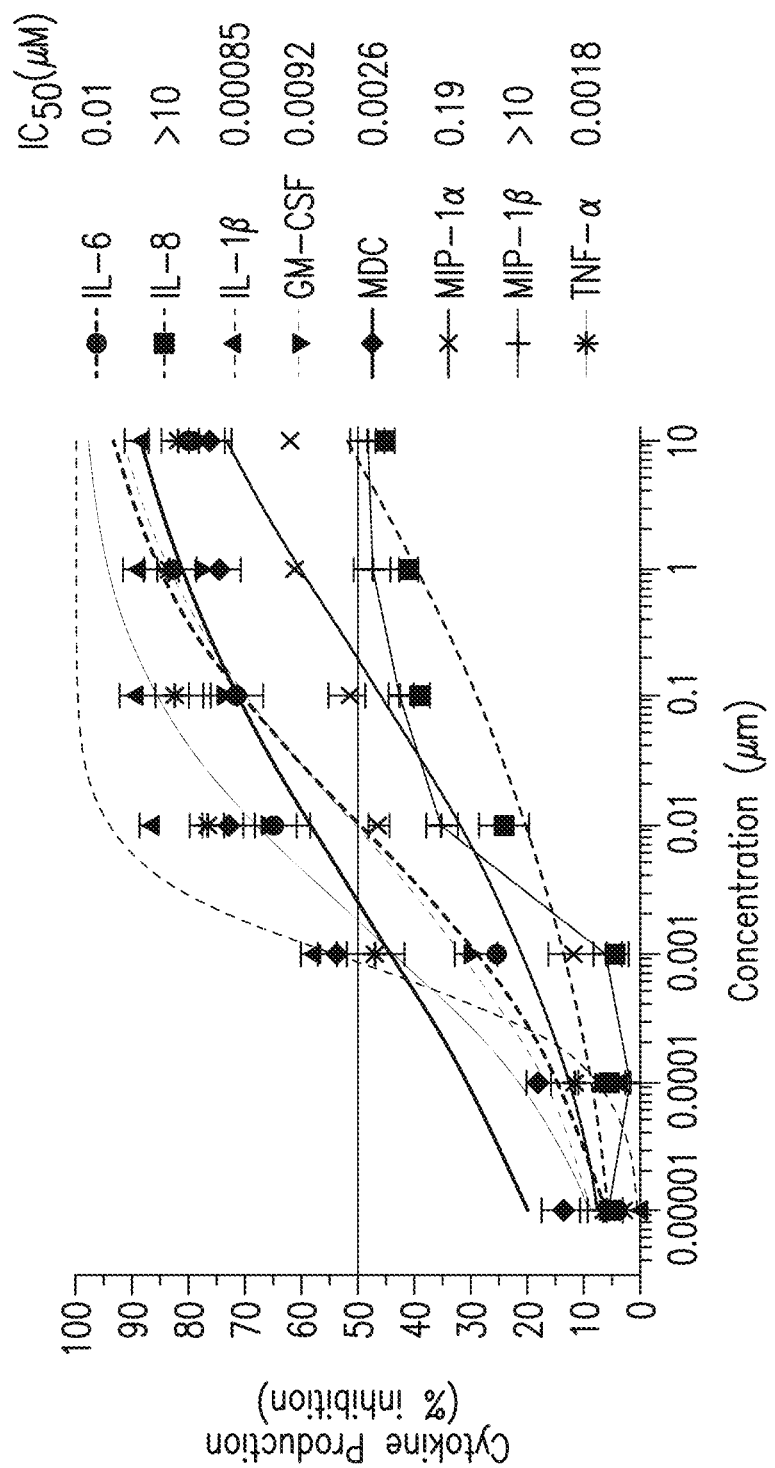
FIG. 27 illustrates inhibition of production of certain cytokines and chemokines in lipopolysaccharide-stimulated peripheral blood mononuclear cells by 3-[4-(4-morphlin-4-ylmethylbenzyloxy)-1-oxo-1,3-dihydro-isoindo-2-yl]piperidine-2,6-dione.
Figure 28:
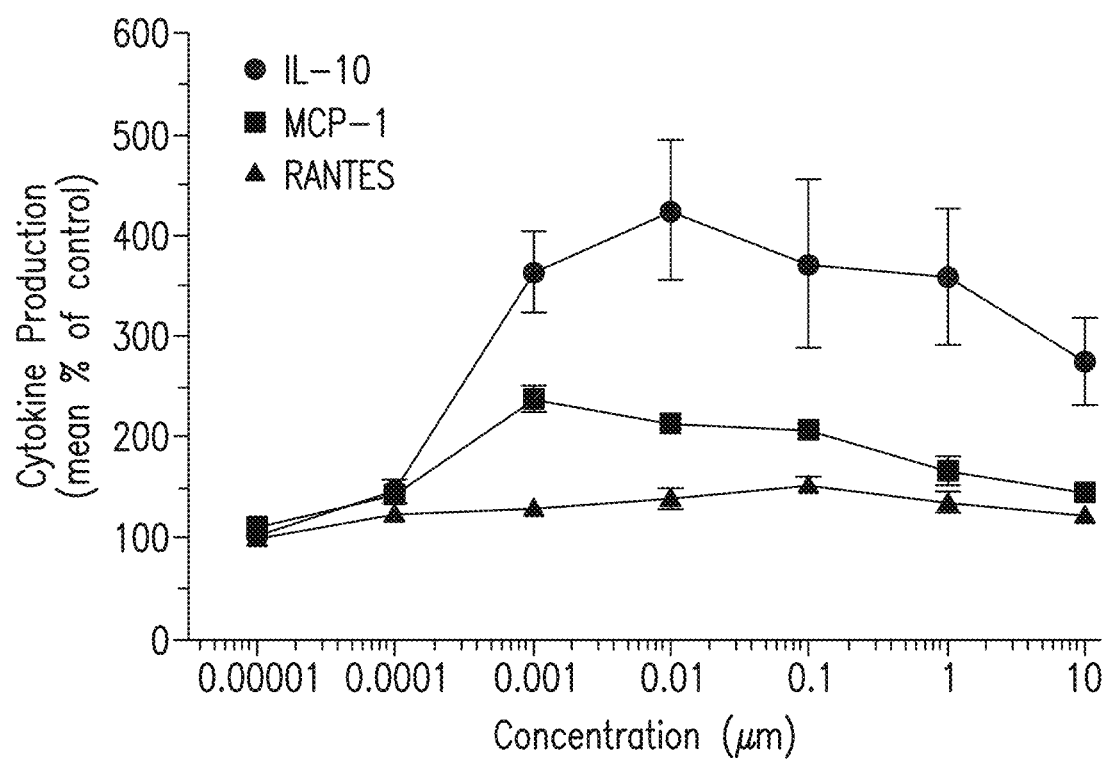
FIG. 28 illustrates enhancement of on production of certain cytokines and chemokines in lipopolysaccharide-stimulated peripheral blood mononuclear cells by 3-[4-(4-morphlin-4-ylmethylbenzyloxy)-1-oxo-1,3-dihydro-isoindo-2-yl]piperidine-2,6-dione.
Figure 29:
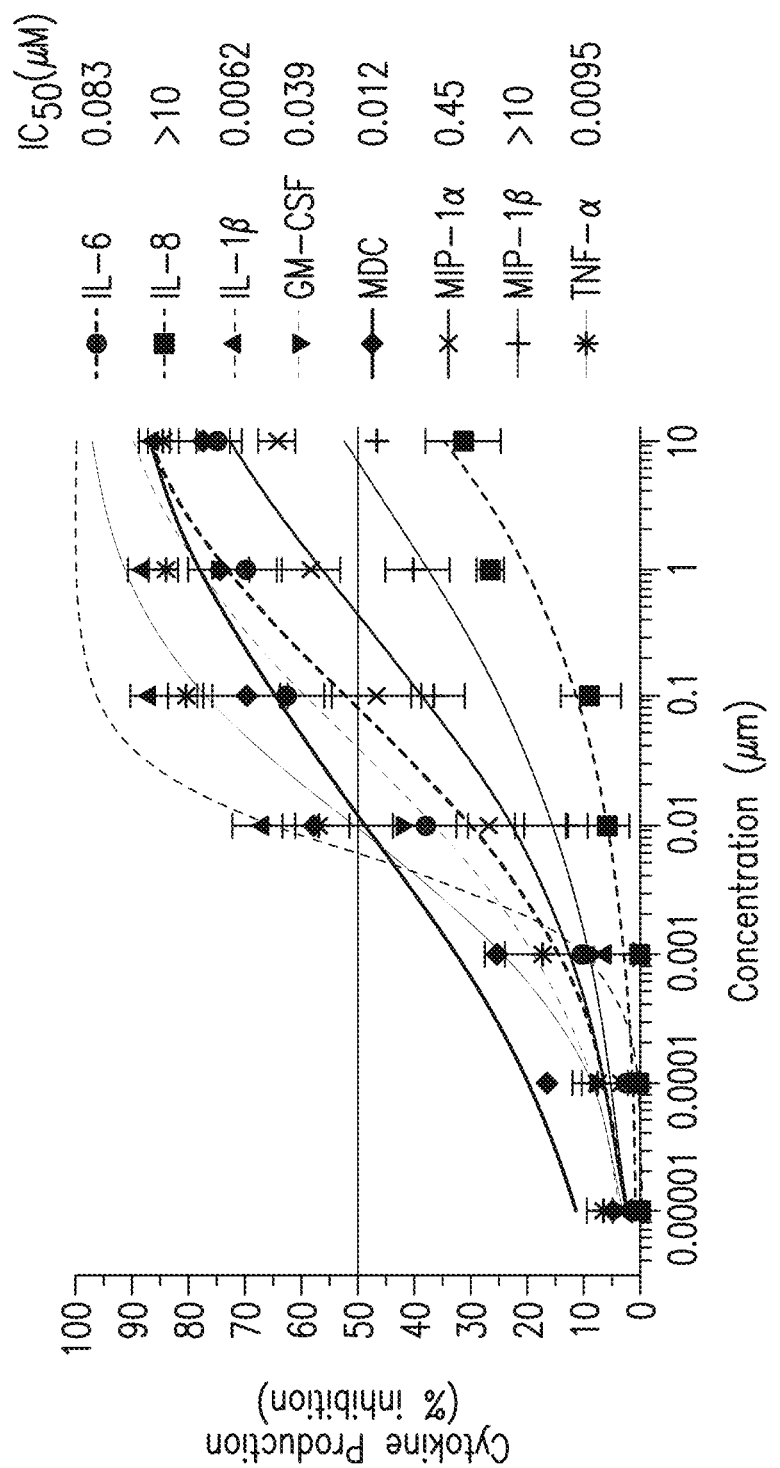
FIG. 29 illustrates inhibition of on production of certain cytokines and chemokines in lipopolysaccharide-stimulated peripheral blood mononuclear cells by (R)-3-[4-(4-morphlin-4-ylmethylbenzyloxy)-1-oxo-1,3-dihydro-isoindo-2-yl]piperidine-2,6-dione.
Figure 30:
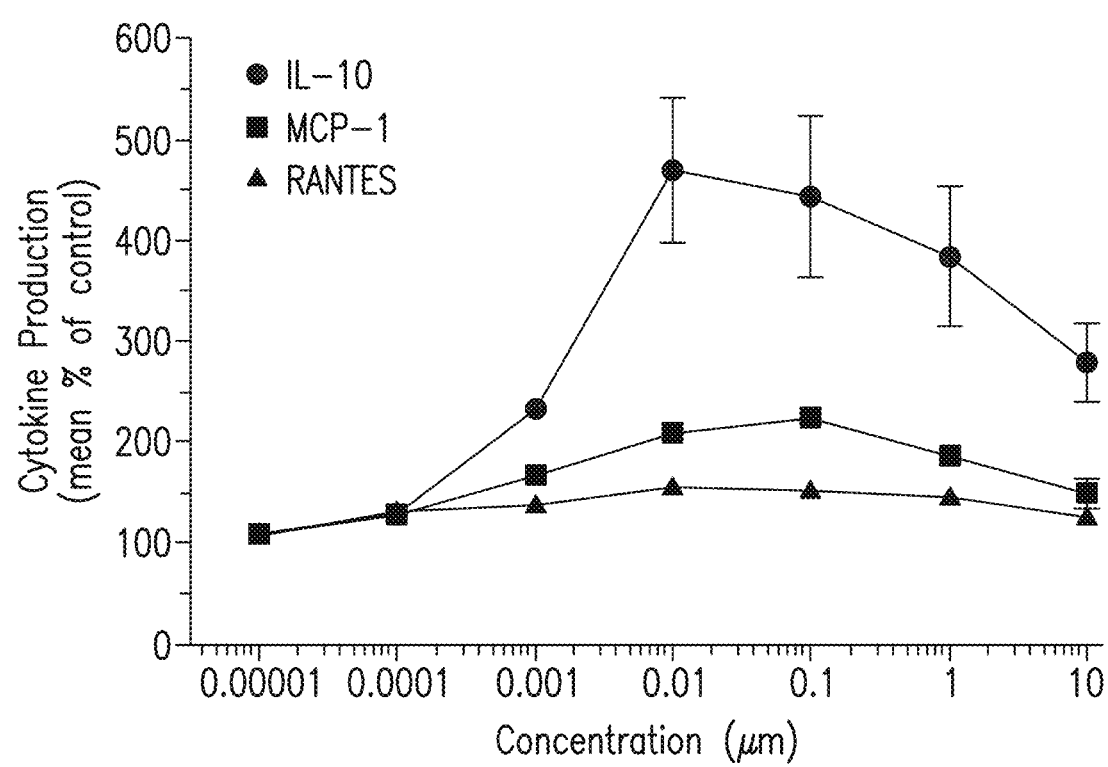
FIG. 30 illustrates enhancement of on production of certain cytokines and chemokines in lipopolysaccharide-stimulated peripheral blood mononuclear cells by (R)-3-[4-(4-morphlin-4-ylmethylbenzyloxy)-1-oxo-1,3-dihydro-isoindo-2-yl]piperidine-2,6-dione.
Figure 31:
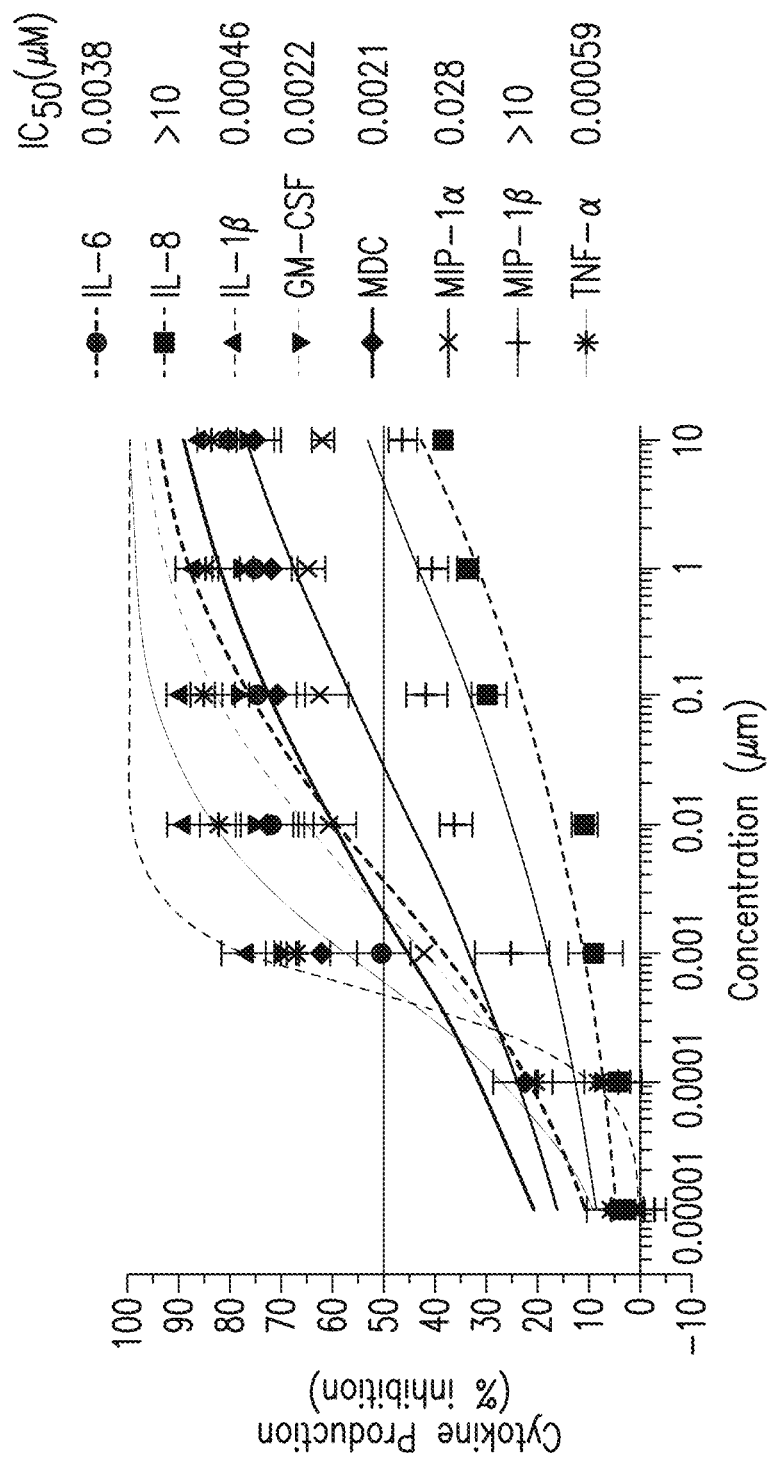
FIG. 31 illustrates inhibition of on production of certain cytokines and chemokines in lipopolysaccharide-stimulated peripheral blood mononuclear cells by (S)-3-[4-(4-morphlin-4-ylmethylbenzyloxy)-1-oxo-1,3-dihydro-isoindo-2-yl]piperidine-2,6-dione.
Figure 32:
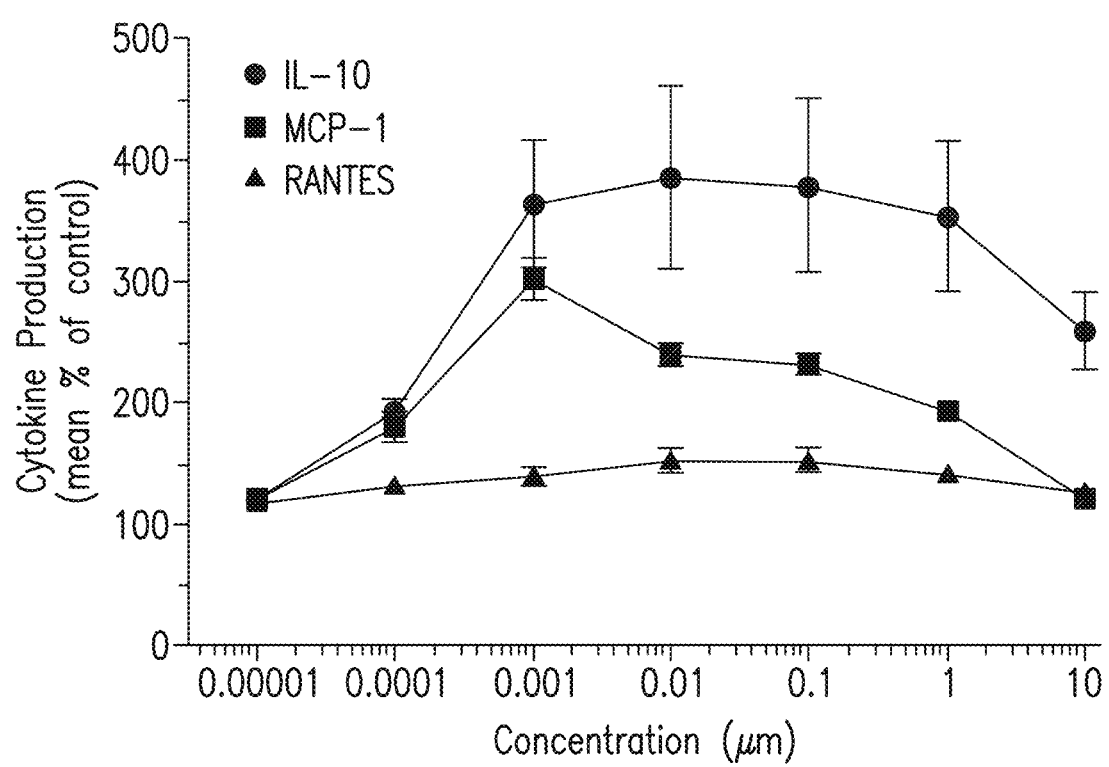
FIG. 32 illustrates enhancement of on production of certain cytokines and chemokines in lipopolysaccharide-stimulated peripheral blood mononuclear cells by (S)-3-[4-(4-morphlin-4-ylmethylbenzyloxy)-1-oxo-1,3-dihydro-isoindo-2-yl]piperidine-2,6-dione.
Figure 33:
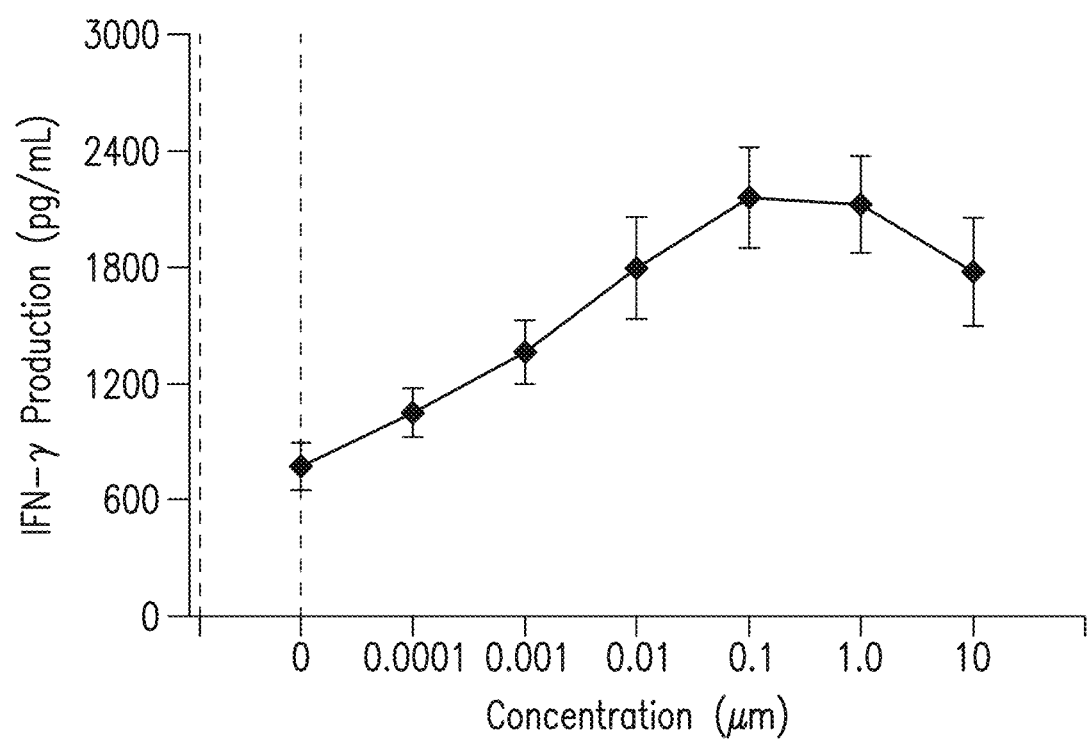
FIG. 33 illustrates enhancement of NK cell IFN-gamma production in response to immobilized IgG and IL-2, expressed as absolute amount produced, by 3-[4-(4-morphlin-4-ylmethylbenzyloxy)-1-oxo-1,3-dihydro-isoindo-2-yl]piperidine-2,6-dione.
Figure 34:
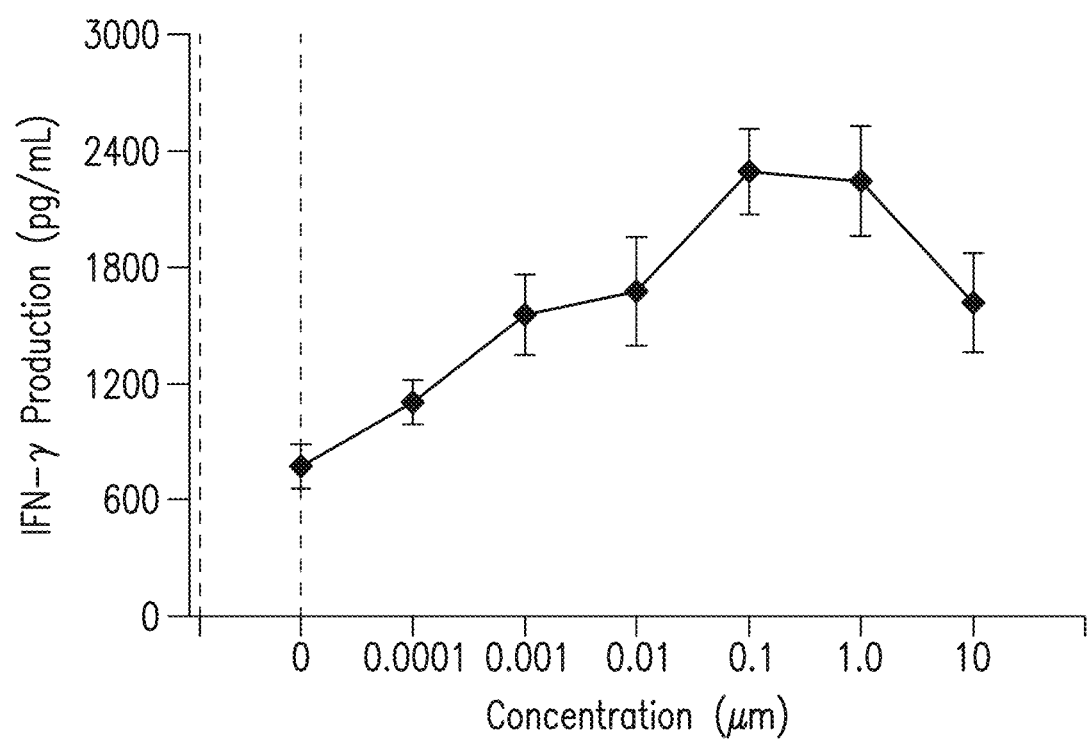
FIG. 34 illustrates enhancement of NK cell IFN-gamma production in response to immobilized IgG and IL-2, expressed as absolute amount produced, by (R)-3-[4-(4-morphlin-4-ylmethylbenzyloxy)-1-oxo-1,3-dihydro-isoindo-2-yl]piperidine-2,6-dione.
Figure 35:
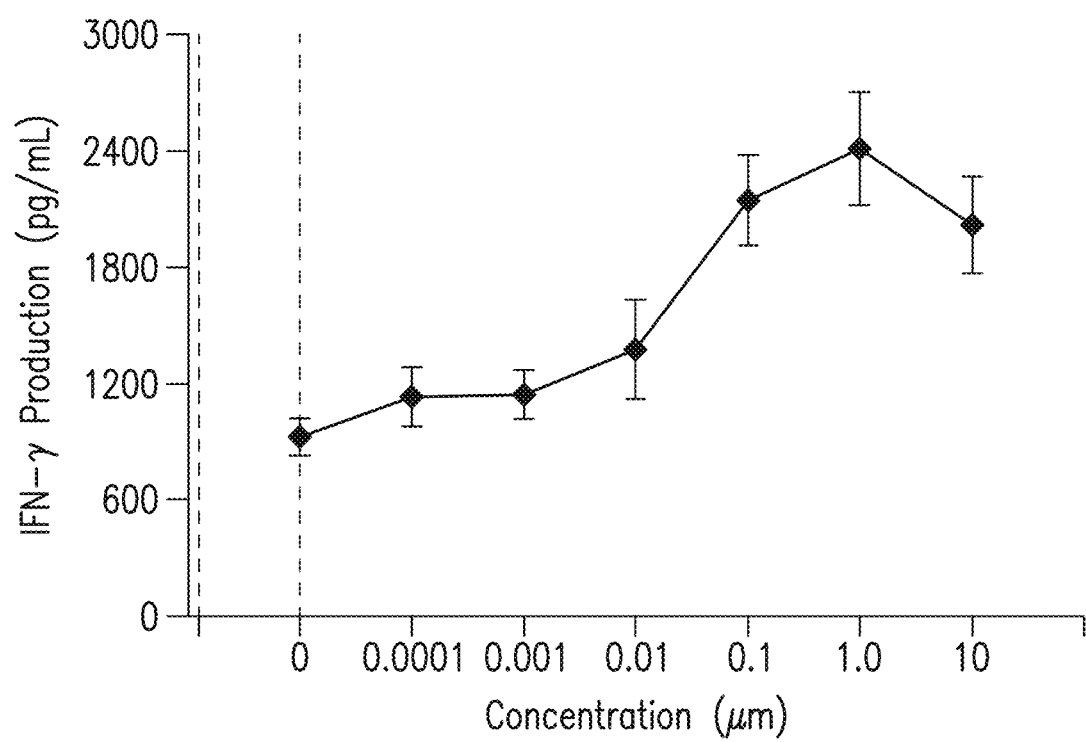
FIG. 35 illustrates enhancement of NK cell IFN-gamma production in response to immobilized IgG and IL-2, expressed as absolute amount produced, by (S)-3-[4-(4-morphlin-4-ylmethylbenzyloxy)-1-oxo-1,3-dihydro-isoindo-2-yl]piperidine-2,6-dione.

As demonstrated by data in Table 4 below and FIGS. 27, 29 and 31, test compounds have varied potencies for the inhibitions of the multiple cytokines examined, e.g., Il-6, IL-8, IL-10, GM-CSF, MDC, MIP-1α, MIP-1β, and TNF-α, in general. Also, these compounds enhanced production of IL-10, MCP-1, and RANTES with various potencies as provided in Table 5 and FIGS. 28, 30 and 32.

TABLE 4

Summary of Cytokine Inhibitory Profile of Test Compounds

| Cytokine | Racemate $IC_{50}$ (μM) | R-enantiomer $IC_{50}$ (μM) | S-enantiomer $IC_{50}$ (μM) |
|---|---|---|---|
| IL-6 | 0.01 | 0.083 | 0.0038 |
| IL-8 | >10 | >10 | >10 |
| IL-1β | 0.00085 | 0.0062 | 0.00046 |
| GM-CSF | 0.0092 | 0.039 | 0.0022 |
| MDC | 0.0026 | 0.012 | 0.0021 |
| MIP-1α | 0.19 | 0.45 | 0.028 |
| MIP-1β | >10 | >10 | >10 |
| TNF-α | 0.0018 | 0.0095 | 0.00059 |

TABLE 5

Cytokine Profile Summary of-Mean % of Control at 0.1 μM

| Cytokine | Racemate (% of control) | R-enantiomer (% of control) | S-enantiomer (% of control) |
|---|---|---|---|
| IL-10 | 371 | 442 | 379 |
| MCP-1 | 208 | 223 | 233 |
| RANTES | 153 | 151 | 153 |

8.6 Example 6: Effect on Human Natural Killer (NK) Cell Function in Response to Igg/Rituximab In this example, the capacity of test compounds to enhance human NK cell function in response to IgG/Rituximab was studied. The immunomodulatory activity of the test compounds was compared in two assays of natural killer (NK) cell functions (1) IgG- and IL-2-induced interferon-gamma (IFN-γ) production.

The materials used in the study and their sources are provided below:
- Buffy Coat from healthy volunteers (Blood Center of New Jersey)
- Ficoll-Hypaque Plus (Fisher Scientific Co LLC, PA, Cat #17144002)
- RPMI-1640 Medium supplemented with 10% FBS (fetal bovine serum), 100 units/mL penicillin,
- 100 mg/mL streptomycin, and 2 mM L-glutamine (Invitrogen, Cat #21870-076)
- RPMI-1640 Medium (without phenol red) supplemented with 10% FBS, 100 units/mL penicillin,
- 100 mg/mL streptomycin, and 2 mM L-glutamine (Invitrogen, Cat #11835-030)

Rituximab (Rituxan, Roche, Inc.) (Cat No. DIN 02241927, Lot No. B50177)
Human AB+ serum (Gemini Bio Products, CA, Cat #100-512)
CytoTox 96 Non-Radioactive Cytotoxicity Assay Kit (Promega, WI, Cat #G1780)
RosetteSep Human NK Cell Enrichment Cocktail (Stem Cell Technologies, Vancouver, BC, Cat #15065)
Mouse anti-human CD56+ conjugated APC (BD Biosciences, CA, Cat #555518)
Human Immunoglobulin G from Serum (IgG) (Sigma, St. Louis, Mo.; Cat #I2511-10MG)
Human Recombinant IL-2 (R&D Systems, MN, Cat #202-IL-050/CF)
Human IFN-gamma ELISA Kit (ThermoFisher, Cat #PIEHIFNG5)
The following cell lines were used:
Activated B cell-like—diffuse large B cell lymphoma (ABC-DLBCL): Riva cells (NCI, MD)
Germinal center B-cell-like—diffuse large B cell lymphoma (GCB-DLBCL):
WSU-DLCL2 (Celgene Signal, CA)
Farage (ATCC, VA)
Follicular lymphoma: DoHH2 (DSMZ, Germany)
Burkitt's lymphoma (BL): Raji (ATCC, VA).

NK cells from healthy donors were isolated from buffy coat blood by negative selection using the RosetteSep NK cell enrichment cocktail (Stem Cell Technologies, Vancouver, BC) prior to Ficoll-Hypaque (Fisher Scientific Co LLC, PA) density gradient centrifugation following the manufacturers' instructions. CD56+NK cells were isolated to ~85% purity, as determined by flow cytometry (BD Biosciences, CA).

8.6.1 NK IgG-Induced Interferon-Gamma (IFN-Gamma) Assay

Ninety-six-well flat-bottom plates were coated with 100 µg/mL of human IgG (Sigma) overnight at 4° C. The next day, unbound IgG was washed away with cold 1×PBS. NK cells were then plated in the IgG-coated 96-well plates at 2×105 cells per well in 180 µL RPMI-1640 Media and 10 ng/mL of rhIL-2 (R & D Systems, MN) was added. Test compounds were added in a volume of 20 µL DMSO. Final concentrations of test compounds were 0.0001, 0.001, 0.01, 0.1, 1, or 10 µM. Final DMSO concentrations were 0.25%. After 48 hours, the supernatants were harvested and analyzed by ELISA for IFN-γ production.

Data used to determine the ability of test compounds to enhance NK cell IFN-γ production in response to immobilized IgG and rhIL-2 stimulation was analyzed for each donor using GraphPad Prism v5.0 software. The data are presented in two ways, (1) as the absolute amount if IFN-γ produced (pg/mL±SEM) and (2) as the percentage of the amount of IFN-γ produced in the presence of 1 µM pomalidomide. The $EC_{50}$ is the concentration of test compound providing half-maximal IFN-γ production, with maximal production defined as the amount of IFN-γ produced in the presence of 1 µM pomalidomide. $EC_{50}$ values were calculated using non-linear regression, sigmoidaldose-response constraining the top to 100% and bottom to 0% allowing for a variable slope.

TABLE 6

| Compound | $EC_{50}$ |
|---|---|
| Racemate | 0.037 µM |
| R-enantiomer | 0.016 µM |
| S-enantiomer | 0.012 µM |

Figure 36:
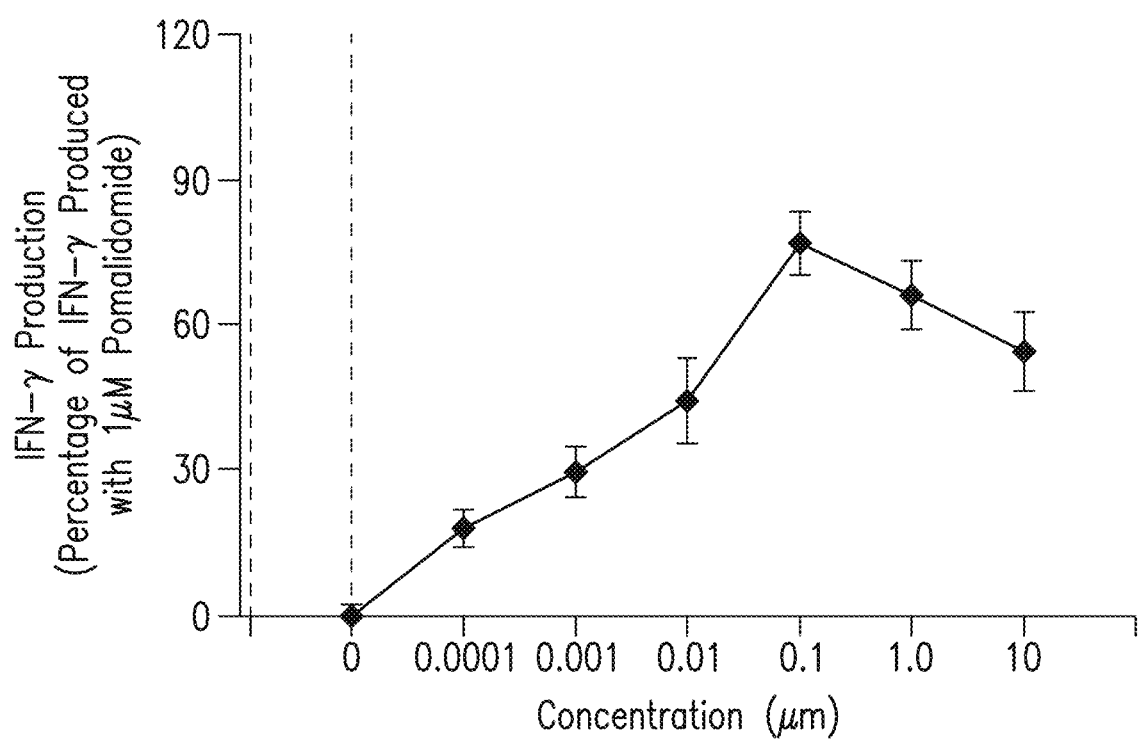
FIG. 36 illustrates enhancement of NK cell IFN-gamma production in response to immobilized IgG and IL-2, expressed as percentage of amount of IFN-gamma produced in the presence of 1 μm pomalidomide, by 3-[4-(4-morphlin-4-ylmethylbenzyloxy)-1-oxo-1,3-dihydro-isoindo-2-yl]piperidine-2,6-dione.
Figure 37:
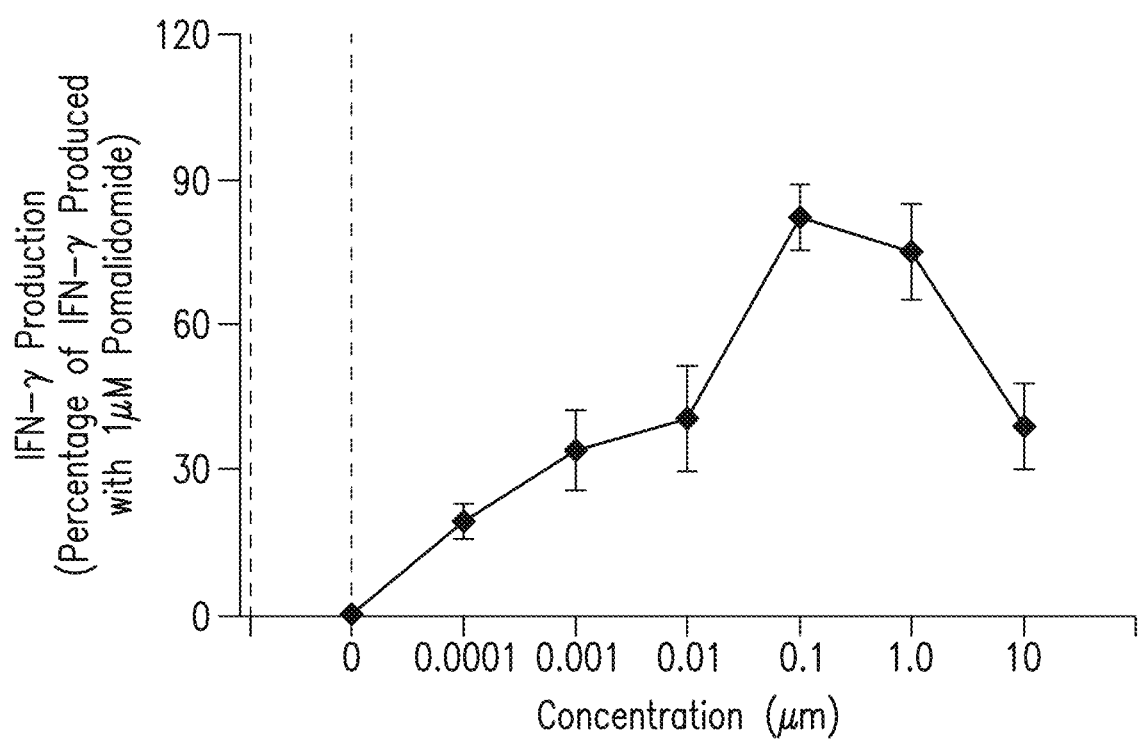
FIG. 37 illustrates enhancement of NK cell IFN-Gamma Production in Response to Immobilized IgG and IL-2, expressed as percentage of amount of IFN-gamma produced in the presence of 1 μm pomalidomide, by (R)-3-[4-(4-morphlin-4-ylmethylbenzyloxy)-1-oxo-1,3-dihydro-isoindo-2-yl]piperidine-2,6-dione.
Figure 38:
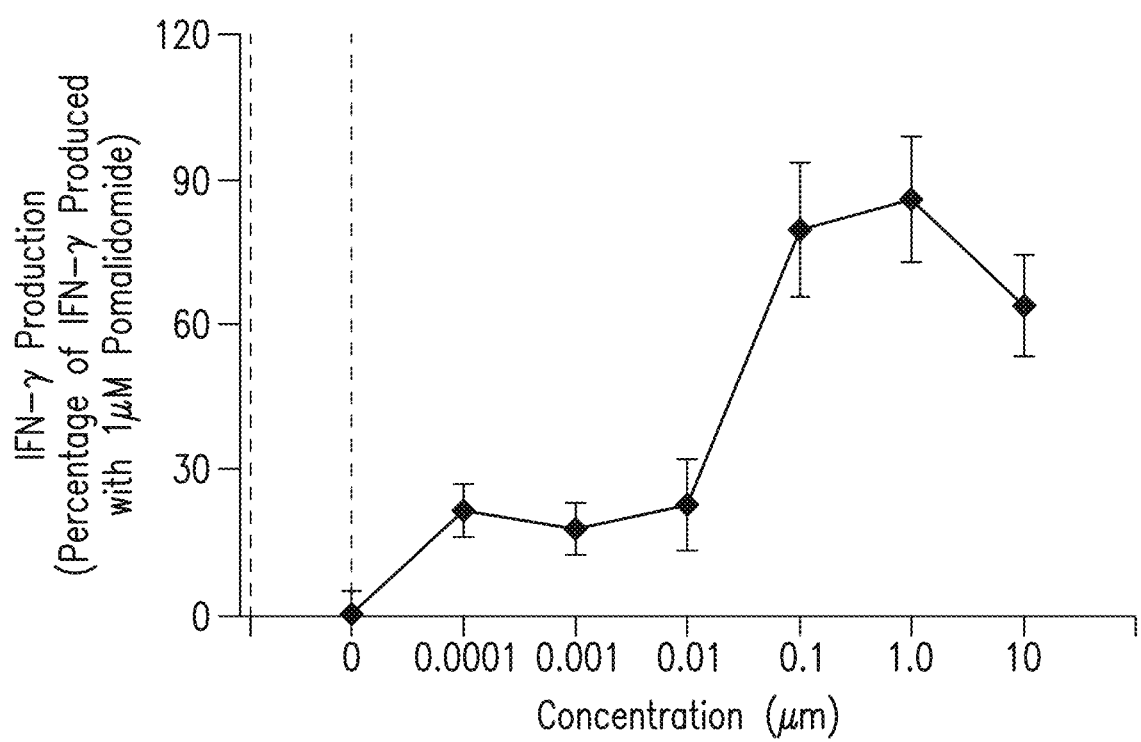
FIG. 38 illustrates enhancement of NK cell IFN-Gamma Production in Response to Immobilized IgG and IL-2, expressed as percentage of amount of IFN-gamma produced in the presence of 1 μm pomalidomide, by (S)-3-[4-(4-morphlin-4-ylmethylbenzyloxy)-1-oxo-1,3-dihydro-isoindo-2-yl]piperidine-2,6-dione.

The test compounds enhanced NK cell IFN-γ production in a dose dependent manner in response to immobilized IgG and IL-2 stimulation. Results for the racemate, R-enantiomer and S-enantiomer are provided in FIGS. 33-35 (expressed as pg/mL of IFN-γ produced), respectively. FIGS. 36-38 provide results expressed as a percentage of increased IFN-γ produced relative to the IFN-γ produced in the presence of pomalidomide at 1 µM for the racemate, R-enantiomer and S-enantiomer, respectively. Each value plotted in FIGS. 33-38 represents the mean of 12-14 determinations SEM.

8.7 Example 7: Human Vascular Endothelial Cell Proliferation, Tube Formation, Migration, and Invasion Assays In this example, racemate refers to 3-[4-(4-morphlin-4-ylmethylbenzyloxy)-1-oxo-1,3-dihydro-isoindo-2-yl]piperidine-2,6-dione, R-enantiomer refers to (R)-3-[4-(4-morphlin-4-ylmethylbenzyloxy)-1-oxo-1,3-dihydro-isoindo-2-yl]piperidine-2,6-dione and S-enantiomer refers to (S)-3-[4-(4-morphlin-4-ylmethylbenzyloxy)-1-oxo-1,3-dihydro-isoindo-2-yl]piperidine-2,6-dione.

Human Umbilical Vascular Endothelial Cells Proliferation Assay: Human umbilical vascular endothelial cells were thawed and grown in EGM2 medium until passage 3 to 6 for all proliferation assays. Human umbilical vascular endothelial cells were trypsinized, washed with 20% FBS/M199 medium and plated with the same medium at 104 cells/100 µL per well to 96-well cell culture plates. The plates were incubated overnight at 37° C. to allow cells to adhere. The cells were then starved in 1% FBS/M199 medium for 18 hours after washing with the same medium 3 times. For optimization of the concentration of the growth factors in the HUVEC proliferation assay, 100 µL/well of the 2× serial diluted growth factors, starting at 100 ng/mL, were added to HUVECs in duplicate for 72 hours at 37° C. in a humidified cell culture incubator with 5% CO2. For analysis of test compounds, a serial dilution of the test compounds in 0.4% DMSO/1% FBS/M199 medium in duplicate was made from the 10 mM stock. Fifty microliters per well of the serially diluted test compounds (10, 1.0, 0.1, 0.01, 0.001, 0.0001, 0.00001 µM) were added to the cells for 1 to 2 hours at 37° C. The final DMSO concentration in the cells is 0.1%. Then 50 µL of 4× final concentration of relative growth factors was added to each well in duplicate for 72 hours at 37° C. in a humidified cell culture incubator with 5% CO2. Thymidine incorporation was measured by adding one microcurie of 3H-thymidine (Amersham) in 20 µL medium to each well and incubated at 37° C. in a humidified cell culture incubator with 5% CO2 for 5 to 6 hours. The cells were then trypsinized and harvested onto UniFilter GF/C filter plates (Perkin Elmer) by using the cell harvester (Tomtec). After the plates were air dried, 20 L/well of Microscint 20 (Packard) was added then the plates were analyzed in TopCount NXT (Packard). Each well was counted for one minute. The experiments were performed in duplicate in each of 3 donors.

Human Umbilical Vascular Endothelial Cell Tube Formation Assay: Compounds were tested in the growth factor-induced HUVEC tube formation assay. The tube formation plates were incubated at 37° C. for 30 minutes for matrigel to polymerize. The HUVECs were starved in 0.1% BSA basal EBM2 medium for 5 hours after washing with the same medium 3 times. The cells were trypsinized and centrifuged. Then 25 µL of 4× serially diluted compounds (10, 1, 0.1, 0.01, 0.001, 0.0001, 0.00001 µM) were added in duplicate with 50 µL of 2×104 cells/well to tube formation plates coated with matrigel. Fifty L of 4×VEGF (final concentration=25 ng/mL) or bFGF (final concentration=10 ng/mL) were added to the plates. The cells were then incubated overnight (~18 hours) at 37° C. in a humidified incubator. The tubule webs were stained with calcein AM at 4 µg/µL in 2% FBS/HBSS for 30 minutes and images taken by fluorescence microscopy. The tubules were quantified by the MetaMorph tube formation software program for tube area and tube length.

Human Umbilical Vascular Endothelial Cell Invasion Assay: In the HUVEC invasion assay, the concentration of human fibronectin is optimized to provide a suitable protein structure for adherent cells to attach to the membrane and allow free migration in response to an angiogenic stimulus (e.g. VEGF, bFGF, or HGF) in the lower chamber of the insertplate. HUVECs were starved in 0.1% BSA EBM2 medium for 6 hours after washing with the same medium 3 times. The cells were then trypsinized and centrifuged to remove the remaining trypsin. Then ~0.5 to 1×106 cells in 125 µL/well and 125 µL of 8× serially diluted compounds (10, 1, 0.1, 0.01, 0.001 µM) were added to the upper chamber of the BD Falcon 24-well and 96-well insert plates in duplicate and incubated for −1 to 2 hours. (The plates contain a fluorescence blocking, microporous [3.0 µm pore size] PET membrane that has been evenly coated with human fibronectin.) Seven hundred fifty microliters of a 1.33×stock solution of VEGF (final concentration of 25 ng/mL), bFGF (final concentration of 10 ng/mL), or HGF (final concentration of 25 ng/mL) were then added to the lower chamber. The cells were incubated for 22±1 hours at 37° C. The migrated cells were stained with calcein AM at 4 g/mL in HBSS containing 2% FBS, using 500 µL/well in 24-well plates and 200 µL/well in 96-well plates. The plates were incubated at 37° C. for 90 minutes and read in a fluorescence plate reader.

The percentage inhibition of cell proliferation, tube formation, migration, and invasion was calculated by subtracting the result for unstimulated DMSO control from test sample results, averaging all replicates, and normalizing to the growth factor-stimulated DMSO control (0% inhibition). The IC50 values were calculated by using GraphPad Prism 5.0.

Figure 39:
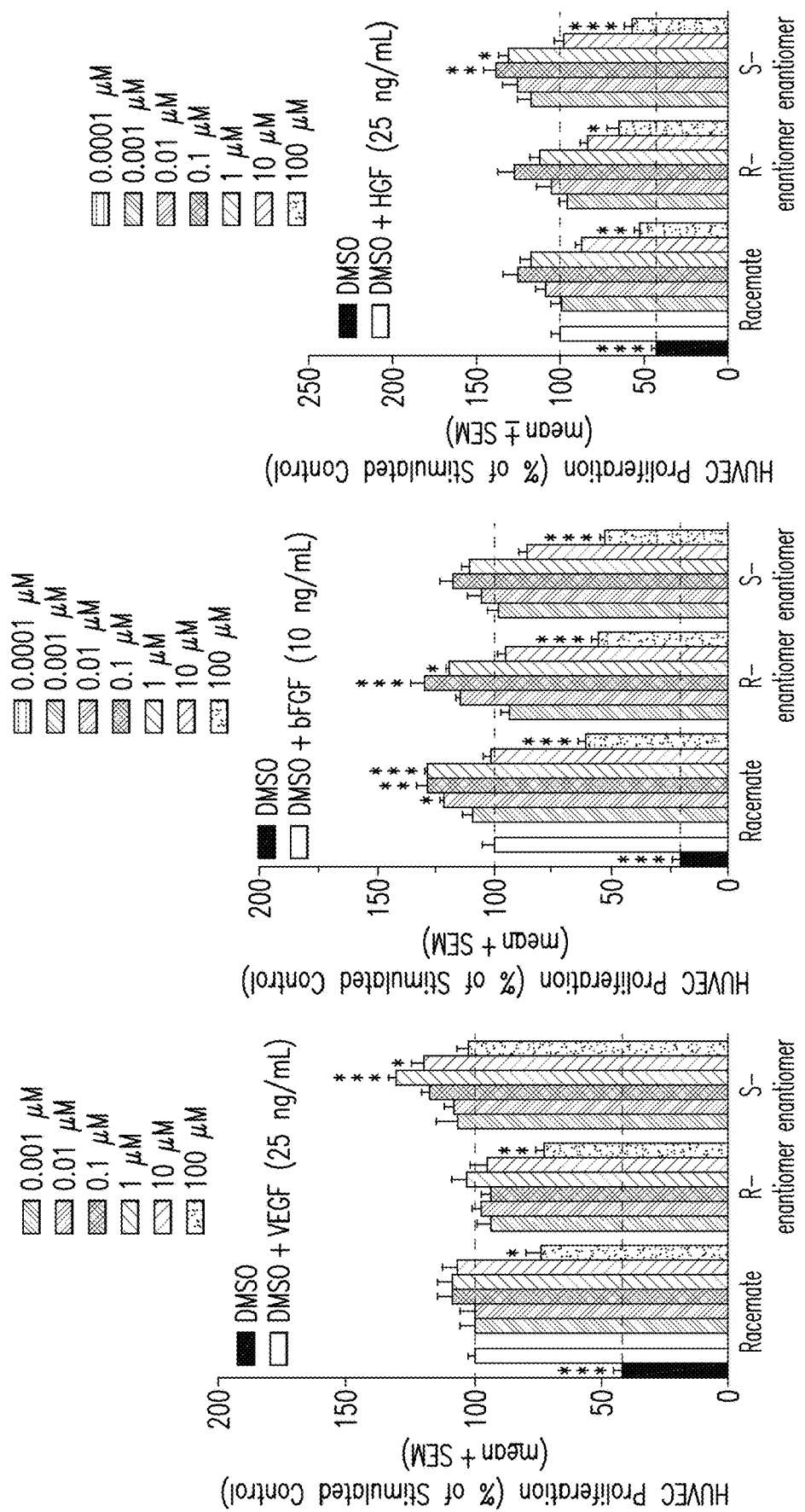
FIG. 39 depicts effect of compounds provided herein on growth factor-induced human umbilical vascular endothelial cell proliferation.

Human Umbilical Vascular Endothelial Cells Proliferation Assay Results: Results from the growth factor optimization study indicated that the optimal concentrations of VEGF, bFGF, and HGF for induction of proliferation were 25, 10, and 25 ng/mL respectively. The test compounds were examined with optimized growth factor concentrations and results indicated that the racemeate, S-enantiomer, and R-enantiomer did not inhibit VEGF-, bFGF-, or HGF-induced HUVEC proliferation (FIG. 39). However, there was a significant enhancement of proliferation observed in the VEGF- and HGF-treated HUVECs by S-enantiomer (VEGF-treated: 1-10 µM; HGF-treated: 0.1-1 µM). Also there was a significant enhancement observed in the bFGF-treated HUVECs by racemate (0.01-1 µM), and R-enantiomer (0.1-1 µM). $IC_{50}$ values are summarized in the Table 7.

TABLE 7

Summary of $IC_{50}$ Values from Growth Factor-induced Human Umbilical Vascular Endothelial Cell Proliferation Studies

| Test Compounds | VEGF (25 ng/mL) $IC_{50}$ Values (µM) | bFGF (10 ng/mL) $IC_{50}$ Values (µM) | HGF (25 ng/mL) $IC_{50}$ Values (µM) |
|---|---|---|---|
| Racemate | >100 | 99 | 24 |
| R-enantiomer | >100 | 76 | 38 |
| S-enantiomer | >100 | 52 | 51 |

Figure 40:
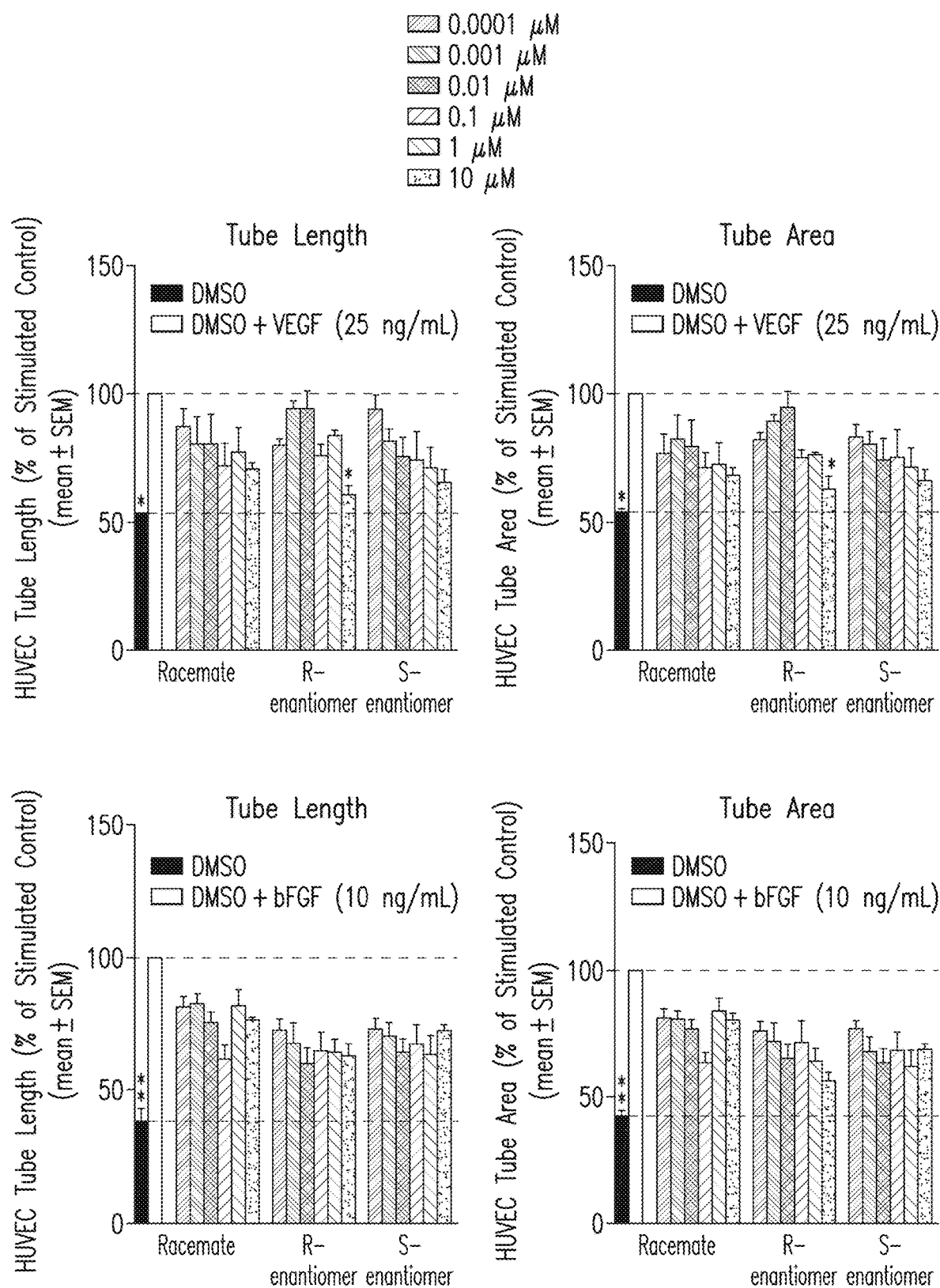
FIG. 40 depicts effect of compounds provided herein on growth factor-induced human umbilical vascular endothelial cell tube formation.

Human Umbilical Vascular Endothelial Cell Tube Formation Assay Results: The test compounds displayed a trend toward inhibiting VEGF-induced HUVEC tube formation in terms of both tube length and tube area (FIG. 40). All compounds demonstrated a dose-dependent effect on VEGF-induced HUVEC tube formation.

R-enantiomer showed significant inhibition (p<0.05 vs stimulated DMSO control) of tube area and length at 10 µM. There was also a trend for the compounds to inhibit bFGF-induced HUVEC tube formation in terms of both tube length and tube area (FIG. 40), although the effect was less pronounced than the effects on VEGF-induced HUVEC tube formation.

Figure 41:
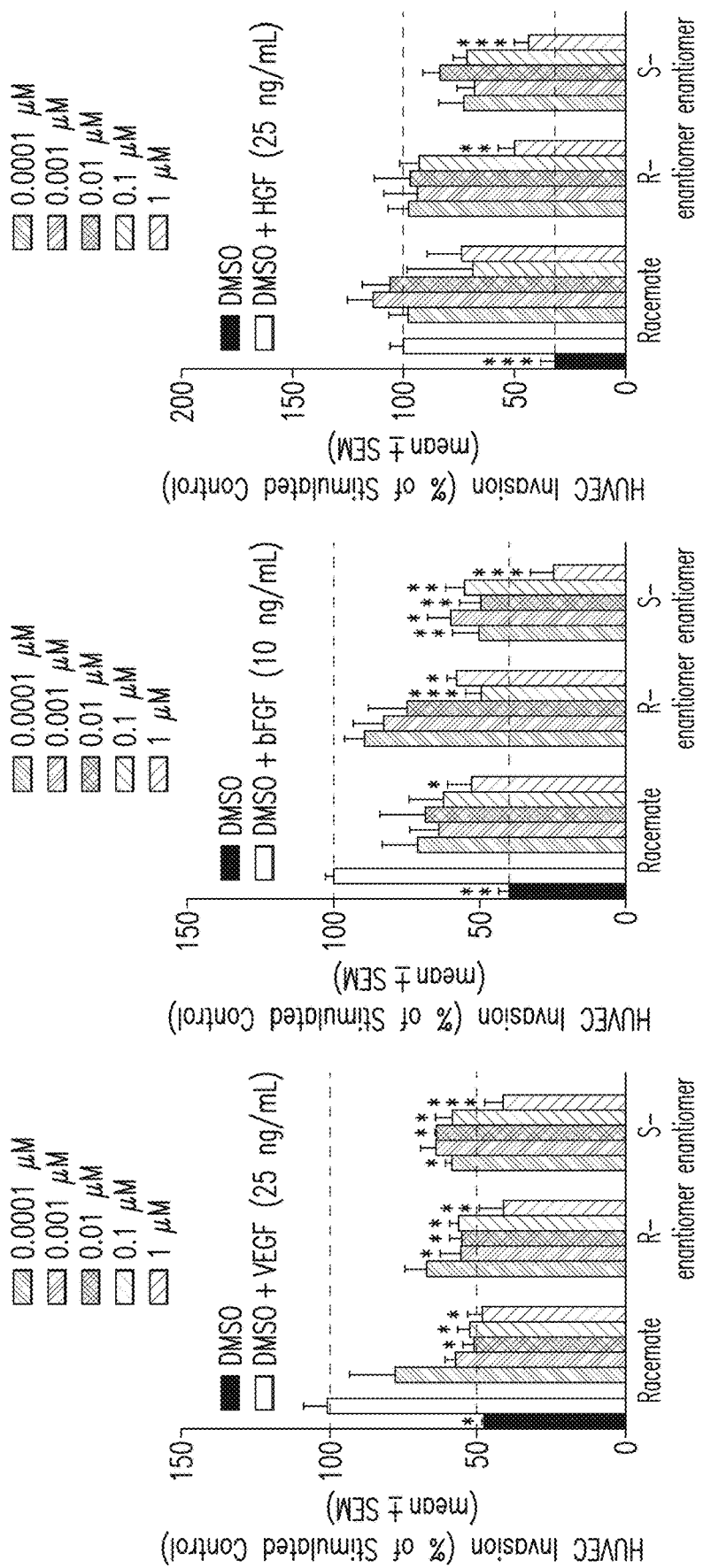
FIG. 41 depicts effect of compounds provided herein on growth factor-induced human umbilical vascular endothelial cell invasion.

Human Umbilical Vascular Endothelial Cell Invasion Assay Results: 3-[4-(4-morphlin-4-ylmethylbenzyloxy)-1-oxo-1,3-dihydro-isoindo-2-yl]piperidine-2,6-dione, (R)-3-[4-(4-morphlin-4-ylmethylbenzyloxy)-1-oxo-1,3-dihydro-isoindo-2-yl]piperidine-2,6-dione and (S)-3-[4-(4-morphlin-4-ylmethylbenzyloxy)-1-oxo-1,3-dihydro-isoindo-2-yl]piperidine-2,6-dione significantly inhibited VEGF-, bFGF-, and HGF-induced HUVEC invasion in a dose-dependent manner (FIG. 41). The compounds were more potent against VEGF- and bFGF-induced HUVEC invasion than against HGFinduced HUVEC invasion (Table 8). The $IC_{50}$ value was <0.3 nM for inhibition of VEGFinduced HUVEC invasion by the test compounds. The $IC_{50}$ of racemate (0.4 nM) and S-enantiomer (<0.1 nM) were more than ten times as potent as the R-enantiomer (13 nM) (Table 8).

TABLE 8

Summary of the Effect of Test Compounds on Growth Factor-induced Human Umbilical Vascular Endothelial Cell Invasion

| Test Compounds | VEGF-induced invasion $IC_{50}$ Values (µM) | bFGF-induced invasion $IC_{50}$ Values (µM) | HGF-induced invasion $IC_{50}$ Values (µM) |
|---|---|---|---|
| Racemate | 0.00014 | 0.00042 | 0.59 |
| R-enatiomer | <0.0001 | 0.013 | 0.45 |
| S-enantiomer | <0.0001 | <0.0001 | 0.019 |

8.8 Example 8: Lupus/Fibrosis Mouse Model Study

In this example, sensitivity (S)-3-[4-(4-morphlin-4-ylmethylbenzyloxy)-1-oxo-1,3-dihydro-isoindo-2-yl]piperidine-2,6-dione was tested in two lupus-prone mouse strains: MRL/MpJ-Faslpr/J mouse model of systemic lupus erythematosus and NZBWF1/J mouse model of systemic lupus erythematosus. The test compound was administered in both models at 30 mg/kg.

In MRL/MpJ-Faslpr/J mouse model of systemic lupus erythematosus, peripheral blood B cells showed no change at week 4. Splenic B cells showed 37% increase and anti-double stranded DNA autoantibody level showed 25% decrease at week 4.

In NZBWF1/J mouse model of systemic lupus erythematosus, peripheral blood B cells showed 25% decrease at week 4, splenic B cells showed no change, and anti-double stranded DNA autoantibody level showed 86% increase at week 4.

8.9 Example 9: Dermal Fibrosis Mouse Model Study

In this example, (S)-3-[4-(4-morphlin-4-ylmethylbenzyloxy)-1-oxo-1,3-dihydro-isoindo-2-yl]piperidine-2,6-dione was tested in the bleomycin-induced skin fibrosis model using both prophylactic and therapeutic dosing regimens. Bleomycin is an outmoded anticancer therapeutic that has been demonstrated to cause fibrosis in the lung. In animal models it will similarly induce injury and fibrosis at the site of delivery.

The following abbreviations are used in this example:

| Abbreviation or Specialist Term | Explanation or Definition |
|---|---|
| ANOVA | Analysis of Variance |
| α-SMA | Alpha Smooth Muscle Actin |
| CMC | Carboxymethyl Cellulose |
| ECM | Extracellular Matrix |
| NaCl | Sodium Chloride |
| PO | orally |
| QD | Once daily dosing |
| SSc | Systemic Sclerosis |

DBA/2 mice were used in this study. Eight animals were used per treatment group in the study. Mice were kept in the animal house under standard conditions with food and water ad libitum.

The vehicle, 0.5% carboxymethyl cellulose (CMC)/0.25% Tween 80, was prepared in distilled $H_2O$ and dissolved overnight on a magnetic stirrer (add 0.5 g CMC; Sigma #C9481) and 0.25 ml Tween 80 (Sigma #P8074) to 99.75 ml to make a total of 100 ml 0.5% CMC/0.25% Tween 80).

The test compound powder was weighed out and suspended fresh daily in the vehicle 0.5% CMC/0.25% Tween 80, to avoid drug hydrolysis in the aqueous medium. The compound was suspended, not dissolved, in this vehicle. The formulation was homogenized with a Teflon pestle and mortar (Potter-Elvehjem tissue grinder) using a motorized Eberbach tissue homogenizer. The daily drug stock concentration used in these studies was 3 mg/ml.

Bleomycin was obtained from the pharmacy of the University of Erlangen-Nuremberg and freshly prepared once a week. Skin fibrosis was induced in 6-week-old DBA mice by local intracutaneous injections of 100 μl of bleomycin dissolved in 0.9% NaCl, at a concentration of 0.5 mg/ml, every other day in defined areas of 1.5 $cm^2$ on the upper back.

8.9.1 Study Design

The mouse model of bleomycin induced dermal fibrosis is widely used to evaluate anti-fibrotic therapeutics. In this model, a localized dermal fibrosis is induced by intradermal injections with bleomycin every other day for 3 weeks. This model resembles early, inflammatory stages of SSc. To evaluate potential effects on prevention of fibrosis, treatment was initiated simultaneously with the first bleomycin injection. To study the effect of test compound on prevention of bleomycin-induced dermal fibrosis in vivo, the treatments were divided into following groups:

Control group: Intradermal injection of NaCl for 3 weeks. Treatment consisted of administration of the vehicle (0.5% CMC/0.25% Tween 80).

Untreated bleomycin group: Intradermal injection of bleomycin for three weeks. Administration of the vehicle (0.5% CMC/0.25% Tween 80).

Test compound group: Intradermal injection of bleomycin for three weeks. The test compound was administered at 30 mg/kg; PO, QD.

Positive control group: Intradermal injection of bleomycin for three weeks. Injection of Imatinib (50 mg/kg; IP, QD). Imatinib mesylate has previously been shown to exert potent anti-fibrotic effects in bleomycin induced dermal fibrosis. See Akhmetshina A. et al., *Arthritis Rheum* 2009; 60(1):219-224.

To evaluate regression of fibrosis, a modified model of bleomycin induced dermal fibrosis was used. Mice were pre-challenged with bleomycin to induce a robust skin fibrosis. One group received treatment with the test compound, while challenge with bleomycin was ongoing for additional three weeks. The outcome of this group was compared to mice challenged with bleomycin for six weeks (prevention of further progression) and to mice challenged with bleomycin for three weeks followed by NaCl for additional three weeks (induction of regression). The following groups were used in the regression study:

Control group: Intradermal injection of NaCl for six weeks. Control treatment consisted of administration of the vehicle.

Untreated bleomycin group 1 (regression): Intradermal injection of bleomycin for three weeks followed by intradermal injections of NaCl for another three weeks. Treatment consisted of administration of the vehicle.

Untreated bleomycin group 2 (prevention of progression): Intradermal injection of bleomycin for six weeks. Treatment consisted of administration of the vehicle.

Test compound group: Intradermal injection of bleomycin for six weeks. The test compound was administered at 30 mg/kg; PO, QD.

Positive control group: Intradermal injection of bleomycin for six weeks.

Injection of Imatinib (50 mg/kg; IP, QD)

8.9.2 Experimental Procedure

Dermal thickness was determined by staining with hematoxylin and eosin and activated fibroblasts by using immunohistochemistry for alpha smooth muscle actin (α-SMA). The dermal thickness, as determined by the modified Rodnan Skin Score, is currently the most common primary outcome in human clinical trials for anti-fibrotic agents in SSc. Skin sections were stained with hematoxylin/eosin for better visualization of the tissue structure. Dermal thickness was analyzed with a Nikon Eclipse 80i microscope (Nikon, Badhoevedorp, The Netherlands) by measuring the maximal distance between the epidermal-dermal junction and the dermal-subcutaneous fat junction at 4 different skin sections in each mouse. The evaluation was performed by 2 independent examiners.

For quantification of myofibroblasts, skin sections were deparaffinized and incubated with 5% bovine serum albumin for 60 minutes. Cells positive for α-SMA were detected by incubation with monoclonal anti-α-SMA antibodies (clone 1A4; Sigma-Aldrich, Steinheim, Germany) for 2 hours at room temperature followed by incubation with 3% hydrogen peroxide for 10 minutes. Goat anti-rabbit antibodies labeled with horseradish peroxidase (Dako, Hamburg, Germany) were used as secondary antibodies. The expression of α-SMA was visualized with 3,3-diaminobenzidine tetrahydrochloride (Sigma-Aldrich). Monoclonal mouse IgG antibodies (Calbiochem, San Diego, Calif.) were used as controls.

In addition, the amount of collagen in lesional skin will be measured with the SirCol collagen assay; RNA and plasma of all mice were saved for further analyses.

Figure 42:
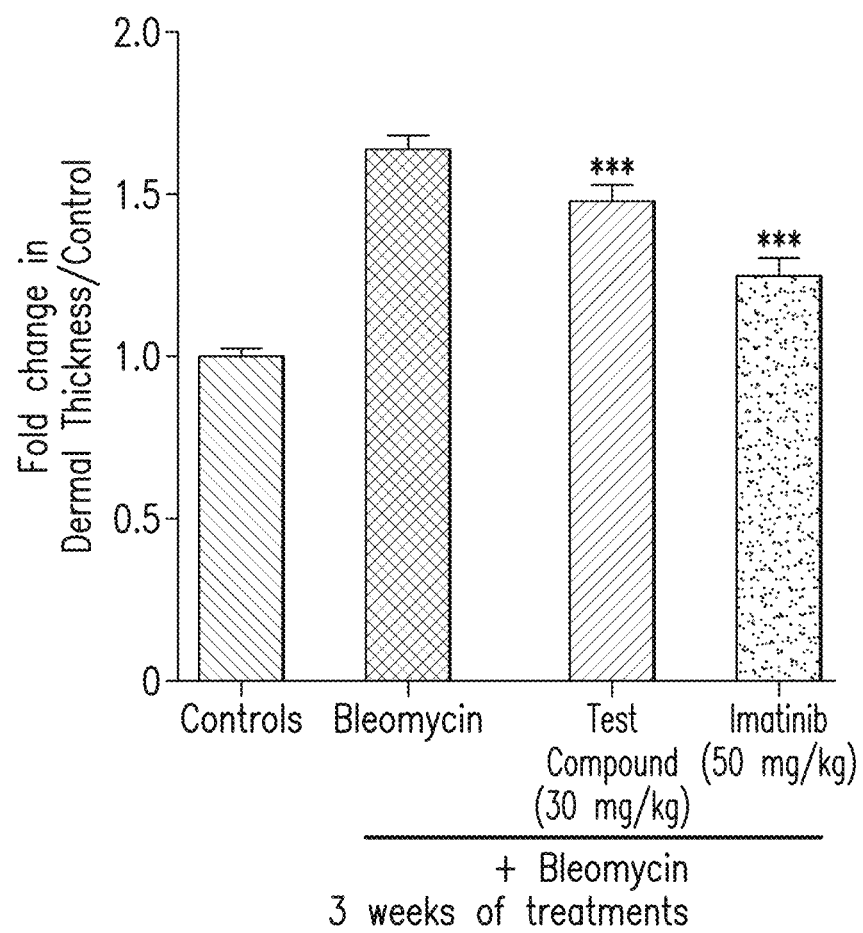
FIG. 42 depicts effect of (S)-3-[4-(4-morphlin-4-ylmethylbenzyloxy)-1-oxo-1,3-dihydro-isoindo-2-yl]piperidine-2,6-dione on dermal thickness of lesional skin in the bleomycin dermal fibrosis mouse model (prevention of inflammation driven fibrosis).

The test compound significantly decreases dermal thickness of lesional skin in the bleomycin dermal fibrosis mouse model. The test compound at 30 mg/kg; PO, QD significantly prevented dermal thickening by approximately 25±0.49% ($p<0.001$, FIG. 42).

Figure 43:
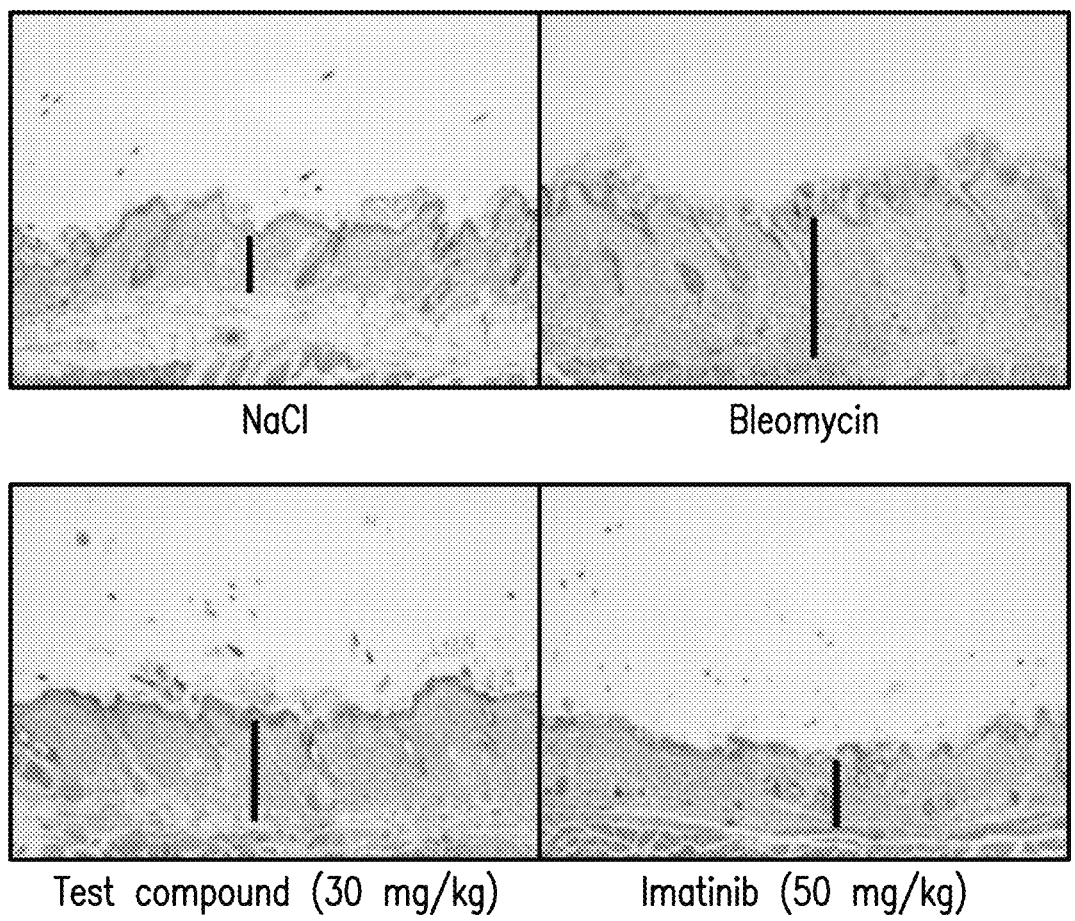
FIG. 43 depicts hematoxylin and eosin stained skin section photomicrographs showing dermal thickness of lesional skin in the bleomycin dermal fibrosis mouse model (prevention of inflammation driven fibrosis).

Representative photomicrographs of hematoxylin and eosin stained skin sections are shown in FIG. 43. Dermal thickness was assessed by measuring the maximal distance between the epidermal-dermal junction and the dermal-subcutaneous fat junction. The line drawn between the junction points shows the relative thickness in the treatment groups.

Figure 44:
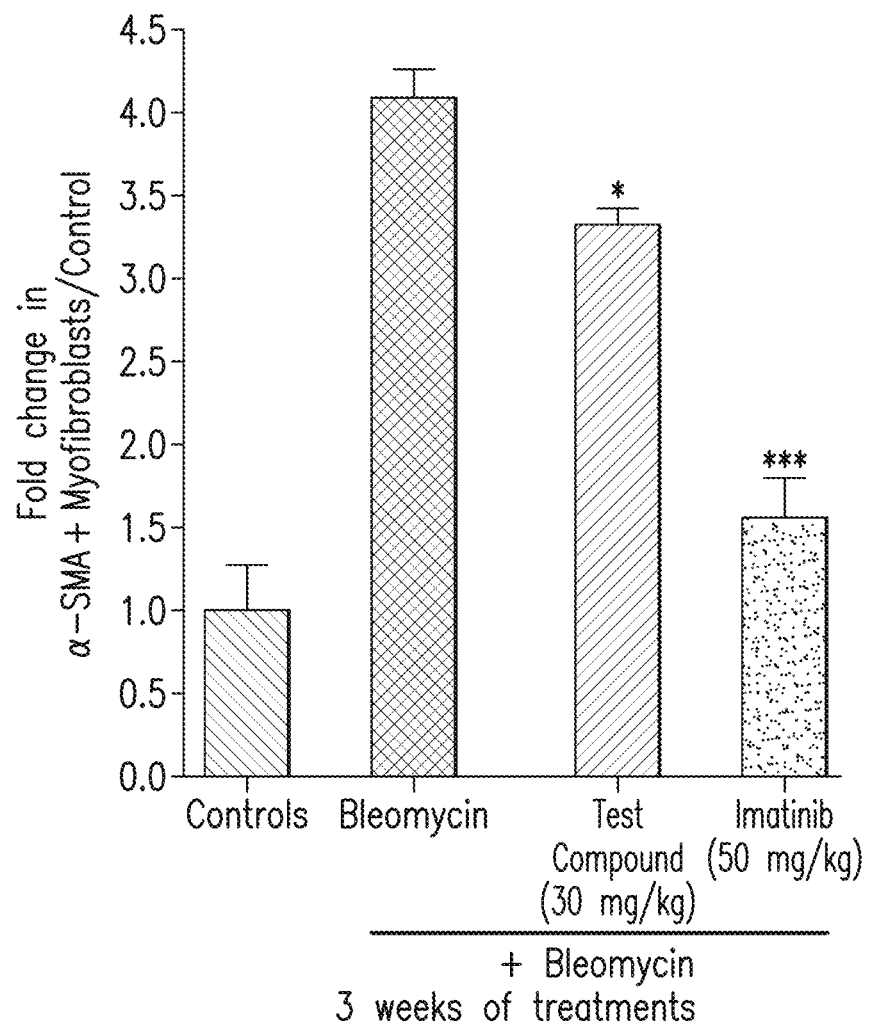
FIG. 44 depicts effect of (S)-3-[4-(4-morphlin-4-ylmethylbenzyloxy)-1-oxo-1,3-dihydro-isoindo-2-yl]piperidine-2,6-dione on the numbers of alpha-SMA+myofibroblasts in lesional skin in the bleomycin dermal fibrosis mouse model (prevention of inflammation driven fibrosis).

To determine the effect of the treatments on fibroblast activation, α-SMA+myofibroblasts were counted in lesional skin sections. As shown in FIG. 44, the test compound at 30 mg/kg; PO, QD reduced the number of myofibroblasts by 24±0.09% ($p<0.05$). Imatinib at 50 mg/kg reduced dermal thickening by 60±0.34% ($p<0.0001$) and myofibroblast numbers by 81±0.11% ($p<0.0001$).

8.9.3 Effect on the Regression of Bleomycin Induced Dermal Fibrosis

Figure 45:
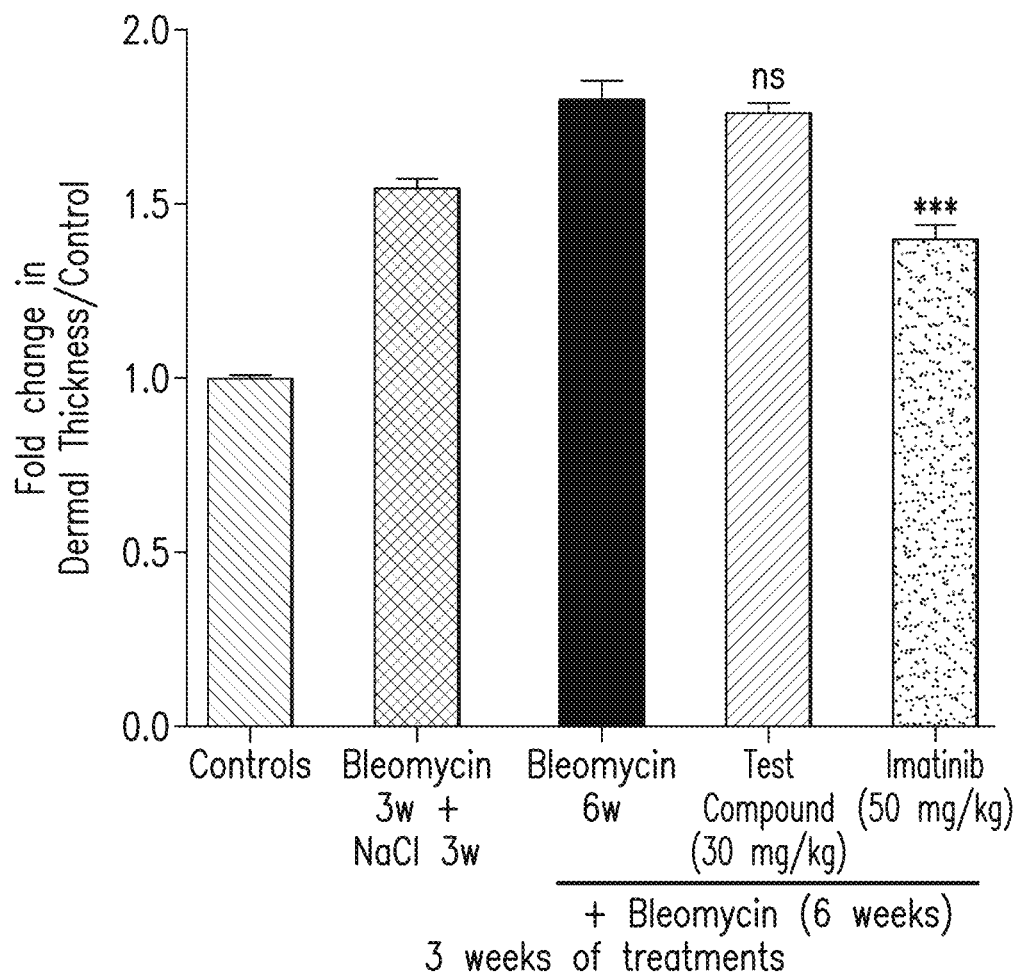
FIG. 45 depicts effect of compounds tested on dermal thickness of lesional skin in the bleomycin dermal fibrosis mouse model (regression of established fibrosis).
Figure 46:
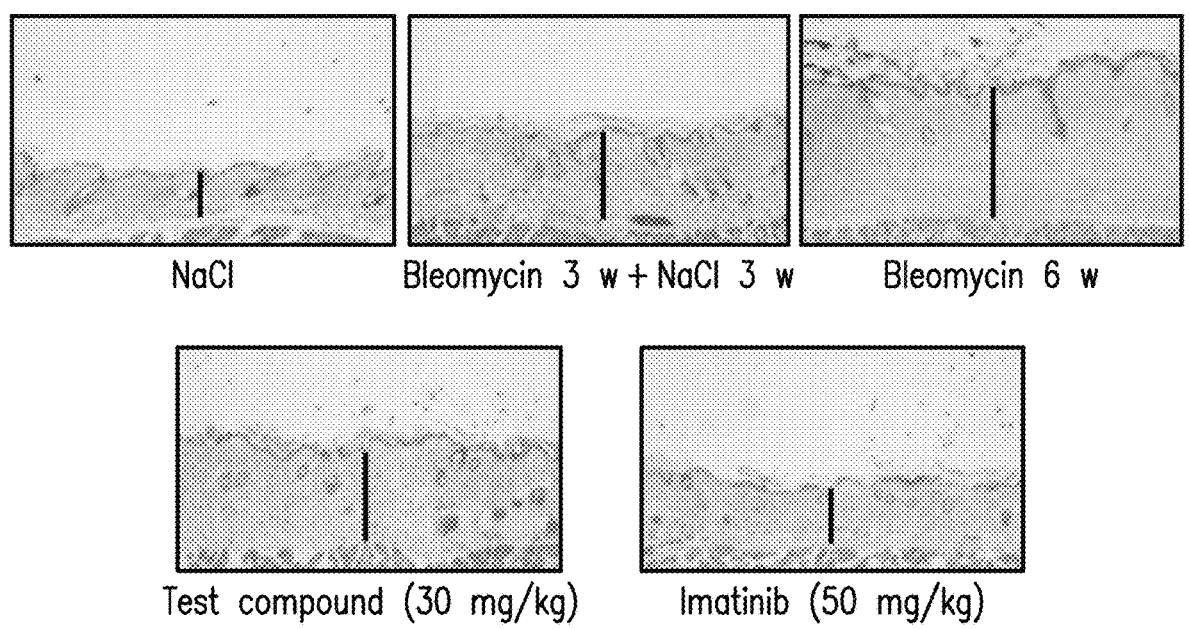
FIG. 46 depicts hematoxylin and eosin stained skin section photomicrographs showing dermal thickness of lesional skin in the bleomycin dermal fibrosis mouse model (regression of established fibrosis).
Figure 47:
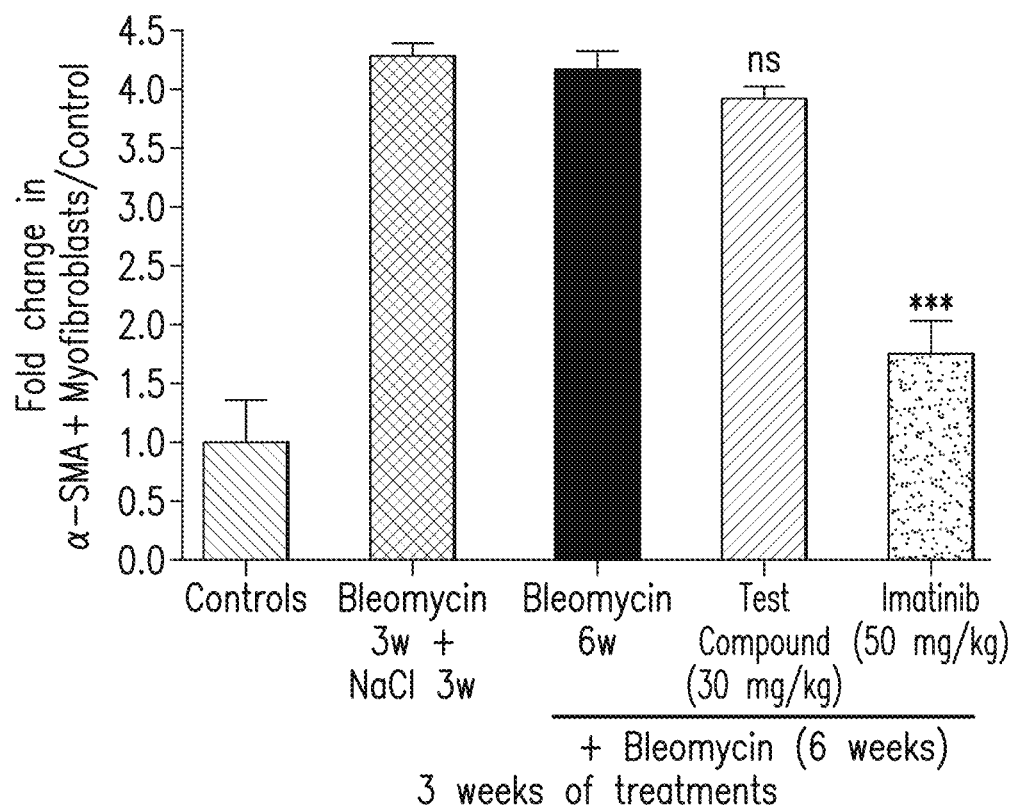
FIG. 47 depicts reduction in the numbers of alpha-SMA+ myofibroblasts in lesional skin in the bleomycin dermal fibrosis mouse model (regression of established fibrosis).

The inhibitory effects of the test compound on progression of fibrosis were also confirmed in the modified bleomycin model designed to investigate potential regression of fibrosis. As shown in FIG. 45, the test compound at 30 mg/kg; PO, QD had no effect on dermal thickening in the regression model. FIG. 46 shows photomicrographs of representative hematoxylin and eosin stained skin sections. Dermal thickness was assessed by measuring the maximal distance between the epidermal-dermal junction and the dermal-subcutaneous fat junction. The line drawn between the junction points shows relative thickness in the treatment groups. FIG. 47 shows that the test compound did not have an effect on the numbers of myofibroblasts. Imatinib at 50 mg/kg reduced bleomycin induced dermal thickness by 50±0.3% ($p<0.0001$) and myofibroblast numbers by 78±0.15% ($p<0.0001$).

8.10 Example 10: Effect in Tsk-1 Mouse Model

The antifibrotic effects of (S)-3-[4-(4-morphlin-4-ylmethylbenzyloxy)-1-oxo-1,3-dihydro-isoindo-2-yl]piperidine-2,6-dione were tested in the murine tight skin-1 (Tsk-1) mouse model.

Figure 48A:
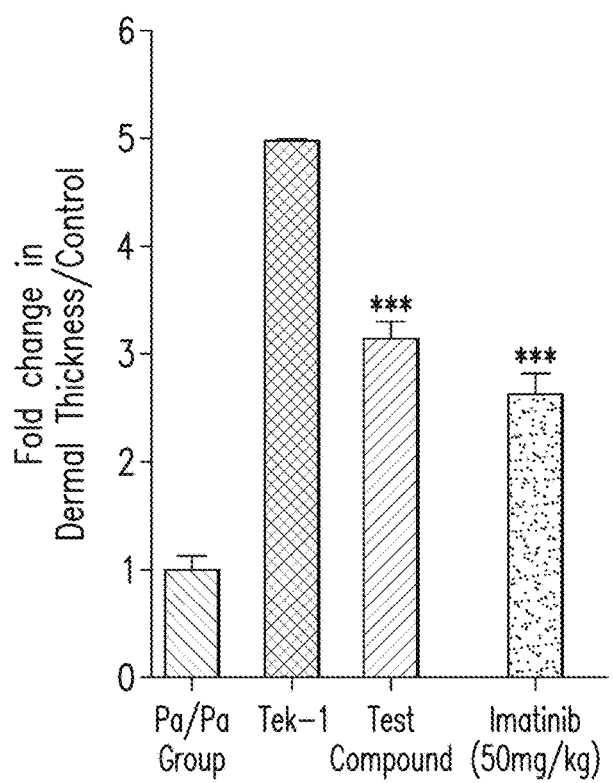
FIG. 48A depicts reduction of dermal thickness by (S)-3-[4-(4-morphlin-4-ylmethylbenzyloxy)-1-oxo-1,3-dihydro-isoindo-2-yl]piperidine-2,6-dione in TSK-1 mice.
Figure 48B:
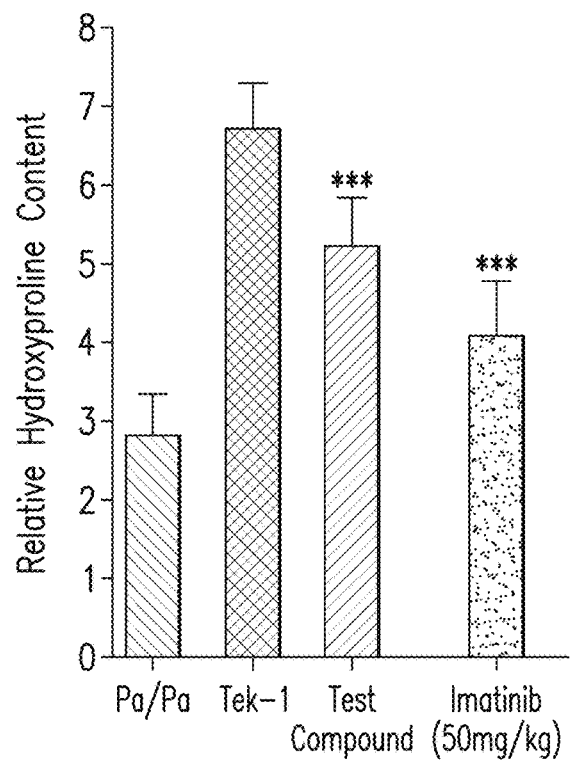
FIG. 48B depicts reduction of relative hydroxyproline contents by (S)-3-[4-(4-morphlin-4-ylmethylbenzyloxy)-1-oxo-1,3-dihydro-isoindo-2-yl]piperidine-2,6-dione in TSK-1 mice.

First, the inhibitory effects of the compound on fibrosis in the Tsk-1 tight skin mouse model were also investigated. As shown in FIG. 48, the compound at 30 mg/kg reduced the hypodermal thickening by 45% ($p\leq0.001$), compared to 58% reduction by imatinib at 50 mg/kg ($p\leq0.001$). The elevated collagen content of the skin, as measured by hydroxyproline levels, was reduced 38% by the compound, and 67% by imatinib ($p\leq0.001$).

Next, to examine the effect of the compound on the overexpression of TGF-β pathway genes in Tsk-1 mouse skin, qRT-PCR was used to measure mRNA levels for six genes: CTGF, PAI-1, COL1A1, α-smooth muscle actin (ALPHA SMA), cartilage oligomeric protein 1 (COMP), and TGFB1. Overexpression was defined as the excess mRNA levels observed in Tsk-1 mouse skin compared to normal pa/pa mouse skin. Among these six genes, only four (CTGF, PAI-1, COL1A1, and TGFB1) were expressed to a significantly higher level in Tsk-1 compared to normal pa/pa mice. The compound (30 mg/kg) significantly reduced the overexpression of CTGF and COL1A1 by 79% ($p\leq0.001$) and 129% ($p\leq0.001$), respectively (FIG. 49). PAI-1 and TGFB1 gene overexpression was not inhibited by the compound. These results indicate that the compound may reduce skin fibrosis by blocking the overexpression of some profibrotic genes within the TGF-β pathway.

To further examine the effect of the compound on the expression of fibrotic genes of normal (NL) and systemic sclerosis (SSc) cells, the following procedures were followed:

Cell cultures: Human normal and scleroderma skin fibroblasts were cultured in DMEM containing 10% fetal bovine serum (FBS). The cells were maintained in a humidified 5% CO2, 95% air incubator at 37° C. After confluence was reached, the cells were harvested with 0.05% trypsin and subcultured. Cells were used in the $3^{rd}$-$5^{th}$ passage.

Experimental design: Cells were grown to 70-80% confluence and placed into quiescent state by a reduction in serum concentration to 0.4% for overnight. The effects of the compound on TGFβ fibrotic effects and on NL and SSc fibrotic gene expression were tested.

Effects on TGFβ induction of fibrotic gene expression: NL fibroblasts were pretreated with the compound for 30 minutes followed by the addition of TGF-β1 to observe the effects of the compound on TGFβ induced fibrosis gene expression.

Effects of the compound on SSc-FB: SSc fibrobasts were treated with the compound at different concentration and gene expression levels of Collagen 1A1 (COL1), α-smooth muscle actin (α-SMA), fibronectin (FN), matrix metallopeptidase 1 (MMP1), plasminogen activator inhibitor (PAI), and DNA (cytosine-5-)-methyltransferase 1 (Dnmt1) were determined 24 hours later by real time PCR.

Quantitative Real-Time PCR: Total RNA was extracted from cells using RNeasy kit. RNA concentration was measured and 1 ug of RNA was reverse transcribed to cDNA using RT-First strand kit. The cDNA was then amplified using respective primers and Power SYBR Green PCR Master Mix. The amplicon (150-200 bp) was detected by ABI 7500 Real Time PCR System. All the target genes were normalized to GAPDH and relative fold changes were calculated. Each sample was assessed in triplicate.

Figure 50:
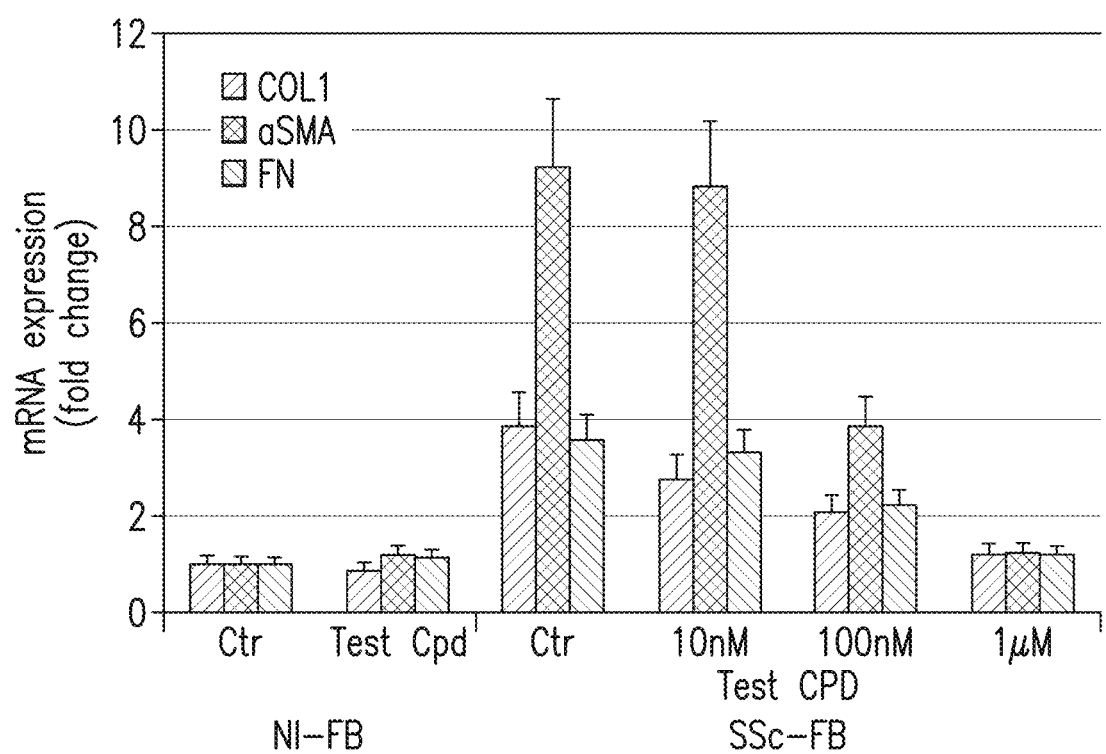
FIG. 50 depicts modulation of COL1, aSMA and FN by (S)-3-[4-(4-morphlin-4-ylmethylbenzyloxy)-1-oxo-1,3-dihydro-isoindo-2-yl]piperidine-2,6-dione.
Figure 51:
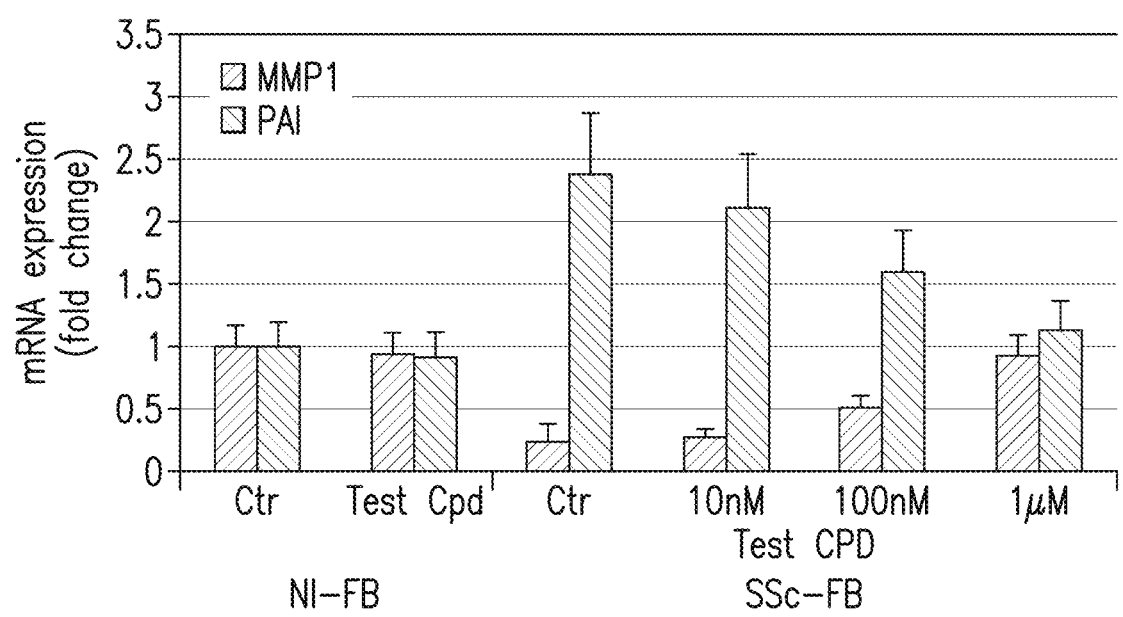
FIG. 51 depicts modulation of MMP1 and PAI by (S)-3-[4-(4-morphlin-4-ylmethylbenzyloxy)-1-oxo-1,3-dihydro-isoindo-2-yl]piperidine-2,6-dione.
Figure 52:
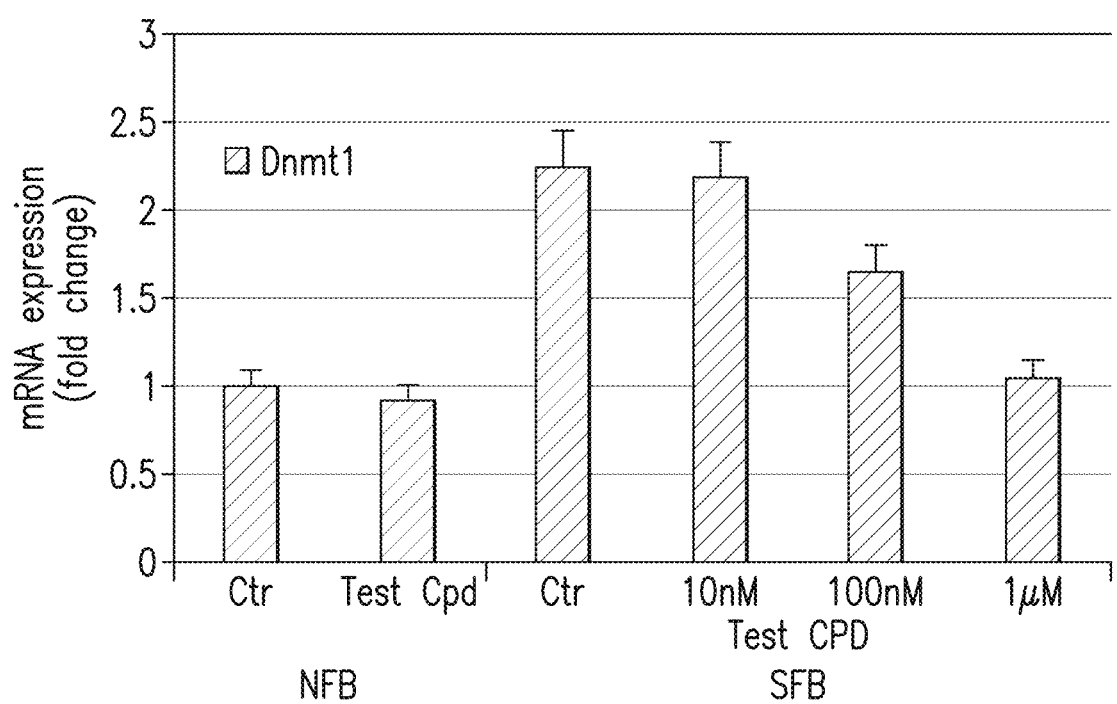
FIG. 52 depicts modulation of Dnmt1 by (S)-3-[4-(4-morphlin-4-ylmethylbenzyloxy)-1-oxo-1,3-dihydro-isoindo-2-yl]piperidine-2,6-dione.

As shown in FIG. 50, the compound dose dependently reduced the expression of COL1, aSMA and FN mRNAs in SSc fibroblasts. Similarly, the expression of PAI (FIG. 51) and Dnmt1 (FIG. 52) was also dose dependently reduced by the compound in SSc fibroblasts. As also shown in FIG. 51, the expression of MMP-1 was dose dependently increased by the compound in SSc fibroblasts. The results demonstrate that the compound potently regulates key fibrotic factors, indicating the efficacy of the compound in the treatment of SSc.

Figure 53:
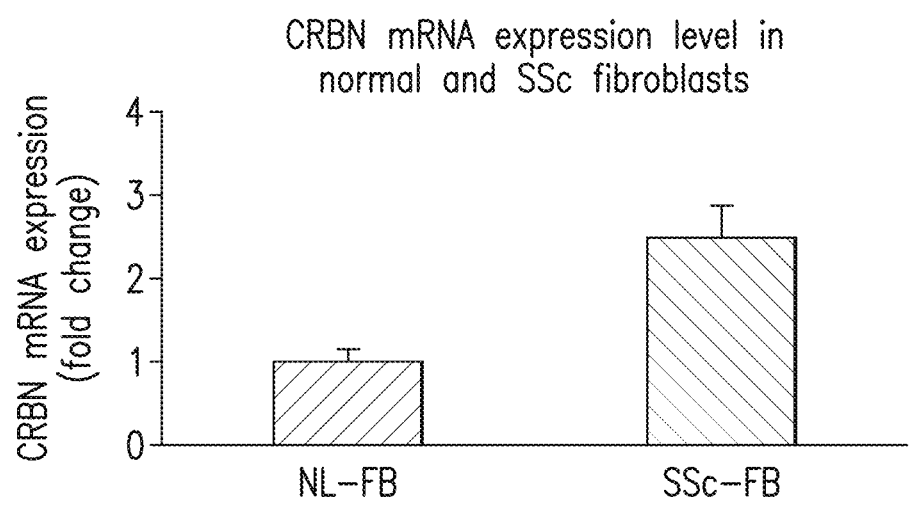
FIG. 53 depicts the mRNA expression level of cereblon in normal and SSc fibroblasts.
Figure 54:
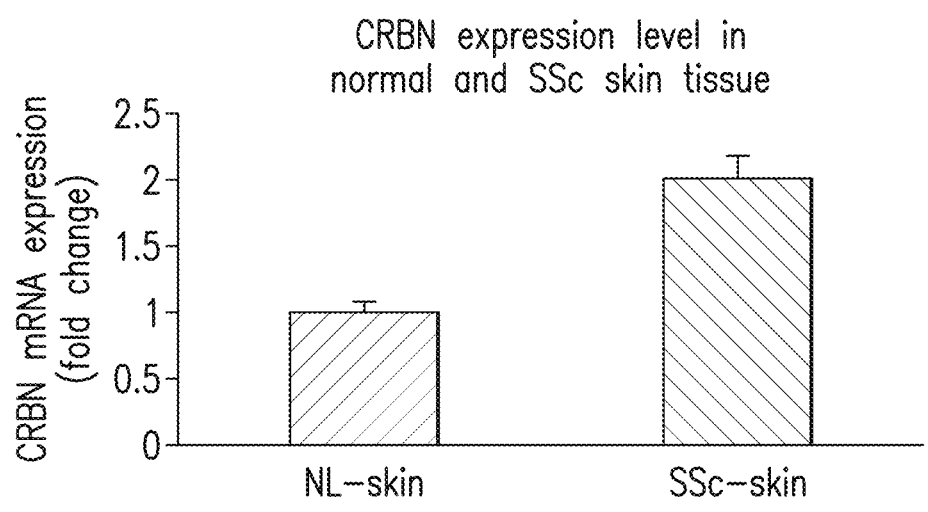
FIG. 54 depicts the mRNA expression level of cereblon in normal and SSc skin tissues.

In addition, the levels of cereblon in normal and SSc fibroblasts and skin tissues were examined. As shown in FIGS. 53 and 54, higher levels of cereblon were observed in both SSc fibroblasts and skin tissues as compared to the normal tissues. This indicates that an elevated level of cereblon is involved in SSc.

8.11 Example 11: Targeting Cereblon for B Cell Dyscrasias

The effect of (S)-3-[4-(4-morphlin-4-ylmethylbenzyloxy)-1-oxo-1,3-dihydro-isoindo-2-yl]piperidine-2,6-dione ("Compound IA") on CRBN binding, ubiquitination, and cell proliferation was profiled. CRBN is a component of the E3 ubiquitin ligase complex including CUL4A, DDB1, and ROC-1 and was found to be the molecular binding target of thalidomide, lenalidomide, and pomalidomide.

Binding studies to CRBN were conducted using thalidomide analog-conjugated beads in a competitive assay. Endogenous CRBN from human U266 multiple myeloma ("MM") cells was measured by incubating cell extracts with varying concentrations of either Compound IA or pomalidomide as a positive control. Affinity beads coupled to a thalidomide acid analog were incubated with the U266 extracts and, after extensive washing of the beads, the bound proteins were eluted. CRBN binding to the thalidomide-coupled affinity beads was determined by quantitative CRBN immunoblot determination.

CRBN ubiquitination was measured in HEK293T cells, which were transfected with an amino-terminal His-biotin-tagged CRBN construct, then preincubated with compounds for one hour followed by treatment with the MG132 proteasome inhibitor (to arrest degradation of ubiquitinated proteins). Cells were lysed and processed to measure CRBN ubiquitination by SDS-PAGE and immunoblot analysis using an anti-ubiquitin antibody. Cell proliferation studies were conducted in enalidomide-sensitive and refractory multiple myeloma cells. Lenalidomide-resistant or sensitive H929 MM cell lines were treated with Compound IA for 5 days, and then cell proliferation and viability were assessed by 7-aminoactinomycin D ("7-ADD") staining. T-cell costimulation was measured in purified primary human T cells stimulated using immobilized anti-CD3 antibody in cell culture for 2 days, and cytokine secretion was measured by ELISA.

Immunoglobulin M and G ("IgG and IgM") production was measured from normal donor peripheral blood mononuclear cells by culturing in the presence of the B cell differentiation factors recombinant human IL-2 (20 U/mL), IL-10 (50 ng/mL), IL-15 (10 ng/mL), His-tagged CD40 Ligand (50 ng/mL), polyHistidine mouse IgG1 antibody (5 µg/mL), and ODN 2006-Human TLR9 ligand (10 µg/mL) for 4 days, followed by IL-2, IL-10, IL-15, and IL-6 (50 ng/mL) for an additional 3 days. IgM and IgG were measured by ELISA.

In the competitive CRBN binding studies, preincubation with pomalidomide at concentration of 3 uM resulted in approximately 50% less CRBN bound to the affinity beads, while Compound IA at a concentration of 0.1 µM resulted in similar CRBN binding. CRBN ubiquitination studies in the transfected HEK293T cells resulted in the following potencies: Compound IA $IC_{50}$=0.19 µM; lenalidomide $IC_{50}$=12.9 µM; and pomalidomide $IC_{50}$=21.6 µM. The $IC_{50}$ values for inhibition of proliferation by Compound IA shifted from 0.01 µM in the parental H929 cell line and 0.04 µM in the DMSO-treated subclone to 0.51-1.58 µM in the lenalidomide resistant subclones.

A 50% decrease in cell cycle (S-phase) was evident after 24 hours of treatment of H929 cells with Compound IA. At 48 hours, Compound IA decreased expression of survivin and retinoblastoma protein ("pRB") and increased expression of the cyclin-dependent kinase inhibitor p27. Compound IA co-stimulated IL-2 production by T cells with an $EC_{50}$ of approximately 0.29 nM, compared with 10 nM for pomalidomide. Compound IA inhibited IgM and IgG production with an $IC_{50}$ of 0.35 and 2.1 nM, respectively, compared to 17 nM and 63 nM for pomalidomide.

The results indicate that Compound IA binds to CRBN with approximately 30-fold higher affinity than pomalidomide, and inhibits CRBN ubiquitination with approximately 110-fold greater potency than pomalidomide in this system. Compound IA is approximately 34-fold more potent than pomalidomide for co-stimulating IL-2 production by T cells, and is 30 to 48-fold more potent than pomalidomide for inhibiting immunoglobulin production.

8.12 Example 12: Inhibition of B Cell Differentiation to the Plasmablast and Plasma Cell Lineage The effects of cereblon ("CRBN") targeting on the differentiation of B cells to the plasmablast and plasma cell lineages, an in vitro model of primary human B cell differentiation was developed.

CD19+ peripheral blood human B cells from normal donors, or total peripheral blood mononuclear cell PBMC for patients with systemic lupus erythematosus ("SLE"), were cultured in the presence of interleukin ("IL")-2, IL-10, IL15, TLR9 agonist, and CD40 L for 4 days, followed by IL-2, IL-6, IL-10 and IL-15 for another 3 days. Cells were counted, viability assessed, and expression of CD20, CD38, CD44, and CD83 were measured by flow cytometry. Plasmablast lineage factors IRF-4, BLIMP-1, XBP-1, and IgJ, and germinal center markers PAX-5 and BCL-6 were measured by qRT-PCR. Interacellular protein expression was measured by laser scanning cytometry. Secreted immunoglobulins IgG and IgM were measured by ELISA.

In normal B cell cultures, (S)-3-(4-((4-morphlinomethyl)benzyl)oxy)-1-oxoisoindolin-2-yl)piperidine-2,6-dione ("Compound I-S") reduced the percentage of total viable cells in these cultures after 4 days to 69.6% (P≤0.05) or 35.8% of control (P≤0.001) at 20 nM or 200 nM Compound I-S, respectively. Compound I-S decreased the percentage of viable CD20-CD38+ plasmablasts on day 7 from 30.4% in control cultures in a dose-dependent manner to 27.3%, 2.1%, and 0.4% at 2 nM, 20 nM, and 200 nM, respectively. On day 7, qRT-PCR analysis showed that Compound I-S (20 nM) reduced expression of the plasmablast lineage factors IRF-4, BLIMP-1, XBP-1, and IgJ gene expression to 20.5%, 14.3%, 15.1%, and 31.5% of control, respectively (P≤0.001).

By intracellular flow cytometry, Compound I-S (20 nM) significantly decreased IRF-4 (P<0.5), BLIMP-1 (P<0.05), and XBP-1 (P<0.05) protein expression at day 4, but significantly increased BCL-6 (P<0.05) protein expression on day 7. By laser scanning cytometry on day 7, Compound I-S (20 nM) reduced CD38+ cell intracellular protein expression of IRF-4 (P≤0.001), and BLIMP-1 (P≤0.001), and increased BCL-6 expression (P≤0.05) (n=3). Compound I-S inhibited secreted IgG production with an IC50=1.8 nM (n=3).

In PBMC from SLE patients, Compound I-S (20 nM) had similar effects as in normal B cells, reducing BLIMP-1, XBP-1, and IgJ gene expression to 52.8%, 49.2%, and 13.6% of control, respectively (P≤0.001) (n=3). Compound I-S (20 nM) significantly reduced CD38+ plasmablast intracellular protein expression of BLIMP-1 (P≤0.01) and IRF-4 (P≤0.001), and increased BCL-6 (P≤0.05) (n=3). Compound I-S inhibited secreted IgM and IgG production by SLE patient PBMC with IC50s of 0.9 nM and 3.2 nM, respectively (n=3).

These results demonstrate that targeting of the E3 ubiquitin ligase complex substrate co-receptor CRBN with the small molecule immunomodulatory compound Compound I-S results in potent inhibition of B cell differentiation to the plasmablast lineage, as shown by a reduction in the percentage of viable CD38+ cells, a decrease in BLIMP-1, XBP-1, IRF-4, and IgJ gene and protein expression, and inhibition of

8.13 Example 13: Clinical Studies: Chronic Cutaneous

Sarcoid

Study Design

A clinical study is conducted to examine the efficacy and safety of multiple dose levels of Compound I-S in subjects with chronic cutaneous sarcoid. The study employs a randomized, double-blind, placebo-controlled, sequential, dose-ascending design. The study is conducted in patients with CCS and who are receiving chronic stable therapy for their disease. Subjects may or may not have pulmonary involvement.

Two dose cohorts of Compound I-S(Cohort 1: 0.3 mg PO QD or matching placebo and Cohort 2: 0.6 mg PO QD or matching placebo) are evaluated using a sequential, dose-ascending design. Thirty-two subjects are randomized into each dose cohort at a 3:1 ratio (active to matching placebo). Subjects remain on their assigned treatment for up to 12 weeks. Enrollment are terminated when approximately 16 subjects have been randomized into each cohort.

The first group (Cohort 1) of approximately 16 subjects who meet the study entry criteria are randomized to 0.3 mg PO QD dose or matching placebo in a 3:1 ratio. After approximately 13 subjects in this cohort either complete the 4 weeks of treatment or discontinue the study early, a review of all blinded safety data is performed. If the safety profile is determined acceptable for Cohort 1, the enrollment of the remaining subjects into Cohort 1 continues and the randomization of 16 subjects into Cohort 2 (0.6 mg PO QD dose or placebo) in a 3:1 ratio commences. Subjects have regularly scheduled visits (weekly for the first month, then every 2 weeks for the next 2 months) to assess activity, safety, tolerability, efficacy, PK and PD of Compound I-S.

Study Population

Eligible subjects must have been diagnosed with CCS with or without pulmonary involvement. Subjects also have the following: i) documented histological diagnosis of CCS of ≥12 months duration; ii) CS biopsy demonstrating a confirmed diagnosis at screening; iii) minimum Modified Sarcoidosis Activity and Severity Index (MSASI) of ≥1 induration of observed lesion at randomization; iv) ≥2 lesion(s) >1 cm in longest dimension; v) no improvement in CCS ≥3 months prior to randomization (as deemed by the investigator), despite chronic therapy; v) forced vital capacity (FVC) of ≥45% of predicted normal value; and/or vi) estimated Glomerular Filtration Rate (eGFR)=≥60 mL/min. (calculated by MDRD [Modification of Diet in Renal Disease]).

Length of Study

This study consists of 3 phases of a maximum duration of 25 weeks: screening phase (up to 5 weeks), treatment phase (12 weeks), and post-treatment observational follow-up phase (8 weeks).

Efficacy Assessments

Efficacy assessments in this study include the following:

Modified Sarcoidosis Activity and Severity Index (MSASI): Subject's index lesion is evaluated and scored during screening using the Modified Sarcoidosis Activity and Severity Index (MSASI). The symptom domains of erythema, induration and desquamation are scored as follows: 0=None; 1=Slight; 2=Moderate; 3=Severe; and 4=Very Severe. The score for erythema and/or induration of the index lesion must be ≥1 for study eligibility.

The area score of the index lesion is assessed as follows: 0=0%; 1=1-9%; 2=10-29%; 3=30-49%; 4=50-69%; 5=70-89%; and 6=90-100%.

The MSASI is assessed at screening, baseline, Weeks 4, 8 and 12.

Physician's and Subject's Global Assessment of Disease Activity: The Physician's (Evaluator's) and Subject's Global Assessments of Disease Activity are recorded as a single vertical mark on a 100-mm visual analog scale (VAS), and serve as the subject and physician global VAS assessments of disease severity. The evaluation measures the degree of disease severity at the time of the examination using a 0-100 mm VAS scale. The subject global assessment of disease severity VAS is completed prior to the completion of investigator assessments. The physician global assessment of disease severity VAS is performed by the same trained investigator or sub-investigator at each visit. The physician's and the subject's global assessment of disease activity will be assessed at baseline, Weeks 1, 2, 4, 8, and 12.

6-Minute Walking Test: The 6MWT has emerged as an important addition to the prognostic evaluation of sarcoid. Published data suggest that the changes in 6MWT are clinically meaningful measures of a patients' daily activity, and is highly relevant to their quality of life (Lama et al., "Prognostic value of desaturation during a six minute-walk test in idiopathic interstitial pneumonia," Am. J. Respir. Crit. Care. Med. 2003, 168:1084e90; Hallstrand et al., "The timed walk test as a measure of severity and survival in idiopathic pulmonary fibrosis," Eur. Respir. J. 2005, 25:96e103). The 6MWT is assessed at baseline, and at Weeks 4, 8 and 12. The Borg Scale can be used in conjunction with the 6 MWT as follows: 0=no breathlessness at all; 0.5=very very slight (just noticeable); 1=very slight; 2=slight breathlessness; 3=moderate; 4=somewhat severe; 5=severe breathlessness; 7=very severe breathlessness; 9=very very severe (almost maximum); and 10=maximum.

Functional Assessment of Chronic Illness Therapy-Fatigue (FACIT-F): Chronic fatigue is often an accompanying component of CCS. The FACIT-F questionnaire is designed to measure anemia-related fatigue in cancer patients and is also gaining popularity in clinical trials outside of the cancer setting. The FACIT-F scale was used to demonstrate significant improvement in sarcoidosis-associated fatigue (Lower et al., "Double-blind, randomized trial of dexmethylphenidate hydrochloride for the treatment of sarcoidosis-associated fatigue," Chest 2008, 133(5):1189-95).

The questions fall into five subsets: physical well-being (PWB), social/family well-being (SWB), emotional well-being (EWB), functional well-being (FWB) and additional concerns (fatigue subset). Each of these subsets consists of questions with five responses ranging from zero to four, depicting "not at all" to "very much". The FACIT-F is completed at baseline, Weeks 4, 8, and 12.

Dermoscopy for Lesion Assessment: This is a noninvasive method that allows for an in vivo evaluation of the observed lesion. This technique compares the baseline lesion versus Week 12. The same lesion should be used for this assessment.

Physician's Overall Skin Response Assessment: The index lesion is a single, defined area of involvement that exhibits the most severe CS at screening and is located in such as position as to facilitate visual evaluation and measurement. The overall lesion evaluation for responder status is assessed by the investigator as follows: 1=markedly worsened; 2=worsened; 3=unchanged; 4=near resolution;

and 5=complete resolution. The measurement of index lesion includes measurement of the cross-sectional diameter of the index lesion (the diameter at the widest point of the lesion) and measurement of the diameter perpendicular to the first measurement.

Photography and Physician's Photographic Assessment of the Index Lesion: Photographic assessments are conducted in a subset of subjects at designated sites to provide supportive evidence of efficacy. Investigators will identify an area of the body where the index lesion is located, and take photographs of that same index lesion at baseline, Week 8 and Week 12. The investigator reassesses the same index lesion photographed at baseline, at both the Week 8 and Week 12 photographs. The investigator indicates his/her response, for example, as follows: much better after therapy, somewhat better after therapy, unchanged, somewhat worse after therapy, or much worse after therapy.

Pharmacokinetics: subjects participate in PK samplings.

Skin biopsy of Non-facial Lesion: All subjects have a skin biopsy performed on a CS lesion at the screening visit to reconfirm that they have active cutaneous sarcoid at study entry. This skin biopsy taken at the screening visit also serves as the baseline biopsy for those subjects who agree to having the optional biopsy collected at Week 12.

Two 4 mm diameter skin biopsies of the non-facial lesion are obtained. Evaluations includes changes in granuloma size and number, and epidermal thickness, and IHC staining for cells such as Giant cells, T cell staining (CD4 and CD8), and Dendritic cells/Langerhans staining (CD1a, CD83, DC-LAMP).

Blood Biomarker Analyses: The blood biomarker sampling is collected at the same time as the routine clinical laboratory blood draws, prior to the subject's morning dose. Blood samples are drawn at baseline, Weeks 4, 8, and 12 of the Treatment Phase, and at Weeks 16 and 20 of the Post-Treatment Observational Follow-up Phase. Evaluations include: serum ACE, IgG, 25-hydroxy vitamin D (25-OH-vit D), 1,25-dihydroxy vitamin D (1,25-vitD) levels; plasma biomarkers (e.g., IL-12, sIL2R and TNF-α); peripheral blood total lymphocyte counts and B cell subsets and T cell activation markers (such as but not limited to HLA-DR, CD45RA, CD45RO, CD69, IL-2R, CD80, CD86) via flow cytometry.

Pulmonary Function Tests: FVC and $FEV_1$ are measured at screening, baseline, Weeks 8 and 12 of the Treatment Phase. FVC measures the total amount of air that can be forcibly blown out after full inspiration. FVC is measured in liters. $FEV_1$ measures the amount of air that can be forcibly blown out in one second. $FEV_1$ is measured in liters. Along with FVC, $FEV_1$ is considered one of the primary indictors of lung function.

Chest Likert: The radiologist compares two radiographic films from the same patient. The films are taken at screening (this film also serves as the baseline image) and again at Week 12. The radiologist scores the two films on a Likert scale of 1 to 5 (markedly worsened, worsened, unchanged, improved, and markedly improved).

St. George's Respiratory Questionnaire (SGRQ): The SGRQ is a standardized self-completed questionnaire for measuring impaired health and perceived well-being ('quality-of-life') in airways disease. It has been designed to allow comparative measurements of health between patient populations and quantify changes in health following therapy. The SGRQ is completed only for those subjects who have pulmonary involvement at baseline, Weeks 4, 8, and 12 of the Treatment Phase.

Baseline and Transition Dyspnea Indices (BDI/TDI): The BDI/TDI provide interview-based measurements of breathlessness related to activities of daily living. The BDI is a discriminative instrument that includes specific criteria for each of three components (functional impairment, magnitude of task and magnitude of effort) at a single point in time. The TDI is an evaluative instrument that includes specific criteria for each of three components to measure changes from a baseline state. At baseline, dyspnea is rated using five grades from 0 (severe) to 4 (unimpaired) for each category to form a baseline score (0 to 12). During the transition period, the TDI assesses changes in dyspnea using seven grades ranging from −3 (major deterioration) to +3 (major improvement). The ratings for each of the three categories are then added to form a total transition focal score (range, −9 to +9). The BDI is performed at baseline, and the TDI is performed at Weeks 4, 8, and 12 of the Treatment Phase.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications, patents and patent applications are cited herein, the disclosures of which are incorporated by reference in their entireties.

What is claimed is:

1. A method for treating or managing an immune-related disease or an inflammatory disease comprising: a) identifying a patient suffering from the disease as having overproduction of IgG; and b) administering to the patient an effective amount of a compound, wherein the compound is (S)-3-(4-((4-(morpholinomethyl)benzyl)oxy)-1-oxoisoindolin-2-yl)piperidine-2,6-dione of the formula:

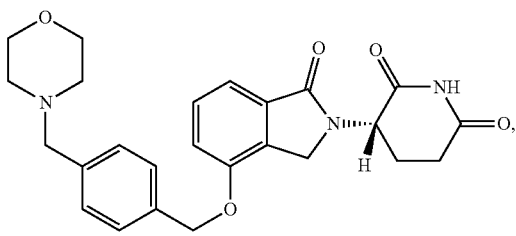 [SMILES: O=C1CC[C@H](N2Cc3c(OCc4ccc(CN5CCOCC5)cc4)cccc3C2=O)C(=O)N1]

or a pharmaceutically acceptable salt thereof, wherein the disease is lupus pernio or sarcoidosis.

2. The method of claim 1, wherein the compound is (S)-3-(4-((4-(morpholinomethyl)benzyl)oxy)-1-oxoisoindolin-2-yl)piperidine-2,6-dione.

3. The method of claim 1, wherein the compound is (S)-3-(4-((4-(morpholinomethyl)benzyl)oxy)-1-oxoisoindolin-2-yl)piperidine-2,6-dione hydrochloride.

4. The method of claim 1, wherein the disease is chronic cutaneous sarcoidosis.

5. The method of claim 4, wherein the chronic cutaneous sarcoidosis is with pulmonary involvement.

6. The method of claim 4, wherein the chronic cutaneous sarcoidosis is without pulmonary involvement.

7. The method of claim 1 further comprising administering a second active agent, which is an anti-inflammatory or immunomodulatory compound.

8. The method of claim 1, wherein the effective amount is about 0.005 mg/kg to about 10 mg/kg of the patient's body weight.

9. A method for reducing or inhibiting a symptom of sarcoidosis comprising: a) identifying a patient suffering from sarcoidosis as having overproduction of IgG; and b) administering to the patient an effective amount of a compound, wherein the symptom is selected from the group consisting of (i) granulomas formulation, (ii) lupus pernio, (iii) skin lesions, (iv) dyspnea, (v) dry cough, (vi) chest pain, and (vii) fatigue, and wherein the compound is (S)-3-(4-((4-(morpholinomethyl)benzyl)oxy)-1-oxoisoindolin-2-yl)piperidine-2,6-dione of the formula:

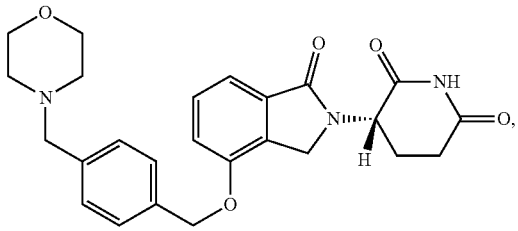 [SMILES: O=C1CC[C@H](N2Cc3c(OCc4ccc(CN5CCOCC5)cc4)cccc3C2=O)C(=O)N1]

or a pharmaceutically acceptable salt thereof.

10. A method for improving the Modified Sarcoidosis Activity and Severity Index (MSASI) score, the Physician's and Subject's Global Assessment of Disease Activity score, the 6WMT score, the FACIT-F score, the Dermoscopy for Lesion Assessment score, the Physician's Overall Skin Response Assessment score, the lesion, one or more biomarkers associated with sarcoidosis, forced vital capacity (FVC), the amount of air that can be forcibly blown out in one second ($FEV_1$), the chest radiographic Likert score, the Saint George's Respiratory Questionnaire score, or the dyspnea index (BDI)/transition dyspnea index (TDI) of a patient having sarcoidosis, comprising: a) identifying the patient as having overproduction of IgG; and b) administering to the patient an effective amount of a compound, wherein the compound is (S)-3-(4-((4-(morpholinomethyl)benzyl)oxy)-1-oxoisoindolin-2-yl)piperidine-2,6-dione of the formula:

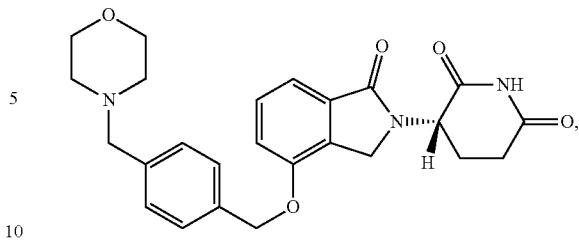

or a pharmaceutically acceptable salt thereof.

11. The method of claim 1, wherein the compound is administered at a dosage in the range of from about 0.3 mg once per day to about 0.6 mg once per day.

12. The method of claim 11, wherein the dosage is about 0.3 mg once per day.

13. The method of claim 11, wherein the dosage is about 0.6 mg once per day.

14. The method of claim 1, wherein the administration of the compound continues for a period of about 12 weeks.

15. The method of claim 9, wherein the compound is (S)-3-(4-((4-(morpholinomethyl)benzyl)oxy)-1-oxoisoindolin-2-yl)piperidine-2,6-dione.

16. The method of claim 9, wherein the compound is (S)-3-(4-((4-(morpholinomethyl)benzyl)oxy)-1-oxoisoindolin-2-yl)piperidine-2,6-dione hydrochloride.

17. The method of claim 9, wherein the effective amount is about 0.005 mg/kg to about 10 mg/kg of the patient's body weight.

18. The method of claim 10, wherein the compound is (S)-3-(4-((4-(morpholinomethyl)benzyl)oxy)-1-oxoisoindolin-2-yl)piperidine-2,6-dione.

19. The method of claim 10, wherein the compound is (S)-3-(4-((4-(morpholinomethyl)benzyl)oxy)-1-oxoisoindolin-2-yl)piperidine-2,6-dione hydrochloride.

20. The method of claim 10, wherein the effective amount is about 0.005 mg/kg to about 10 mg/kg of the patient's body weight.

\* \* \* \* \*